(12) United States Patent
Wagner et al.

(10) Patent No.: US 10,015,582 B2
(45) Date of Patent: Jul. 3, 2018

(54) EARBUD MONITORING DEVICES

(71) Applicant: Valencell, Inc., Raleigh, NC (US)

(72) Inventors: Wolfgang Wagner, Chapel Hill, NC (US); Shawn Stephenson, Raleigh, NC (US); Steven Matthew Just, Cary, NC (US); Michael Edward Aumer, Raleigh, NC (US); Jesse Berkley Tucker, Youngsville, NC (US); Lawrence Christopher Eschbach, Louisburg, NC (US); Steven Francis LeBoeuf, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 0 days.

(21) Appl. No.: 15/400,010

(22) Filed: Jan. 6, 2017

(65) Prior Publication Data

US 2017/0118551 A1   Apr. 27, 2017

Related U.S. Application Data

(63) Continuation of application No. 15/324,139, filed as application No. PCT/US2015/041562 on Jul. 22, 2015.

(Continued)

(51) Int. Cl.
*H04R 5/033* (2006.01)
*H04R 1/10* (2006.01)
(Continued)

(52) U.S. Cl.
CPC ......... *H04R 1/1091* (2013.01); *A61B 5/0261* (2013.01); *A61B 5/1455* (2013.01);
(Continued)

(58) Field of Classification Search
USPC ........ 381/74, 367, 370, 55, 58, 59; 600/301, 600/479
See application file for complete search history.

(56) References Cited

U.S. PATENT DOCUMENTS

| | | | |
|---|---|---|---|
| 3,595,219 | A | 7/1971 | Friedlander et al. |
| 4,240,882 | A | 12/1980 | Ang et al. |

(Continued)

FOREIGN PATENT DOCUMENTS

| | | |
|---|---|---|
| CN | 101212927 A | 7/2008 |
| CN | 201438747 U | 4/2010 |

(Continued)

OTHER PUBLICATIONS

Extended European Search Report corresponding to European Application No. 15830336.2 dated Jun. 7, 2017 (8 pages).

(Continued)

*Primary Examiner* — Yosef K Laekemariam
(74) *Attorney, Agent, or Firm* — Myers Bigel, P.A.

(57) ABSTRACT

An earbud includes a speaker driver, and a sensor module secured to the speaker driver that is configured to detect and/or measure physiological information from a subject wearing the earbud. The sensor module includes a printed circuit board, an optical source secured to the printed circuit board, and an optical detector secured to the printed circuit board. A first light guide may be coupled to the optical source that is configured to deliver light from the optical source into an ear region of the subject via a distal end thereof. A second light guide may be coupled to the optical detector that is configured to collect light from the ear region via a distal end thereof and deliver collected light to the optical detector. One or more additional sensors may be secured to the speaker driver, such as accelerometers, humidity sensors, altimeters, and temperature sensors.

13 Claims, 39 Drawing Sheets

Related U.S. Application Data

(60) Provisional application No. 62/033,922, filed on Aug. 6, 2014.

(51) Int. Cl.
  *A61B 5/00* (2006.01)
  *A61B 5/026* (2006.01)
  *A61B 5/1455* (2006.01)

(52) U.S. Cl.
  CPC .......... *A61B 5/6802* (2013.01); *A61B 5/6803* (2013.01); *A61B 5/721* (2013.01); *H04R 1/1016* (2013.01)

(56) References Cited

U.S. PATENT DOCUMENTS

| | | |
|---|---|---|
| 4,331,154 A | 5/1982 | Broadwater et al. |
| 4,438,772 A | 3/1984 | Slavin |
| 4,491,760 A | 1/1985 | Linvill |
| 4,521,499 A | 6/1985 | Switzer |
| 4,541,905 A | 9/1985 | Kuwana et al. |
| 4,592,807 A | 6/1986 | Switzer |
| 4,655,225 A | 4/1987 | Dahne et al. |
| 4,830,014 A | 5/1989 | Goodman et al. |
| 4,882,492 A | 11/1989 | Schlager |
| 4,896,676 A | 1/1990 | Sasaki |
| 4,928,704 A | 5/1990 | Hardt |
| 4,957,109 A | 9/1990 | Groeger et al. |
| 5,002,060 A | 3/1991 | Nedivi |
| 5,022,970 A | 6/1991 | Cook et al. |
| 5,025,791 A | 6/1991 | Niwa |
| 5,079,421 A | 1/1992 | Knudson et al. |
| 5,080,098 A | 1/1992 | Willett et al. |
| 5,086,229 A | 2/1992 | Rosenthal et al. |
| 5,143,078 A | 9/1992 | Mather et al. |
| 5,226,417 A | 7/1993 | Swedlow et al. |
| 5,237,994 A | 8/1993 | Goldberger |
| 5,348,002 A | 9/1994 | Caro |
| 5,377,100 A | 12/1994 | Pope et al. |
| 5,482,036 A | 1/1996 | Diab et al. |
| 5,492,129 A | 2/1996 | Greenberger |
| 5,499,301 A | 3/1996 | Sudo et al. |
| 5,581,648 A | 12/1996 | Sahagen |
| 5,596,987 A | 1/1997 | Chance |
| 5,662,117 A | 9/1997 | Bittman |
| 5,673,692 A | 10/1997 | Schulze et al. |
| 5,697,374 A | 12/1997 | Odagiri et al. |
| 5,711,308 A | 1/1998 | Singer |
| 5,725,480 A | 3/1998 | Oosta et al. |
| 5,743,260 A | 4/1998 | Chung et al. |
| 5,779,631 A | 7/1998 | Chance |
| 5,797,841 A | 8/1998 | Delonzor et al. |
| 5,807,114 A | 9/1998 | Hodges et al. |
| 5,807,267 A | 9/1998 | Bryars et al. |
| 5,853,005 A | 12/1998 | Scanlon |
| 5,904,654 A | 5/1999 | Wohltmann et al. |
| 5,938,593 A | 8/1999 | Quellette |
| 5,964,701 A | 10/1999 | Asada et al. |
| 5,971,931 A | 10/1999 | Raff |
| 5,974,338 A | 10/1999 | Asano et al. |
| 5,995,858 A | 11/1999 | Kinast |
| 6,004,274 A | 12/1999 | Nolan et al. |
| 6,013,007 A | 1/2000 | Root et al. |
| 6,023,541 A | 2/2000 | Merchant et al. |
| 6,030,342 A | 2/2000 | Amano et al. |
| 6,045,511 A | 4/2000 | Ott et al. |
| 6,067,006 A | 5/2000 | O'Brien |
| 6,070,093 A | 5/2000 | Oosta et al. |
| 6,078,829 A | 6/2000 | Uchida et al. |
| 6,080,110 A | 6/2000 | Thorgersen |
| 6,081,742 A | 6/2000 | Amano et al. |
| 6,186,145 B1 | 2/2001 | Brown |
| 6,198,394 B1 | 3/2001 | Jacobsen et al. |
| 6,198,951 B1 | 3/2001 | Kosuda et al. |
| 6,205,354 B1 | 3/2001 | Gellermann et al. |
| 6,231,519 B1 | 5/2001 | Blants et al. |
| 6,283,915 B1 | 9/2001 | Aceti et al. |
| 6,285,816 B1 | 9/2001 | Anderson et al. |
| 6,289,230 B1 | 9/2001 | Chaiken et al. |
| 6,298,314 B1 | 10/2001 | Blackadar et al. |
| 6,332,868 B1 | 12/2001 | Sato et al. |
| 6,358,216 B1 | 3/2002 | Kraus et al. |
| 6,361,660 B1 | 3/2002 | Goldstein |
| 6,371,925 B1 | 4/2002 | Imai et al. |
| 6,374,129 B1 | 4/2002 | Chin et al. |
| 6,415,167 B1 | 7/2002 | Blank et al. |
| 6,443,890 B1 | 9/2002 | Schulze et al. |
| 6,444,474 B1 | 9/2002 | Thomas et al. |
| 6,454,718 B1 | 9/2002 | Clift |
| 6,458,080 B1 | 10/2002 | Brown et al. |
| 6,470,893 B1 | 10/2002 | Boesen |
| 6,513,532 B2 | 2/2003 | Mault et al. |
| 6,514,278 B1 | 2/2003 | Hibst et al. |
| 6,527,711 B1 | 3/2003 | Stivoric et al. |
| 6,527,712 B1 | 3/2003 | Brown et al. |
| 6,529,754 B2 | 3/2003 | Kondo |
| 6,534,012 B1 | 3/2003 | Hazen et al. |
| 6,556,852 B1 | 4/2003 | Schulze et al. |
| 6,569,094 B2 | 5/2003 | Suzuki et al. |
| 6,571,117 B1 | 5/2003 | Marbach |
| 6,605,038 B1 | 8/2003 | Teller et al. |
| 6,616,613 B1 | 9/2003 | Goodman |
| 6,631,196 B1 | 10/2003 | Taenzer et al. |
| 6,647,378 B2 | 11/2003 | Kindo |
| 6,656,116 B2 | 12/2003 | Kim et al. |
| 6,694,180 B1 | 2/2004 | Boesen |
| 6,745,061 B1 | 6/2004 | Hicks et al. |
| 6,748,254 B2 | 6/2004 | O'Neil et al. |
| 6,760,610 B2 | 7/2004 | Tschupp et al. |
| 6,783,501 B2 | 8/2004 | Takahashi et al. |
| 6,808,473 B2 | 10/2004 | Hisano et al. |
| 6,859,658 B1 | 2/2005 | Krug |
| 6,893,396 B2 | 5/2005 | Schulze et al. |
| 6,941,239 B2 | 9/2005 | Unuma et al. |
| 6,953,435 B2 | 10/2005 | Kondo et al. |
| 6,996,427 B2 | 2/2006 | Ali et al. |
| 6,997,879 B1 | 2/2006 | Turcott |
| 7,018,338 B2 | 3/2006 | Vetter et al. |
| 7,024,369 B1 | 4/2006 | Brown et al. |
| 7,030,359 B2 | 4/2006 | Römhild |
| 7,034,694 B2 | 4/2006 | Yamaguchi et al. |
| 7,039,454 B1 | 5/2006 | Kaga et al. |
| 7,041,062 B2 | 5/2006 | Friedrichs et al. |
| 7,043,287 B1 | 5/2006 | Khalil et al. |
| 7,054,674 B2 | 5/2006 | Cane et al. |
| 7,088,234 B2 | 8/2006 | Naito et al. |
| 7,107,088 B2 | 9/2006 | Aceti |
| 7,113,815 B2 | 9/2006 | O'Neil et al. |
| 7,117,032 B2 | 10/2006 | Childre et al. |
| 7,163,512 B1 | 1/2007 | Childre et al. |
| 7,175,601 B2 | 2/2007 | Verjus et al. |
| 7,209,775 B2 | 4/2007 | Bae et al. |
| 7,217,224 B2 | 5/2007 | Thomas |
| 7,252,639 B2 | 8/2007 | Kimura et al. |
| 7,263,396 B2 | 8/2007 | Chen et al. |
| 7,289,837 B2 | 10/2007 | Mannheimer et al. |
| 7,336,982 B2 | 2/2008 | Yoo et al. |
| 7,341,559 B2 | 3/2008 | Schulz et al. |
| 7,376,451 B2 | 5/2008 | Mahony et al. |
| 7,470,234 B1 | 12/2008 | Elhag et al. |
| 7,483,730 B2 | 1/2009 | Diab et al. |
| 7,486,988 B2 | 2/2009 | Goodall et al. |
| 7,507,207 B2 | 3/2009 | Sakai et al. |
| 7,519,327 B2 | 4/2009 | White |
| 7,526,327 B2 | 4/2009 | Blondeau et al. |
| 7,583,994 B2 | 9/2009 | Scholz |
| 7,620,450 B2 | 11/2009 | Kim et al. |
| 7,625,285 B2 | 12/2009 | Breving |
| 7,652,569 B2 | 1/2010 | Kiff et al. |
| 7,689,437 B1 | 3/2010 | Teller et al. |
| 7,695,440 B2 | 4/2010 | Kondo et al. |
| 7,725,147 B2 | 5/2010 | Li et al. |
| 7,756,559 B2 | 7/2010 | Abreu |
| 7,843,325 B2 | 11/2010 | Otto |

(56) References Cited

U.S. PATENT DOCUMENTS

| | | |
|---|---|---|
| 7,894,869 B2 | 2/2011 | Hoarau |
| 7,914,468 B2 | 3/2011 | Shalon et al. |
| 7,991,448 B2 | 8/2011 | Edgar et al. |
| 7,998,079 B2 | 8/2011 | Nagai et al. |
| 8,050,728 B2 | 11/2011 | Al-Ali et al. |
| 8,055,319 B2 | 11/2011 | Oh et al. |
| 8,055,330 B2 | 11/2011 | Egozi |
| 8,059,924 B1 | 11/2011 | Letant et al. |
| 8,130,105 B2 | 3/2012 | Al-Ali et al. |
| 8,137,270 B2 | 3/2012 | Keenan et al. |
| 8,157,730 B2 | 4/2012 | LaBoeuf et al. |
| 8,172,459 B2 | 5/2012 | Abreu |
| 8,175,670 B2 | 5/2012 | Baker, Jr. et al. |
| 8,204,730 B2 | 6/2012 | Liu et al. |
| 8,204,786 B2 | 6/2012 | LeBoeuf et al. |
| 8,233,955 B2 | 7/2012 | Al-Ali et al. |
| 8,251,903 B2 | 8/2012 | LeBoeuf et al. |
| 8,255,027 B2 | 8/2012 | Al-Ali et al. |
| 8,255,029 B2 | 8/2012 | Addison et al. |
| 8,303,512 B2 | 11/2012 | Kosuda et al. |
| 8,320,982 B2 | 11/2012 | LeBoeuf et al. |
| 8,323,982 B2 | 12/2012 | LeBoeuf et al. |
| 8,328,420 B2 | 12/2012 | Abreu |
| 8,416,959 B2 | 4/2013 | Lott et al. |
| 8,491,492 B2 | 7/2013 | Shinar et al. |
| 8,504,679 B2 | 8/2013 | Spire et al. |
| 8,506,524 B2 | 8/2013 | Graskov et al. |
| 8,512,242 B2 | 8/2013 | LeBoeuf et al. |
| 8,647,270 B2 | 2/2014 | LeBoeuf et al. |
| 8,652,040 B2 | 2/2014 | LeBoeuf et al. |
| 8,652,409 B2 | 2/2014 | LeBoeuf et al. |
| 8,679,008 B2 | 3/2014 | Hughes et al. |
| 8,700,111 B2 | 4/2014 | LeBoeuf et al. |
| 8,702,607 B2 | 4/2014 | LeBoeuf et al. |
| 8,730,048 B2 | 5/2014 | Shen et al. |
| 8,788,002 B2 | 7/2014 | LeBoeuf et al. |
| 8,886,269 B2 | 11/2014 | LeBoeuf et al. |
| 8,888,701 B2 * | 11/2014 | LeBoeuf ............ G06F 19/3406 600/301 |
| 8,923,941 B2 | 12/2014 | LeBoeuf et al. |
| 8,929,965 B2 | 1/2015 | LeBoeuf et al. |
| 8,929,966 B2 | 1/2015 | LeBoeuf et al. |
| 8,934,952 B2 | 1/2015 | LeBoeuf et al. |
| 8,942,776 B2 | 1/2015 | LeBoeuf et al. |
| 8,961,415 B2 | 2/2015 | LeBoeuf et al. |
| 9,005,129 B2 | 4/2015 | Venkatraman |
| 2001/0049471 A1 | 12/2001 | Suzuki et al. |
| 2002/0035340 A1 | 3/2002 | Fraden et al. |
| 2002/0143242 A1 | 10/2002 | Nemirovski |
| 2002/0156386 A1 | 10/2002 | Dardik et al. |
| 2002/0156654 A1 | 10/2002 | Roe et al. |
| 2002/0186137 A1 | 12/2002 | Skardon |
| 2002/0188210 A1 | 12/2002 | Aizawa |
| 2002/0194002 A1 | 12/2002 | Petrushin |
| 2003/0002705 A1 | 1/2003 | Boesen |
| 2003/0007631 A1 | 1/2003 | Bolognesi et al. |
| 2003/0045785 A1 | 3/2003 | Diab et al. |
| 2003/0050563 A1 | 3/2003 | Suribhotla et al. |
| 2003/0064712 A1 | 4/2003 | Gaston et al. |
| 2003/0065257 A1 | 4/2003 | Mault et al. |
| 2003/0083583 A1 | 5/2003 | Kovtun et al. |
| 2003/0109030 A1 | 6/2003 | Uchida et al. |
| 2003/0181795 A1 | 9/2003 | Suzuki et al. |
| 2003/0212336 A1 | 11/2003 | Lee et al. |
| 2003/0220584 A1 | 11/2003 | Honeyager et al. |
| 2003/0222268 A1 | 12/2003 | Yocom et al. |
| 2004/0004547 A1 | 1/2004 | Appelt et al. |
| 2004/0022700 A1 | 2/2004 | Kim et al. |
| 2004/0030581 A1 | 2/2004 | Leven |
| 2004/0034289 A1 | 2/2004 | Teller et al. |
| 2004/0034293 A1 | 2/2004 | Kimball |
| 2004/0054291 A1 | 3/2004 | Schulz et al. |
| 2004/0075677 A1 | 4/2004 | Loyall et al. |
| 2004/0077934 A1 | 4/2004 | Massad |
| 2004/0082842 A1 | 4/2004 | Lumba et al. |
| 2004/0103146 A1 | 5/2004 | Park |
| 2004/0117204 A1 | 6/2004 | Mazar et al. |
| 2004/0120844 A1 | 6/2004 | Tribelsky et al. |
| 2004/0122294 A1 | 6/2004 | Hatlestad et al. |
| 2004/0122702 A1 | 6/2004 | Sabol et al. |
| 2004/0133123 A1 | 7/2004 | Leonhardt et al. |
| 2004/0135571 A1 | 7/2004 | Uutela et al. |
| 2004/0138578 A1 | 7/2004 | Pineda et al. |
| 2004/0186390 A1 | 9/2004 | Ross et al. |
| 2004/0219056 A1 | 11/2004 | Tribelsky et al. |
| 2004/0220488 A1 | 11/2004 | Vyshedskiy et al. |
| 2004/0225207 A1 | 11/2004 | Bae et al. |
| 2004/0228494 A1 | 11/2004 | Smith |
| 2004/0242976 A1 | 12/2004 | Abreu |
| 2005/0004458 A1 | 1/2005 | Kanayama et al. |
| 2005/0027216 A1 | 2/2005 | Guillemaud et al. |
| 2005/0030540 A1 | 2/2005 | Thornton |
| 2005/0033200 A1 | 2/2005 | Soehren et al. |
| 2005/0038349 A1 | 2/2005 | Choi et al. |
| 2005/0043600 A1 | 2/2005 | Diab et al. |
| 2005/0043630 A1 | 2/2005 | Buchert et al. |
| 2005/0058456 A1 | 3/2005 | Yoo |
| 2005/0059870 A1 | 3/2005 | Aceti |
| 2005/0070809 A1 | 3/2005 | Acres |
| 2005/0084666 A1 | 4/2005 | Pong et al. |
| 2005/0101845 A1 | 5/2005 | Nihtila |
| 2005/0101872 A1 | 5/2005 | Sattler et al. |
| 2005/0113167 A1 | 5/2005 | Buchner et al. |
| 2005/0113656 A1 | 5/2005 | Chance |
| 2005/0113703 A1 | 5/2005 | Farringdon et al. |
| 2005/0116820 A1 | 6/2005 | Goldreich |
| 2005/0119833 A1 | 6/2005 | Nanikashvili |
| 2005/0148883 A1 | 7/2005 | Boesen |
| 2005/0154264 A1 | 7/2005 | Lecompte et al. |
| 2005/0177034 A1 | 8/2005 | Beaumont |
| 2005/0187448 A1 | 8/2005 | Petersen et al. |
| 2005/0187453 A1 | 8/2005 | Petersen et al. |
| 2005/0192515 A1 | 9/2005 | Givens et al. |
| 2005/0196009 A1 | 9/2005 | Boesen |
| 2005/0203349 A1 | 9/2005 | Nanikashvili |
| 2005/0203357 A1 | 9/2005 | Debreczeny et al. |
| 2005/0209516 A1 | 9/2005 | Fraden |
| 2005/0222487 A1 | 10/2005 | Miller et al. |
| 2005/0222903 A1 | 10/2005 | Buchheit et al. |
| 2005/0228244 A1 | 10/2005 | Banet |
| 2005/0228299 A1 | 10/2005 | Banet |
| 2005/0240087 A1 | 10/2005 | Keenan et al. |
| 2005/0258816 A1 | 11/2005 | Zen et al. |
| 2005/0259811 A1 | 11/2005 | Kimm et al. |
| 2006/0009685 A1 | 1/2006 | Finarov et al. |
| 2006/0012567 A1 | 1/2006 | Sicklinger |
| 2006/0063993 A1 | 3/2006 | Yu et al. |
| 2006/0064037 A1 | 3/2006 | Shalon et al. |
| 2006/0084878 A1 | 4/2006 | Banet et al. |
| 2006/0084879 A1 | 4/2006 | Nazarian et al. |
| 2006/0122520 A1 | 6/2006 | Banet et al. |
| 2006/0123885 A1 | 6/2006 | Yates et al. |
| 2006/0140425 A1 | 6/2006 | Berg et al. |
| 2006/0142665 A1 | 6/2006 | Garay et al. |
| 2006/0202816 A1 | 9/2006 | Crump et al. |
| 2006/0205083 A1 | 9/2006 | Zhao |
| 2006/0210058 A1 | 9/2006 | Kock et al. |
| 2006/0211922 A1 | 9/2006 | Al-Ali et al. |
| 2006/0211924 A1 | 9/2006 | Dalke et al. |
| 2006/0217598 A1 | 9/2006 | Miyajima et al. |
| 2006/0224059 A1 | 10/2006 | Swedlow et al. |
| 2006/0240558 A1 | 10/2006 | Zhao |
| 2006/0246342 A1 | 11/2006 | MacPhee |
| 2006/0251277 A1 | 11/2006 | Cho |
| 2006/0251334 A1 | 11/2006 | Oba et al. |
| 2006/0252999 A1 | 11/2006 | Devaul et al. |
| 2006/0264730 A1 | 11/2006 | Stivoric et al. |
| 2006/0292533 A1 | 12/2006 | Selod |
| 2006/0293921 A1 | 12/2006 | McCarthy et al. |
| 2007/0004449 A1 | 1/2007 | Sham |
| 2007/0004969 A1 | 1/2007 | Kong et al. |
| 2007/0015992 A1 | 1/2007 | Filkins et al. |
| 2007/0021206 A1 | 1/2007 | Sunnen |
| 2007/0027367 A1 | 2/2007 | Oliver et al. |

(56) References Cited

U.S. PATENT DOCUMENTS

| | | |
|---|---|---|
| 2007/0027399 A1 | 2/2007 | Chou |
| 2007/0036383 A1 | 2/2007 | Romero |
| 2007/0050215 A1 | 3/2007 | Kil et al. |
| 2007/0060800 A1 | 3/2007 | Drinan et al. |
| 2007/0060819 A1 | 3/2007 | Altshuler et al. |
| 2007/0063850 A1 | 3/2007 | Devaul et al. |
| 2007/0082789 A1 | 4/2007 | Nissila et al. |
| 2007/0083092 A1 | 4/2007 | Rippo et al. |
| 2007/0083095 A1 | 4/2007 | Rippo et al. |
| 2007/0088221 A1 | 4/2007 | Stahmann |
| 2007/0093702 A1 | 4/2007 | Yu et al. |
| 2007/0106167 A1 | 5/2007 | Kinast |
| 2007/0112273 A1 | 5/2007 | Rogers |
| 2007/0112598 A1 | 5/2007 | Heckerman et al. |
| 2007/0116314 A1 | 5/2007 | Grilliot et al. |
| 2007/0118043 A1 | 5/2007 | Oliver et al. |
| 2007/0165872 A1 | 7/2007 | Bridger et al. |
| 2007/0167850 A1 | 7/2007 | Russell et al. |
| 2007/0191718 A1 | 8/2007 | Nakamura |
| 2007/0197878 A1 | 8/2007 | Shklarski |
| 2007/0197881 A1 | 8/2007 | Wolf et al. |
| 2007/0213020 A1 | 9/2007 | Novac |
| 2007/0230714 A1 | 10/2007 | Armstrong |
| 2007/0233403 A1 | 10/2007 | Alwan et al. |
| 2007/0265097 A1 | 11/2007 | Havukainen |
| 2007/0270667 A1 | 11/2007 | Coppi et al. |
| 2007/0270671 A1 | 11/2007 | Gal |
| 2007/0293781 A1 | 12/2007 | Sims et al. |
| 2007/0299330 A1 | 12/2007 | Couronne et al. |
| 2008/0004536 A1 | 1/2008 | Baxi et al. |
| 2008/0015424 A1 | 1/2008 | Bernreuter |
| 2008/0039731 A1 | 2/2008 | McCombie et al. |
| 2008/0076972 A1 | 3/2008 | Dorogusker et al. |
| 2008/0081963 A1 | 4/2008 | Naghavi et al. |
| 2008/0086533 A1 | 4/2008 | Neuhauser et al. |
| 2008/0096726 A1 | 4/2008 | Riley et al. |
| 2008/0114220 A1 | 5/2008 | Banet et al. |
| 2008/0132798 A1 | 6/2008 | Hong et al. |
| 2008/0141301 A1 | 6/2008 | Azzaro et al. |
| 2008/0146890 A1 | 6/2008 | LeBoeuf et al. |
| 2008/0154098 A1 | 6/2008 | Morris et al. |
| 2008/0154105 A1 | 6/2008 | Lemay |
| 2008/0165017 A1 | 7/2008 | Schwartz |
| 2008/0170600 A1 | 7/2008 | Sattler et al. |
| 2008/0171945 A1 | 7/2008 | Dotter |
| 2008/0177162 A1 | 7/2008 | Bae et al. |
| 2008/0200774 A1 | 8/2008 | Luo |
| 2008/0203144 A1 | 8/2008 | Kim |
| 2008/0221461 A1 | 9/2008 | Zhou et al. |
| 2008/0249594 A1 | 10/2008 | Dietrich |
| 2008/0287752 A1 | 11/2008 | Stroetz et al. |
| 2009/0005662 A1 | 1/2009 | Petersen et al. |
| 2009/0006457 A1 | 1/2009 | Stivoric et al. |
| 2009/0010461 A1 | 1/2009 | Klinghult et al. |
| 2009/0030350 A1 | 1/2009 | Yang et al. |
| 2009/0054751 A1 | 2/2009 | Babashan et al. |
| 2009/0054752 A1 | 2/2009 | Jonnalagadda et al. |
| 2009/0069645 A1 | 3/2009 | Nielsen et al. |
| 2009/0082994 A1 | 3/2009 | Schuler et al. |
| 2009/0088611 A1 | 4/2009 | Buschmann |
| 2009/0093687 A1 | 4/2009 | Telfort et al. |
| 2009/0105548 A1 | 4/2009 | Bart |
| 2009/0105556 A1 | 4/2009 | Fricke et al. |
| 2009/0131761 A1 | 5/2009 | Moroney, III et al. |
| 2009/0131764 A1 | 5/2009 | Lee et al. |
| 2009/0175456 A1 | 7/2009 | Johnson |
| 2009/0177097 A1 | 7/2009 | Ma et al. |
| 2009/0214060 A1 | 8/2009 | Chuang et al. |
| 2009/0221888 A1 | 9/2009 | Wijesiriwardana |
| 2009/0227853 A1 | 9/2009 | Wijesiriwardana |
| 2009/0240125 A1 | 9/2009 | Such et al. |
| 2009/0253992 A1 | 10/2009 | Van Der Loo |
| 2009/0253996 A1 | 10/2009 | Lee et al. |
| 2009/0264711 A1 | 10/2009 | Schuler et al. |
| 2009/0270698 A1 | 10/2009 | Shioi et al. |
| 2009/0287067 A1 | 11/2009 | Dorogusker et al. |
| 2009/0299215 A1 | 12/2009 | Zhang |
| 2010/0004517 A1 | 1/2010 | Bryenton et al. |
| 2010/0022861 A1 | 1/2010 | Cinbis et al. |
| 2010/0045663 A1 | 2/2010 | Chen et al. |
| 2010/0100013 A1 | 4/2010 | Hu et al. |
| 2010/0113948 A1 | 5/2010 | Yang et al. |
| 2010/0168531 A1 | 7/2010 | Shaltis et al. |
| 2010/0172522 A1 | 7/2010 | Mooring et al. |
| 2010/0179389 A1 | 7/2010 | Moroney et al. |
| 2010/0185105 A1 | 7/2010 | Baldinger |
| 2010/0217100 A1 | 8/2010 | LeBoeuf |
| 2010/0217103 A1 | 8/2010 | Abdul-Hafiz et al. |
| 2010/0222655 A1 | 9/2010 | Starr et al. |
| 2010/0228315 A1 | 9/2010 | Nielsen |
| 2010/0234714 A1 | 9/2010 | Mercier et al. |
| 2010/0268056 A1 | 10/2010 | Picard et al. |
| 2010/0274100 A1 | 10/2010 | Behar et al. |
| 2010/0274109 A1 | 10/2010 | Hu et al. |
| 2010/0292589 A1 | 11/2010 | Goodman |
| 2010/0298653 A1 | 11/2010 | McCombie et al. |
| 2011/0028810 A1 | 2/2011 | Van Slyke et al. |
| 2011/0028813 A1 | 2/2011 | Watson et al. |
| 2011/0081037 A1 | 4/2011 | Oh et al. |
| 2011/0098112 A1 | 4/2011 | LeBoeuf |
| 2011/0105869 A1 | 5/2011 | Wilson et al. |
| 2011/0112382 A1 | 5/2011 | Li et al. |
| 2011/0130638 A1 | 6/2011 | Raridan, Jr. |
| 2011/0142371 A1 | 6/2011 | King et al. |
| 2011/0288379 A1 | 11/2011 | Wu |
| 2012/0030547 A1 | 2/2012 | Raptis et al. |
| 2012/0095303 A1 | 4/2012 | He |
| 2012/0150052 A1 | 6/2012 | Buchheim et al. |
| 2012/0156933 A1 | 6/2012 | Kreger et al. |
| 2012/0179011 A1 | 7/2012 | Moon et al. |
| 2012/0203081 A1 | 8/2012 | LeBoeuf et al. |
| 2012/0226111 A1 | 9/2012 | LeBoeuf et al. |
| 2012/0226112 A1 | 9/2012 | LeBoeuf et al. |
| 2012/0277548 A1 | 11/2012 | Burton |
| 2012/0283577 A1 | 11/2012 | LeBoeuf et al. |
| 2012/0296184 A1 | 11/2012 | LeBoeuf et al. |
| 2013/0053661 A1 | 2/2013 | Alberth et al. |
| 2013/0072765 A1 | 3/2013 | Kahn et al. |
| 2013/0131519 A1 | 5/2013 | LeBoeuf et al. |
| 2013/0245387 A1 | 9/2013 | Patel |
| 2013/0336495 A1 | 12/2013 | Burgett et al. |
| 2014/0012105 A1 | 1/2014 | LeBoeuf et al. |
| 2014/0051940 A1 | 2/2014 | Messerschmidt |
| 2014/0051948 A1 | 2/2014 | LeBoeuf et al. |
| 2014/0052567 A1 | 2/2014 | Bhardwaj et al. |
| 2014/0058220 A1 | 2/2014 | LeBoeuf et al. |
| 2014/0073486 A1 | 3/2014 | Ahmed et al. |
| 2014/0088433 A1 | 3/2014 | Shan |
| 2014/0094663 A1 | 4/2014 | LeBoeuf et al. |
| 2014/0100432 A1 | 4/2014 | Golda et al. |
| 2014/0114147 A1 | 4/2014 | Romesburg et al. |
| 2014/0127996 A1 | 5/2014 | Park et al. |
| 2014/0128690 A1 | 5/2014 | LeBoeuf et al. |
| 2014/0135596 A1 | 5/2014 | LeBoeuf et al. |
| 2014/0140567 A1 | 5/2014 | LeBoeuf et al. |
| 2014/0180039 A1 | 6/2014 | LeBoeuf et al. |
| 2014/0211959 A1* | 7/2014 | Boyajian ............ H04R 1/1041 381/74 |
| 2014/0219467 A1 | 8/2014 | Kurtz |
| 2014/0235967 A1 | 8/2014 | LeBoeuf et al. |
| 2014/0235968 A1 | 8/2014 | LeBoeuf et al. |
| 2014/0236531 A1 | 8/2014 | Carter |
| 2014/0243617 A1 | 8/2014 | LeBoeuf et al. |
| 2014/0243620 A1 | 8/2014 | LeBoeuf et al. |
| 2014/0275852 A1 | 9/2014 | Hong et al. |
| 2014/0275855 A1 | 9/2014 | LeBoeuf et al. |
| 2014/0287833 A1 | 9/2014 | LeBoeuf et al. |
| 2014/0288396 A1 | 9/2014 | LeBoeuf et al. |
| 2014/0288436 A1 | 9/2014 | Venkatraman et al. |
| 2014/0323829 A1 | 10/2014 | LeBoeuf et al. |
| 2014/0323830 A1 | 10/2014 | LeBoeuf et al. |
| 2014/0323880 A1 | 10/2014 | Ahmed et al. |
| 2014/0378844 A1 | 12/2014 | Fei |
| 2015/0011898 A1 | 1/2015 | Romesburg |

(56) References Cited

U.S. PATENT DOCUMENTS

| | | |
|---|---|---|
| 2015/0018636 A1 | 1/2015 | Romesburg |
| 2015/0031967 A1 | 1/2015 | LeBoeuf et al. |
| 2015/0032009 A1 | 1/2015 | LeBoeuf et al. |
| 2015/0057967 A1 | 2/2015 | Albinali |
| 2015/0190085 A1 | 7/2015 | Nathan et al. |
| 2015/0250396 A1 | 9/2015 | Ahmed et al. |
| 2015/0265217 A1 | 9/2015 | Penders et al. |
| 2015/0289820 A1 | 10/2015 | Miller et al. |
| 2015/0342481 A1 | 12/2015 | Liu et al. |
| 2015/0366509 A1 | 12/2015 | Romesburg |
| 2016/0022220 A1 | 1/2016 | Lee et al. |
| 2016/0029964 A1 | 2/2016 | LeBoeuf et al. |
| 2016/0094899 A1 | 3/2016 | Aumer et al. |
| 2016/0287108 A1 | 10/2016 | Wei et al. |
| 2017/0034615 A1 | 2/2017 | Mankodi et al. |

FOREIGN PATENT DOCUMENTS

| | | |
|---|---|---|
| DE | 3910749 A1 | 10/1990 |
| EP | 1 297 784 A1 | 4/2003 |
| EP | 1 480 278 A2 | 11/2004 |
| EP | 2 077 091 A2 | 7/2009 |
| EP | 2 182 839 B1 | 10/2011 |
| GB | 2 408 209 A | 5/2005 |
| GB | 2 411 719 A | 9/2005 |
| JP | 7-241279 | 9/1995 |
| JP | 9-253062 | 9/1997 |
| JP | 9-299342 | 11/1997 |
| JP | 2000-116611 | 4/2000 |
| JP | 2001-025462 | 1/2001 |
| JP | 2003-159221 | 6/2003 |
| JP | 2004-513750 A | 5/2004 |
| JP | 2004-283523 | 10/2004 |
| JP | 2007-044203 | 2/2007 |
| JP | 2007-185348 | 7/2007 |
| JP | 2008-136556 A | 6/2008 |
| JP | 2008-279061 A | 11/2008 |
| JP | 2009-153664 A | 7/2009 |
| JP | 2010-526646 | 8/2010 |
| JP | 2014-068733 A | 4/2014 |
| KR | 20-0204510 Y1 | 11/2000 |
| WO | WO 00/24064 | 4/2000 |
| WO | WO 00/047108 A1 | 8/2000 |
| WO | WO 01/08552 A1 | 2/2001 |
| WO | WO 2002/017782 A2 | 3/2002 |
| WO | WO 2005/010568 A2 | 2/2005 |
| WO | WO 2005/020121 A1 | 3/2005 |
| WO | WO 2005/110238 A1 | 11/2005 |
| WO | WO 2006/009830 A2 | 1/2006 |
| WO | WO 2006/067690 A2 | 6/2006 |
| WO | WO 2007/012931 A2 | 2/2007 |
| WO | WO 2007/023426 A2 | 3/2007 |
| WO | WO 2007/038432 A2 | 4/2007 |
| WO | WO 2007/053146 A1 | 5/2007 |
| WO | WO 2008/141306 A2 | 11/2008 |
| WO | WO 2011/127063 A1 | 10/2011 |
| WO | WO 2013/019494 A2 | 2/2013 |
| WO | WO 2013/038296 A1 | 3/2013 |
| WO | WO 2013/109389 A1 | 7/2013 |
| WO | WO 2013/109390 A1 | 7/2013 |
| WO | WO 2014/092932 A1 | 6/2014 |
| WO | WO 2014/116924 A1 | 7/2014 |
| WO | WO 2015/128226 A1 | 9/2015 |

OTHER PUBLICATIONS

International Search Report and Written Opinion of the International Searching Authority, PCT/US2015/041562, dated Oct. 28, 2015, 20 pages.

"U.S. Army Fitness Training Handbook" by the Department of the Army, 2003, The Lyons Press, p. 17.

"Warfighter Physiological and Environmental Monitoring: A Study for the U.S. Army Research Institute in Environmental Medicine and the Soldier Systems Center", Massachusetts Institute of Technology Lincoln Laboratory, Final Report, Nov. 1, 2004, prepared for the U.S. Army under Air Force Contract F19628-00-C-0002; approved for public release.

Anpo et al. "Photocatalytic Reduction of $CO_2$ With $H_2O$ on Titanium Oxides Anchored within Micropores of Zeolites: Effects of the Structure of the Active Sites and the Addition of Pt" *J. Phys. Chem. B*, 101:2632-2636 (1997).

Asada et al, "Monitoring with Wearable Photoplethysmographic Biosensors," IEEE Engineering in Medicine and Biology Magazine, May/Jun. 2003, pp. 28-40.

Bårsan et al. "Understanding the fundamental principles of metal oxide based gas sensors; the example of CO sensing with $SnO_2$ sensors in the presence of humidity" *Journal of Physics: Condensed Matter* 15:R813-R839 (2003).

Bifulco et al., "Bluetooth Portable Device for Continuous ECG and Patient Motion Monitoring During Daily Life," Medicon 2007, IFMBE Proceedings 16, 2007, pp. 369-372.

Bott "Electrochemistry of Semiconductors" *Current Separations* 17(3):87-91 (1998).

Brodersen et al., "In-Ear Acquisition of Vital Signs Discloses New Chances for Preventive Continuous Cardiovascular Monitoring," 4th International Workshop on Wearable and Implantable Body Sensor Networks (BSN 2007), vol. 13 of the series IFMBE Proceedings, pp. 189-194.

Celka et al, "Motion Resistant Earphone Located Infrared based Heart Rate Measurement Device," Proceedings of the Second IASTED International Conference on Biomedical Engineering, Feb. 16-18, 2004, Innsbruck, Austria, pp. 582-585.

Colligan, M. J. et al. in "The psychological effects of indoor air pollution", Bulletin of the New York Academy of Medicine, vol. 57, No. 10, Dec. 1981, p. 1014-1026.

Communication pursuant to Article 94(3) EPC, European Application No. 12 739 502.8, dated Nov. 30, 2016, 6 pages.

Communication Pursuant to Article 94(3) EPC, EP 12 739 502.8, dated Jul. 19, 2016, 7 pages.

Communication pursuant to Article 94(3) EPC, EP 12 820 308.0, dated Feb. 3, 2016, 5 pages.

Communication pursuant to Article 94(3) EPC, EP 13 863 449.8, dated Nov. 5, 2015, 7 pages.

Communication pursuant to Article 94(3) EPC, EP 14 743 615.8, dated Dec. 23, 2015, 7 pages.

Communication Pursuant to Article 94(3) EPC, EP 14 743 615.8, dated Jul. 19, 2016, 7 pages.

Communication pursuant to Article 94(3) EPC, EP 14 743 839.4, dated Dec. 23, 2015, 6 pages.

Communication Pursuant to Article 94(3) EPC, EP 14 743 839.4, dated Jul. 20, 2016, 5 pages.

Comtois et al., "A Wearable Wireless Reflectance Pulse Oximeter for Remote Triage Applications," 2006 IEEE, pp. 53-54.

Comtois, Gary, W., "Implementation of Accelerometer-Based Adaptive Noise Cancellation in a Wireless Wearable Pulse Oximeter Platform for Remote Physiological Monitoring and Triage," Thesis, Worcester Polytechnic Institute, Aug. 31, 2007, 149 pages.

de Paula Santos, U. et al, in "Effects of air pollution on blood pressure and heart rate variability: a panel study of vehicular traffic controllers in the city of Sao Paulo, Brazil", European Heart Journal (2005) 26, 193-200.

Duun et al., "A Novel Ring Shaped Photodiode for Reflectance Pulse Oximetry in Wireless Applications," IEEE Sensors 2007 Conference, pp. 596-599.

Ebert, T et al., "Influence of Hydration Status on Thermoregulation and Cycling Hill Climbing," Med. Sci. Sport Exerc. vol. 39, No. 2, pp. 323-329, 2007.

Edmison et al., "E-Textile Based Automatic Activity Diary for Medical Annotation and Analysis," Proc. BSN 2006 Int. Workshop Wearable Implantable Body Sensor Netw. (2006), pp. 131-145, Apr. 3-5, 2006.

European Search Report corresponding to European Application No. 07862660.3 dated Apr. 25, 2012; 7 pages.

European Search Report, EP Application No. 13863449.8, dated Oct. 19, 2015, 3 pages.

(56) References Cited

OTHER PUBLICATIONS

European Search Report, EP Application No. 14743615.8, dated Oct. 12, 2015, 3 pages.
European Search Report, EP Application No. 14743839.4, dated Oct. 12, 2015, 3 pages.
Extended European Search Report, European Application No. 16183137.5, dated Jan. 12, 2017, 12 pages.
Extended European Search Report European Application No. 16184560.7, dated Dec. 20, 2016, 9 pages.
Extended European Search Report, EP Application No. 16164775.5 dated Sep. 13, 2016, 7 pages.
Falkner et al, "Cardiovascular response to mental stress in normal adolescents with hypertensive parents. Hemodynamics and mental stress in adolescents," *Hypertension* 1979, 1:23-30.
Fitrainer "The Only Trainer You Need"; http://itami.com; Downloaded Feb. 26, 2010; ©2008 FiTriainer™; 2 pages.
Fleming et al., "A Comparison of Signal Processing Techniques for the Extraction of Breathing Rate from the Photopethysmorgram," World Academy of Science, Engineering and Technoloygy, vol. 30, Oct. 2007, pp. 276-280.
Geladas et al., "Effect of cold air inhalation on core temperature in exercising subjects under stress," The American Physiological Society, pp. 2381-2387, 1988.
Geun et al., "Measurement Site and Applied Pressure Consideration in Wrist Photoplethysmography," The $23^{rd}$ International Technical Conference on Circuits/Systems, Computers and Communications, 2008, pp. 1129-1132.
Gibbs et al., "Active motion artifact cancellation for wearable health monitoring sensors using collocated MEMS accelerometers," Smart Structures and Materials, 2005: Sensors and Smart Structures Technologies for Civil, Mechanical, and Aerospace Systems, Proc. of SPIE, vol. 5765, pp. 811-819.
Gibbs et al., "Reducing Motion Artifact in Wearable Bio-Sensors Using MEMS Accelerometers for Active Noise Cancellation," 2005 American Control Conference, Jun. 8-10, 2005, Portland, OR, USA, pp. 1581-1586.
Gold, D.R. et al. in "Ambient Pollution and Heart Rate Variability" Circulation 2000, 101:1267-1273.
Haahr et al., "A Wearable "Electronic Patch" for Wireless Continuous Monitoring of Chronically Diseased Patients," Proceedings of the $5^{th}$ International Workshop on Wearable and Implantable Body Sensor Networks, in conjunction with the $5^{th}$ International Summer School and Symposium on Medical Devices and Biosensors, The Chinese University of Hong Kong, HKSAR, China, Jun. 1-3, 2008, pp. 66-70.
Han et al., "Artifacts in wearable photoplethysmographs during daily life motions and their reduction with least mean square based active noise cancellation method," Computers in Biology and Medicine, 42, 2012, pp. 387-393.
International Preiiminary Report on Patentability, PCT/US2014/012940, dated Jun. 17, 2015, 23 pages.
International Search Report and Written Opinion of the International Searching Authority, corresponding to International Patent Application No. PCT/US2014/012940, dated Oct. 16, 2014, 3 pages.
International Search Report and Written Opinion of the International Searching Authority, corresponding to PCT/US2012/0948079, dated Oct. 9, 2012.
International Search Report and Written Opinion of the International Searching Authority, corresponding to PCT/US2007/025114, dated May 13, 2008.
International Search Report Corresponding to International Application No. PCT/US2012/022634, dated Aug. 22, 2012, 9 pages.
International Search Report corresponding to International Patent Application No. PCT/US2014/012909, dated May 13, 2014, 3 pages.
International Search Report corresponding to International Patent Application No. PCT/US2012/046446, dated Jan. 14, 2013, 3 pages.

Jiang, Honghui, "Motion-Artifact Resistant Design of Photoplethysmograph Ring Sensor for Driver Monitoring," Thesis, Massachusetts Institute of Technology, Feb. 2004, 62 pages.
Kuzmina et al., "Compact multi-functional skin spectrometry set-up," Advanced Optical Materials, Technologies, and Devices, Proc. of SPIE, vol. 6596, 2007 pp. 65960T-1 to 65960T-6.
Lee et al, "Respiratory Rate Detection Algorithms by Photoplethysmography Signal Processing," $30^{th}$ Annual International IEEE EMBS Conference, Vancouver, British Columbia, Canada, Aug. 20-24, 2006, pp. 1140-1143.
Lindberg et al., "Monitoring of respiratory and heart rates using a fibre-optic sensor," Med Biol Eng Comput, Sep. 1992, vol. 30, No. 5, pp. 533-537.
Luprano, Jean, "Sensors and Parameter Extraction by Wearable Systems: Present Situation and Future," pHealth 2008, May 21, 2008, 29 pages.
Lygouras et al., "Optical-Fiber Finger Photo-Plethysmograph Using Digital Techniques," IEEE Sensors Journal, vol. 2, No. 1, Feb. 2002, pp. 20-25.
Maguire et al., "The Design and Clinical Use of a Reflective Brachial Photoplethysmograph," Technical Report NUIM/SS/-/2002/04, Submitted Apr. 2002, Signals and Systems Research Group, National University of Ireland, Maynooth, Co. Kildare, Ireland, 13 pages.
Maomao et al., "Mobile Context-Aware Game for the Next Generation," $2^{nd}$ International Conference on Application and Development of Computer Games ADCOG 2003, p. 78-81.
Martins et al. "Zinc oxide as an ozone sensor" *Journal of Applied Physics* 96(3):1398-1408 (2004).
Maughan et al., "Exercise, Heat, Hydration and the Brain," Journal of the American College of Nutrition, vol. 26, No. 5, pp. 604S-612S, 2007.
Maughan, R.J., "Impact of mild dehydration on wellness and on exercise performance," European Journal of Clinical Nutrition, 57, Suppl. 2, pp. S19-S23, 2003.
Mendelson et al., "Measurement Site and Photodetector Size Considerations in Optimizing Power Consumption of a Wearable Reflectance Pulse Oximeter," Proceedings of the $25^{th}$ Annual International Conference of the IEEE EMBS, Cancun, Mexico, Sep. 17-21, 2003, pp. 3016-3019.
Mendelson et al., "Noninvasive Pulse Oximetry Utilizing Skin Reflectance Photoplethysmography," IEEE Transactions on Biomedical Engineering, vol. 35, No. 10, Oct. 1988, pp. 798-805.
Mostardi, R., et al., "The effect of increased body temperature due to exercise on the heart rate and the maximal aerobic power," Europ. J. Appl. Physiol, 33, pp. 237-245, 1974.
Nakajima et al., "Monitoring of heart and respiratory rates by photoplethyusmography using a digital filtering technique," Med. Eng. Phys., vol. 18, No. 5, Jul. 1996, pp. 365-372.
Notification Concerning Transmittal of Copy of International Preliminary Report on Patentability, PCT/US2014/012909, dated Jul. 28, 2015.
Notification of Transmittal of International Preliminary Report on Patentability, PCT/US2015/041562, dated Oct. 20, 2016, 14 pages.
Notification of Transmittal of International Preliminary Report on Patentability, PCT/US2015/042636, dated Oct. 20, 2016, 7 pages.
Notification of Transmittal of International Preliminary Report on Patentability, PCT/US2015/042015, dated Oct. 20 2016, 10 pages.
Notification of Transmittal of International Preliminary Report on Patentability, PCT/US2015/042035, dated Oct. 20, 2016, 8 pages.
Notification of Transmittal of International Preliminary Report on Patentability, PCT/US2015/046079, dated Oct. 20, 2016, 10 pages.
Notification of Transmittal of the International Search Report and the Written Opinion of the International Searching Authority, or the Declaration, PCT/US2016/046273, dated Nov. 25, 2016, 24 pages.
Notification of Transmittal of the International Search Report and the Written Opinion of the International Searching Authority, or the Declaration, PCT/US2016/041842, dated Oct. 21, 2016, 5 pages.
Notification of Transmittal of the International Search Report and the Written Opinion of the International Searching Authority, or the Declaration, PCT/US2016/058098, dated Jan. 10, 2017, 13 pages.

(56) References Cited

OTHER PUBLICATIONS

Notification of Transmittal of the International Search Report and Written Opinion of the International Search Authority dated May 26, 2016 by the Korean Intellectual Property Office for corresponding International Application No. PCT/US2016/019126.
Notification of Transmittal of the International Search Report and Written Opinion of the International Search Authority dated May 26, 2016 by the Korean Intellectual Property Office for corresponding International Application No. PCT/US2016/019132.
Notification of Transmittal of the International Search Report and Written Opinion of the International Search Authority dated Jul. 30, 2010 by the Korean Intellectual Property Office for corresponding International Application No. PCT/US2010/021936.
Notification of Transmittal of the International Search Report and Written Opinion of the International Search Authority dated Aug. 26, 2010 by the Korean Intellectual Property Office for corresponding International Application No. PCT/US2010/021629.
Notification of Transmittal of the International Search Report and the Written Opinion of the International Search Authority dated Sep. 16, 2010 by the Korean Intellectual Property Office for corresponding International Application No. PCT/US2010/024922.
Notification of Transmittal of the International Search Report and the Written Opinion of the International Search Authority dated Sep. 27, 2010 by the Korean Intellectual Property Office for corresponding International Application No. PCT/US2010/025216.
Notification of Transmittal of the International Search Report and The Written Opinion of the International Searching Authority, or the Declaration corresponding to International Application No. PCT/US2013/070271; dated Feb. 26, 2014; 13 pages.
Notification of Transmittal of the International Search Report and the Written Opinion of the International Searching Authority, or the Declaration, PCT/US2015/042636, dated Oct. 29, 2015.
Notification of Transmittal of the International Search Report and the Written Opinion of International Searching Authority, or the Declaration, PCT/US2015/042015, dated Oct. 29, 2015.
Notification of Transmittal of the International Search Report and the Written Opinion of the International Searching Authority, or the Declaration, PCT/US2015/042035, dated Oct. 29, 2015.
Notification of Transmittal of the International Search Report and the Written Opinion of the International Searching Authority, or the Declaration, PCT/US2015/046079, dated Dec. 29, 2015.
Poh et al., "Motion Tolerant Magnetic Earring Sensor and Wireless Earpiece for Wearable Photoplethysmography," IEEE Transactions on Information Technology in Biomedicine, vol. 14, No. 3, May 2010, pp. 786-794.
Renevey et al., "Wrist-Located Pulse Detection Using IR Signals, Activity and Nonlinear Artifact Cancellation," IEEE EMBS, 2001, 4 pages.
Rhee et al., "Artifact-Resistant Power-Efficient Design of Finger-Ring Plethysmographic Sensors," IEEE Transactions on Biomedical Engineering, vol. 48, No. 7, Jul. 2001, pp. 795-805.
Saladin et al. "Photosynthesis of $CH_4$ at a $TiO_2$ Surface from Gaseous $H_2O$ and $CO_2$" *J. Chem. Soc., Chem. Commun.* 533-534 (1995).
Shaltis, Phillip Andrew, Analysis and Validation of an Artifact Resistant Design for Oxygen Saturation Measurement Using Photo Plethysmographic Ring Sensors, Thesis, Massachusetts Institute of Technology, Jun. 2004, 103 pages.
Shin et al., "A Novel Headset with a Transmissive PPG Sensor for Heart Rate Measurement," ICBME 2008, Proceedings 23, 2009, pp. 519-522.
Shorten et al., "Acute effect of environmental temperature during exercise on subsequent energy intake in active men," Am. J Clin. Nutr. 90, pp. 1215-1221, 2009.
Skubal et al. "Detection and identification of gaseous organics using a $TiO_2$ sensor" *Journal of Photochemistry and Photobiology A: Chemistry* 148:103-108 (2002).
Skubal et al. "Monitoring the Electrical Response of Photoinduced Organic Oxideation on $TiO_2$ Surfaces" Manuscript submitted Oct. 2000 to SPIE Intl. Symposium on Environment & Industrial Sensing, Boston, MA, Nov. 5-8, 2000, sponsored by SPIE, 10 pp.
Spigulis et al, "Wearable wireless photoplethysmography sensors," Proc. of SPIE, vol. 6991, 2008, pp. 69912O-1 to 69912O-7.
Takatani et al., "Optical Oximetry Sensors for Whole Blood and Tissue," IEEE Engineering in Medicine and Biology, Jun./Jul. 1994, pp. 347-357.
Thompson, M.W., "Cardiovascular drift and critical core temperature: factors limiting endurance performance in the heat?" J. Exerc. Sci. Fit, vol. 4, No. 1, pp. 15-24, 2006.
Vogel et al., "A System for Assessing Motion Artifacts in the Signal of a Micip-Optic In-Ear Vital Signs Sensor," $30^{th}$ Annual International IEEE EMBS Conference, Vancouver, British Columbia, Canada, Aug. 20-24, 2008.
Vogel et al., "In-Ear Heart Rate Monitoring Using a Micro-Optic Reflective Sensor," Proceedings of the $29^{th}$ Annual International Conference of the IEEE EMBS Cite Internationale, Lyon, France, Aug. 23-26, 2007, pp. 1375-1378.
Wang et al., "Multichannel Reflective PPG Earpiece Sensor With Passive Motion Cancellation," IEEE Transactions on Biomedical Circuits and Systems, vol. 1, No. 4, Dec. 2007, pp. 235-241.
Wang et al., "Reflective Photoplethysmograph Earpiece Sensor for Ubiquitous Heart Rate Monitoring," $4^{th}$ International Workshop on Wearable and Implantable Body Sensor Networks, 2007, vol. 13 of the series IFMBE Proceedings, pp. 179-183.
Wei et al. "A New Wristband Wearable Sensor Using Adaptive Reduction Filter to Reduce Motion Artifact," Proceedings of the $5^{th}$ International Conference on Information Technology and Application in Biomedicine, in conjunction with The $2^{nd}$ International Symposium & Summer School on Biomedical and Health Engineering, Shenzhen, China, May 30-31, 2008, pp. 278-281.
Wood et al., "Active Motion Artifact Reduction for Wearable Sensors Using Laguerre Expansion and Signal Separation," Proceedings of the 2005 IEEE Engineering in Medicine and Biology, $27^{th}$ Annual Conference, Shanghai, China, Sep. 1-4, 2005, pp. 3571-3574.
Wood, Levi Benjamin, "Motion Artifact Reduction for Wearable Photoplethysmogram Sensors Using Micro Accelerometers and Laguerre Series Adaptive Filters," Thesis, Massachusetts Institute of Technology, Jun. 2008, 74 pages.
Zhang et al. "Development of Chemical Oxygen Demand On-Line Monitoring System Based on a Photoelectrochemical Degradation Principle" *Environ. Sci. Technol.*, 40(7):2363-2368 (2006).
Extended European Search Report corresponding to European Application No. 17150916.9 dated Jul. 5, 2017 (10 pages).

\* cited by examiner

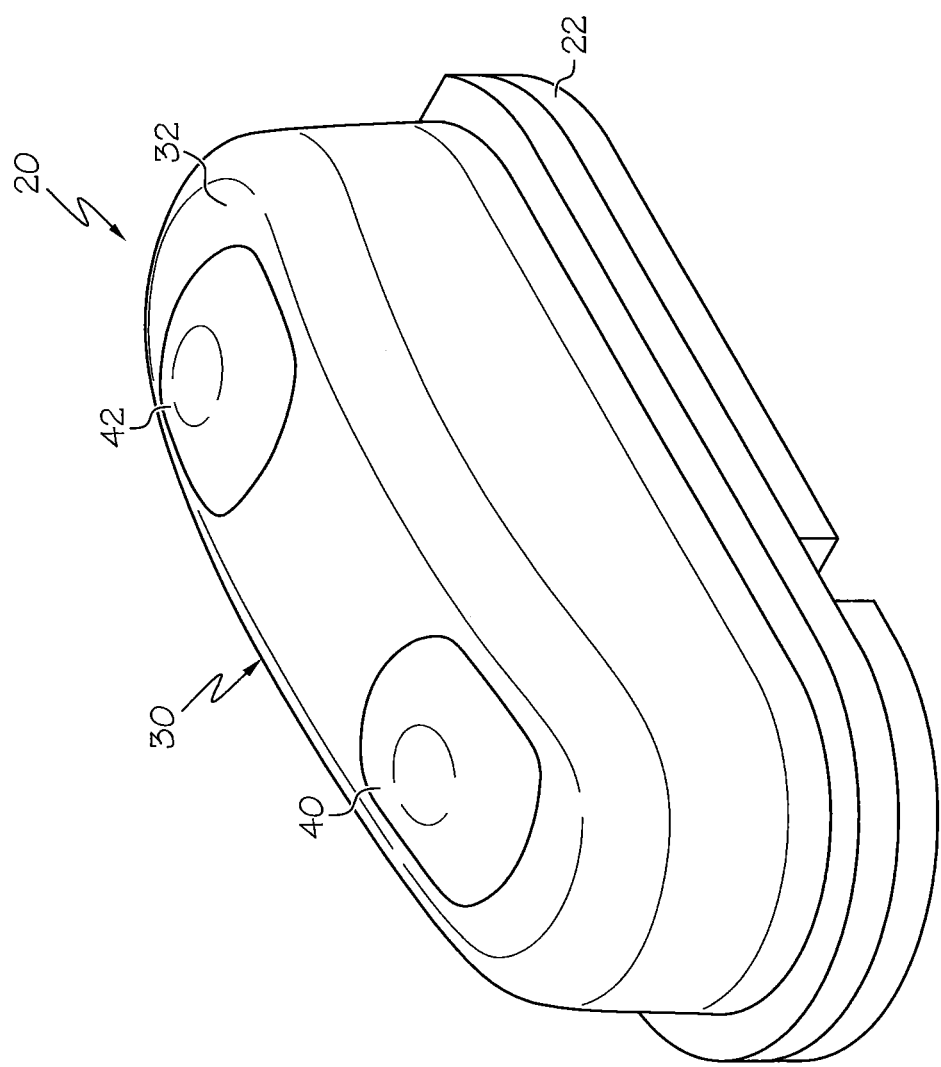

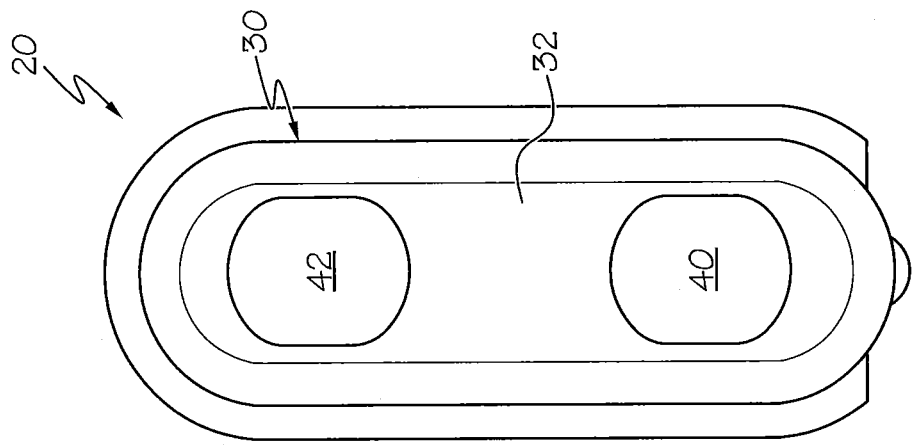
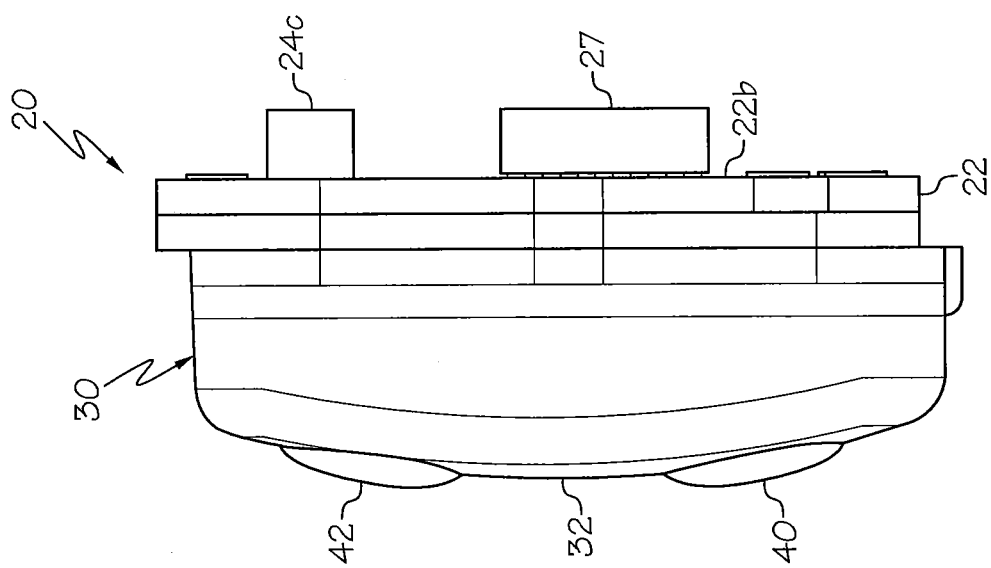

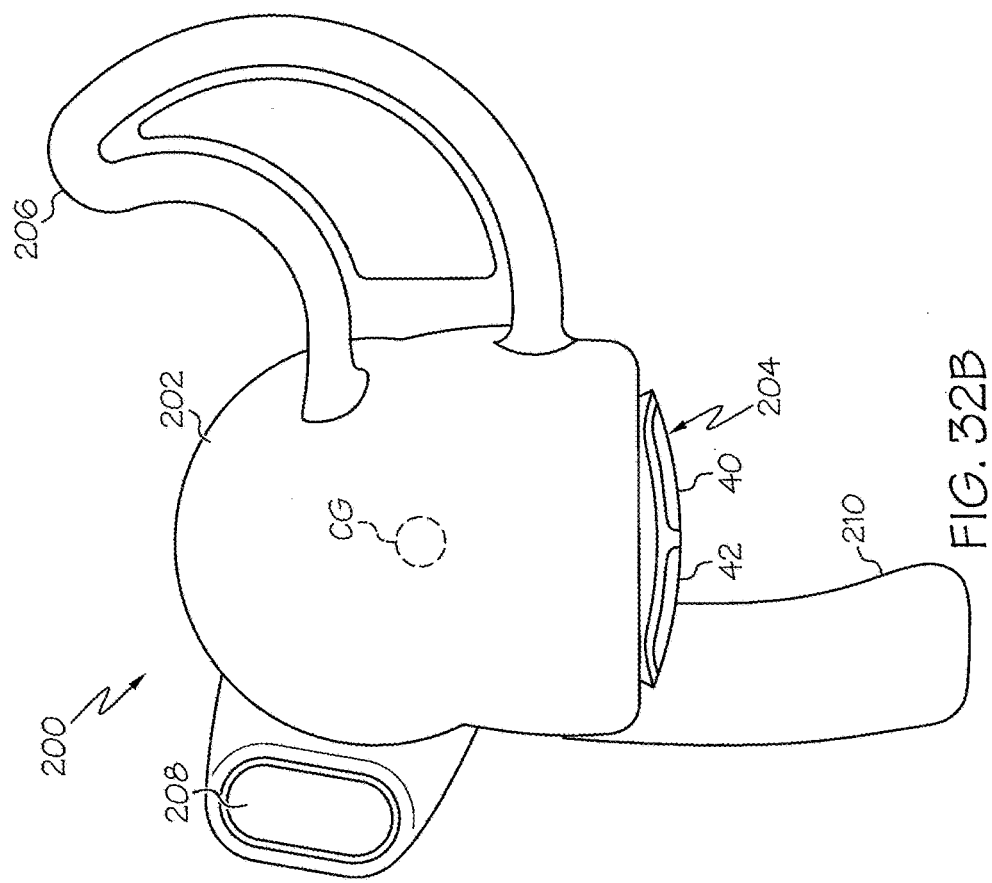
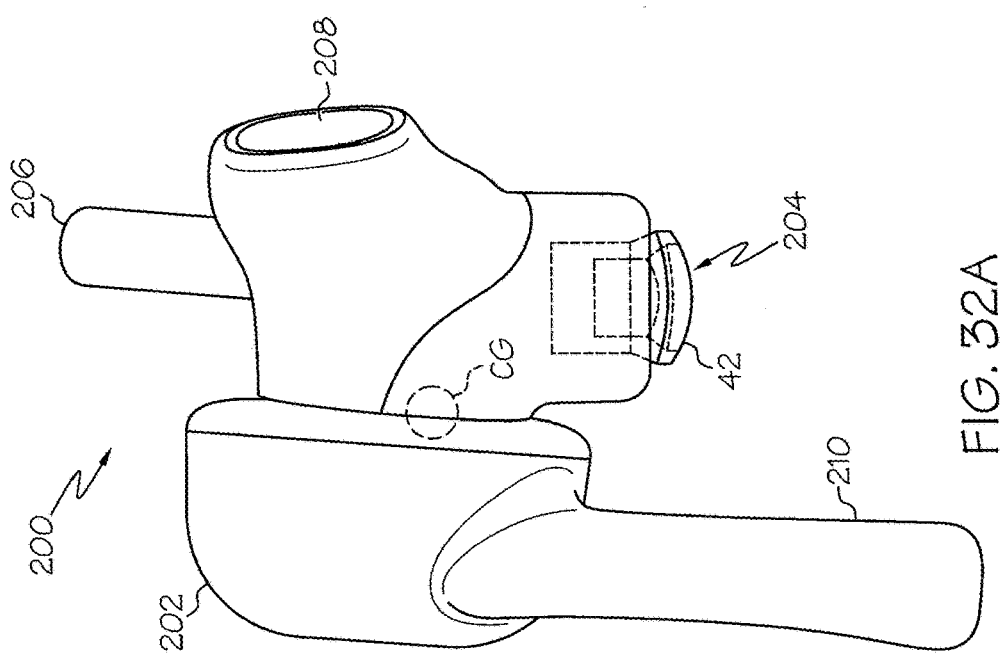
FIG. 32A
FIG. 32B

EARBUD MONITORING DEVICES

RELATED APPLICATIONS

This application is a continuation of U.S. patent application Ser. No. 15/324,139, filed Jan. 5, 2017, which is a 35 U.S.C. § 371 national stage application of PCT Application No. PCT/US2015/041562, filed on Jul. 22, 2015, which claims the benefit of and priority to U.S. Provisional Patent Application No. 62/033,922 filed Aug. 6, 2014, the disclosures of which are incorporated herein by reference as if set forth in their entireties.

FIELD OF THE INVENTION

The present invention relates generally to monitoring devices and, more particularly, to optical sensor devices.

BACKGROUND OF THE INVENTION

There is growing market demand for personal health and environmental monitors, for example, for gauging overall health and metabolism during exercise, athletic training, dieting, daily life activities, sickness, and physical therapy. However, traditional health monitors and environmental monitors may be bulky, rigid, and uncomfortable—generally not suitable for use during daily physical activity.

Sensors for detecting biometric signals, such as vital signs and other physiological information, are configured to isolate the biometric signals from other spurious signals and deliver biometric readings, such as heart rate, respiration rate, blood pressure, etc., to the user. Unfortunately, spurious signals that may be difficult to isolate from a biometric signal are associated with physical movement (e.g., physical exercise, such as walking, running, daily activities, etc.) of a sensor relative to the user or the environment of the user (e.g., sunlight, room light, humidity, ambient acoustical or electromagnetic noise, temperature extremes or changes in temperature, etc.).

For example, referring to FIG. 1, a conventional photoplethysmography (PPG) optical sensor 10 is illustrated that includes an optical source 14, and an optical detector 16. The optical sensor 10 is desirably positioned directly against the body B (i.e., the skin) of a subject wearing the optical sensor such that light $L_1$ from the optical source 14 is directed into the body B and is subsequently detected by the optical detector 16. However, movement of the user can cause the sensor 10 to move relative to the body B such that light $L_2$ can take a direct path from the optical source 14 into the optical detector 16 (for example by reflection off of the body, i.e., the skin, of the user), which increases spurious signals. Moreover, motion artifacts may cause the distance between the sensor 10 and body B to change in time, thereby modulating $L_1$ and $L_2$ in time, leading to motion artifact noise on the signal generated by the detector 16.

Previous ways of isolating heart rate signals from other signals include the use of passive and active signal processing algorithms, increasing optical sensor output and displacing the optical source from the photodetector, and pushing the sensor more firmly against the user so as to limit the effects of physical movement on the heart rate signal.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a wearable optical sensor includes at least one optical emitter, at least one optical detector and light-guiding optics. The light-guiding optics are configured to direct a beam pattern of light upon a body of a subject wearing the optical sensor and to detect light scattered from a detection region of the body. In addition, the light-guiding optics are configured to prevent overlap between the beam pattern of light and the detection region when the wearable sensor is separated from the body, for example, by a distance up to about three tenths of a centimeter (0.3 cm). In some embodiments, the light-guiding optics includes optical filtering material and/or light polarizing material.

According to some embodiments of the present invention, an optical sensor module for detecting and/or measuring physiological information from a subject and that can be integrated into a wearable device, such as a headset (e.g., an earbud, etc.), an armband, a wristband, clothing, foot apparel, a ring, etc., includes a base and a housing secured to the base. The base includes an optical source and an optical detector. The housing overlies the optical source and optical detector and includes a first light guide comprising light transmissive material in optical communication with the optical source and a second light guide comprising light transmissive material in optical communication with the optical detector. The first and second light guides define respective first and second axial directions that are outwardly diverging. The first axial direction of the first light guide is angled relative to a plane defined by a surface of the optical source, and the second axial direction of the second light guide is angled relative to a plane defined by a surface of the optical detector. When the sensor module is in use and placed adjacent the skin of a user, a substantial majority of light rays emanating from the optical source and directed into the skin of the user cannot overlap with light rays returning through the skin of the user and collected by the second light guide when the housing is separated from the skin, for example, by a distance up to about three tenths of a centimeter (0.3 cm).

In some embodiments, at least one of the first and second light guides is cylindrical. In other embodiments, at least one of the first and second light guides is non-cylindrical.

The first and second light guides include opposite proximal and distal ends. In some embodiments, the proximal and distal ends of at least one of the first and second light guides have different sizes. For example, the diameter of a light guide distal end may be greater than a diameter of the proximal end thereof. Alternatively, the diameter of a light guide distal end may be smaller than a diameter of the proximal end thereof. In some embodiments, the proximal and distal ends of at least one of the first and second light guides may have different configurations. For example, the proximal end of a light guide may have one type of geometric configuration and the distal end may have a different geometric configuration. As an example, the proximal end may have a triangular configuration and the distal end may have a rectangular configuration, etc.

In some embodiments, the distal end of at least one of the first and second light guides has a curved surface. In other embodiments, the distal end of at least one of the first and second light guides has a textured surface.

In some embodiments, multiple light guides may be substituted for a single light guide either on the optical source or over the optical detector.

In some embodiments, single or multiple light guides may be placed over multiple optical sources or multiple optical detectors.

Optical sensor modules according to embodiments of the present invention are advantageous because they can lower the sensitivity of an optical signal to sensor-user movement related noise, thereby enabling a significant improvement in heart rate monitoring consistency across subjects and types of exercise activities.

According to some embodiments of the present invention, a headset includes a base comprising an optical source and an optical detector, and a housing that is secured to the base and is configured to be positioned at or within an ear of a subject. The housing overlies the optical source and optical detector and includes a first light guide in optical communication with the optical source and a second light guide in optical communication with the optical detector. The first and second light guides define respective first and second axial directions that are outwardly diverging.

According to some embodiments of the present invention, an optical sensor module includes a base having an optical source and an optical detector, a housing secured to the base that overlies the optical source and optical detector, and at least one light polarizing element in optical communication with the optical source and the optical detector. The at least one polarizing element is configured to polarize light emitted by the optical source and/or polarize light detected by the optical detector.

In some embodiments, the at least one light polarizing element is a light polarizing film, a light polarizing lens, and/or a light polarizing light guiding material in the optical path of the optical source and/or the optical detector.

In some embodiments, the at least one light polarizing element includes a first light polarizing element in optical communication with the optical source and a second light polarizing element in optical communication with the optical detector. The first and second light polarizing elements may have the same light polarization orientation or may have respective different light polarization orientations.

In some embodiments, the sensor module housing includes at least one window through which light from the optical source passes and/or through which light detected by the optical detector passes. The at least one window includes the at least one polarizing element. For example, the at least one window may include a first window in optical communication with the optical source and a second window in optical communication with the optical detector. The first window includes a polarizing element (e.g., a polarizing film, etc.) and the second window includes a polarizing element (e.g., a polarizing film, etc.). The first and second window polarizing elements may have the same light polarization orientation or may have respective different light polarization orientations.

According to other embodiments of the present invention, an optical sensor module for detecting and/or measuring physiological information from a subject includes a base having an optical source and an optical detector, and a housing secured to the base that overlies the optical source and optical detector. The housing includes a first light guide in optical communication with the optical source and a second light guide in optical communication with the optical detector. The first light guide includes light polarizing material that is configured to polarize light emitted by the optical source, and the second light guide includes light polarizing material that is configured to polarize light detected by the optical source. The first light guide light polarizing material and the second light guide light polarizing material may have the same light polarization orientation or may have respective different light polarization orientations.

According to other embodiments of the present invention, an optical sensor module for detecting and/or measuring physiological information from a subject includes a housing, an optical source supported by the housing, an optical detector supported by the housing, and at least one light polarizing element supported by the housing. The at least one light polarizing element is configured to polarize light emitted by the optical source and/or polarize light detected by the optical detector. In some embodiments, the at least one light polarizing element is a light polarizing film, a light polarizing lens, and/or a light polarizing light guiding material in the optical path of the optical source and/or the optical detector.

In some embodiments, the at least one light polarizing element includes a first light polarizing element in optical communication with the optical source and a second light polarizing element in optical communication with the optical detector. The first and second light polarizing elements may have the same light polarization orientation or may have respective different light polarization orientations.

In some embodiments, the sensor module housing includes at least one window through which light from the optical source passes and/or through which light detected by the optical detector passes. The at least one window includes the at least one polarizing element. For example, the at least one window may include a first window in optical communication with the optical source and a second window in optical communication with the optical detector. The first window includes a polarizing element (e.g., a polarizing film, etc.) and the second window includes a polarizing element (e.g., a polarizing film, etc.). The first and second window polarizing elements may have the same light polarization orientation or may have respective different light polarization orientations.

According to other embodiments of the present invention, an earbud includes a speaker driver, and a sensor module secured to the speaker driver that is configured to detect and/or measure physiological information from a subject wearing the earbud. In some embodiments, the sensor module includes a printed circuit board (PCB), an optical source secured to the PCB, and an optical detector secured to the PCB. In some embodiments, the PCB is an elongated, flexible PCB having a distal end portion, and the optical source and optical detector are secured to the PCB at the distal end portion.

In some embodiments, the earbud includes a first light guide coupled to the optical source and a second light guide coupled to the optical detector. The first light guide is configured to deliver light from the optical source into an ear region of the subject via a distal end thereof, and the second light guide is configured to collect light from the ear region via a distal end thereof and deliver collected light to the optical detector.

In some embodiments, the earbud includes one or more additional sensors secured to the speaker driver. Exemplary additional sensors include, but are not limited to, accelerometers, humidity sensors, altimeters, and temperature sensors.

In some embodiments, the earbud includes at least one signal processor configured to process signals produced by the optical detector. In other embodiments, the earbud is in communication with a data processing unit that is configured to process signals produced by the optical detector.

According to other embodiments of the present invention, a monitoring device includes a band capable of at least partially encircling a portion of a body of a subject, and an optical source and an optical detector supported by the band. The band includes a first light guide in optical communication with the optical source and a second light guide in optical communication with the optical detector. The first and second light guides define respective first and second axial directions, and the first and second axial directions diverge outwardly from the band. In some embodiments, the first and second light guides are angled relative to each other such that light rays emanating from the optical source and directed into the skin of the subject via the first light guide cannot overlap with light rays collected by the second light guide even when the housing is separated from the ear by a distance up to about three tenths of a centimeter (0.3 cm). In some embodiments, the first axial direction of the first light guide is angled relative to a plane defined by the optical source, and the second axial direction of the second light guide is angled relative to a plane defined by the optical detector.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

FIG. 12A is a front perspective view of an optical sensor module, according to some embodiments of the present invention.

FIG. 12C is a side view of the optical sensor module of FIG. 12A.

FIG. 12D is a front view of the optical sensor module of FIG. 12A.

FIG. 32A is a side view of a biometric monitoring device, according to some embodiments of the present invention, and illustrating the center of gravity of the monitoring device.

FIG. 32B is a front view of the biometric monitoring device of FIG. 32A.

DETAILED DESCRIPTION

Figure 1:
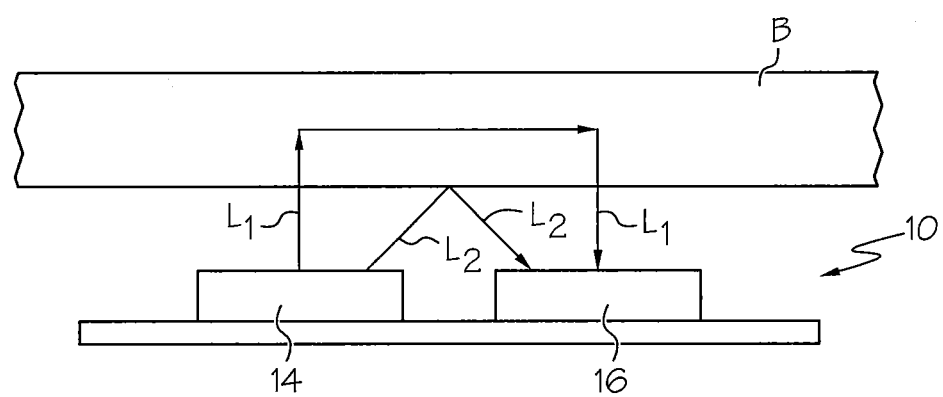
FIG. 1 is a side section view of a conventional optical sensor illustrating how light can take a direct path from an optical source to an optical detector via reflection off of the skin of a subject wearing a device incorporating the optical sensor.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled", or "secured" to another feature or element, it can be directly connected, attached, coupled, or secured to the other feature or element or intervening features or elements may be present. In contrast, when a feature or element is referred to as being "directly connected", "directly attached", "directly coupled", or "directly secured" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary, for example, by +/−20%, +/−10%, +/−5%, +/−1%, +/−0.5%, or even +/−0.1%.

The term "headset", as used herein, is intended to include any type of device or earpiece that may be attached to or near the ear (or ears) of a user and may have various configurations, without limitation. Headsets incorporating optical sensor modules, as described herein, may include mono headsets (a device having only one earbud, one earpiece, etc.) and stereo headsets (a device having two earbuds, two earpieces, etc.), earbuds, hearing aids, ear jewelry, face masks, headbands, and the like. In some embodiments, the term "headset" may include broadly headset elements that are not located on the head but are associated with the headset. For example, in a "medallion" style wireless headset, where the medallion comprises the wireless electronics and the headphones are plugged into or hard-wired into the medallion, the wearable medallion would be considered part of the headset as a whole. Similarly, in some cases, if a mobile phone or other mobile device is intimately associated with a plugged-in headphone, then the term "headset" may refer to the headphone-mobile device combination.

The terms "optical source" and "optical emitter", as used herein, are interchangeable.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" may include monitoring blood gas levels, blood hydration, and metabolite/electrolyte levels, etc.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "body" refers to the body of a subject (human or animal) that may wear a device incorporating one or more optical sensor modules, according to embodiments of the present invention.

The term "coupling", as used herein, refers to the interaction or communication between excitation light entering a region of a body and the region itself. For example, one form of optical coupling may be the interaction between excitation light generated from an optical sensor module and the blood vessels of the body of a user. In one embodiment, this interaction may involve excitation light entering the ear region and scattering from a blood vessel in the ear such that the intensity of scattered light is proportional to blood flow within the blood vessel.

The term "processor" is used broadly to refer to a signal processor or computing system or processing or computing method which may be localized or distributed. For example, a localized signal processor may comprise one or more signal processors or processing methods localized to a general location, such as to a wearable device. Examples of such wearable devices may comprise an earpiece, a headset, a headpiece, a finger clip/band, a toe clip/band, a limb band (such as an arm band or leg band), an ankle band, a wrist band, a nose band, a sensor patch, or the like. Examples of a distributed processor include "the cloud", the internet, a remote database, a remote processor computer, a plurality of remote processors or computers in communication with each other, or the like, or processing methods distributed amongst one or more of these elements. The key difference is that a distributed processor may include delocalized elements, whereas a localized processor may work independently of a distributed processing system. As a specific example, microprocessors, microcontrollers, ASICs (application specific integrated circuits), analog processing circuitry, or digital signal processors are a few non-limiting examples of physical signal processors that may be found in wearable devices.

The term "remote" does not necessarily mean that a remote device is a wireless device or that it is a long distance away from a device in communication therewith. Rather, the term "remote" is intended to reference a device or system that is distinct from another device or system or that is not substantially reliant on another device or system for core functionality. For example, a computer wired to a wearable device may be considered a remote device, as the two devices are distinct and/or not substantially reliant on each other for core functionality. However, any wireless device (such as a portable device, for example) or system (such as a remote database for example) is considered remote to any other wireless device or system.

Sensor modules, according to embodiments of the present invention may be integrated into various wearable devices including, but not limited to headsets (e.g., earbuds, etc.), wristbands, arm bands, leg bands, rings, patches, etc.

Figure 2:
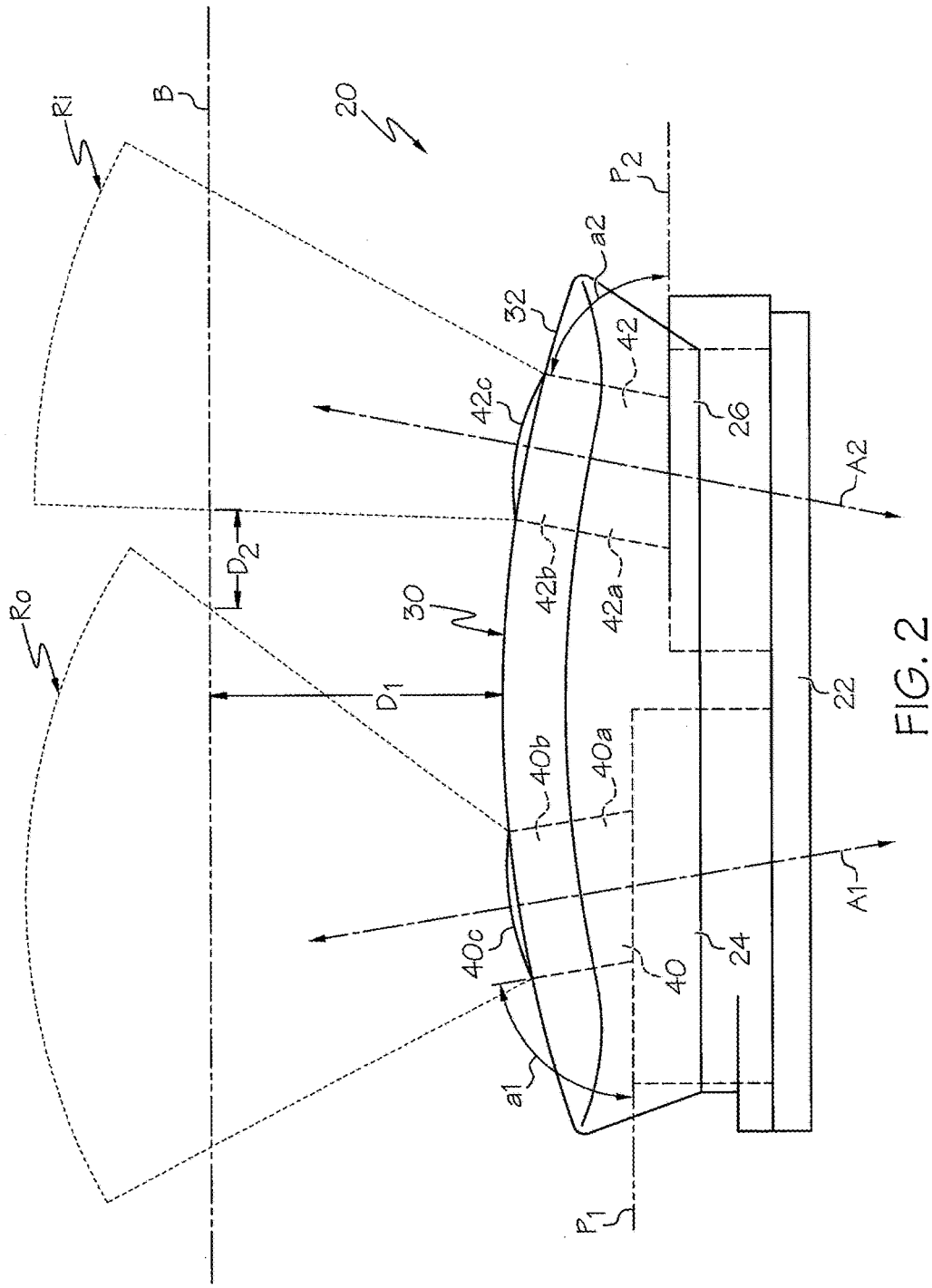
FIG. 2 is a side section view of an optical sensor module having light guides, according to some embodiments of the present invention.

Referring to FIG. 2, an optical sensor module 20 that may be incorporated into a wearable device according to some embodiments of the present invention is illustrated. The illustrated sensor module 20 includes a substrate or base 22 (e.g., a circuit board, etc.) having an optical source 24 and an optical detector 26. As would be understood by one skilled in the art of the present invention, the base 22 may support and/or be connected to various electronic components including, but not limited to, a signal processor, a wireless module for communicating with a remote device, a memory storage device, etc. Moreover, a battery, such as a lithium polymer battery or other portable battery, may be mounted to or connected to the base 22 and may be charged via a charge port, such as a USB charge port, for example. Additionally, the base 22 may be flexible, may be rigid, or may include a combination of flexible and rigid material. The base 22 may have various configurations suitable for supporting electronics.

The optical source 24 may be one or more light-emitting diodes (LED), laser diodes (LD), compact incandescent bulbs, micro-plasma emitters, IR blackbody sources, organic LEDs, or the like. The optical detector 26 may be one or more photodiodes, photodetectors, phototransistors, thyristors, solid state devices, optical chipsets, or the like.

Figure 14:
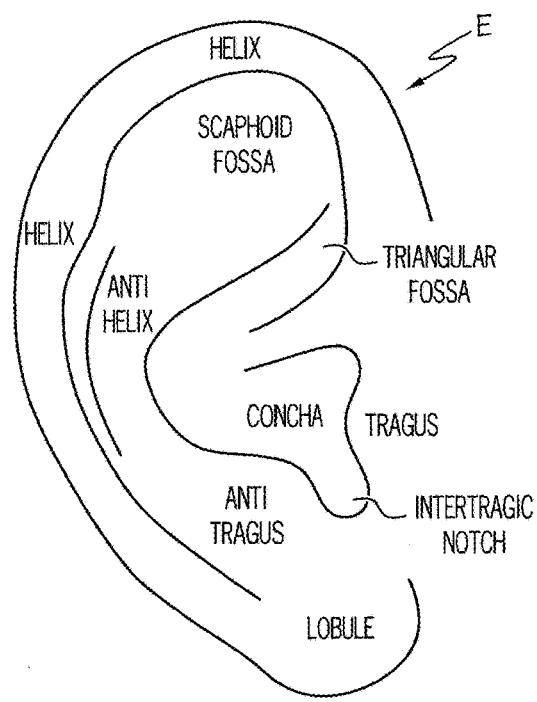
FIG. 14 is an illustration of a human ear with various portions thereof labeled.

A housing 30 is secured to the base 22 and overlies the optical source 24 and optical detector 26. The illustrated housing 30 has a curved outer surface 32 that is configured to engage a particular portion of the body of a user of the sensor module 20 (i.e., a person wearing a device incorporating the optical sensor module 20). For example, in some embodiments, the sensor module 20 may be incorporated into an earbud and the housing outer surface 32 is contoured to matingly engage a particular region of the ear (e.g., the region between the anti-tragus and the concha, the region along the helix or anti-helix of the ear, etc., as illustrated in FIG. 14). However, the housing outer surface 32 may have various shapes and configurations and need not be curved. For example, in some embodiments, the outer surface 32 of the housing may be flat such that the sensor module 20 may be integrated within a wristband.

The term "matingly engage", as used herein, does not necessarily mean that the housing 30 must physically touch the body of the person; rather, "matingly engage" implies that the housing 30 is designed to optically or optomechanically couple with a particular region of the body or to have a physical structure that compliments a particular region of the body. For example, the housing 30 of FIG. 2 may fit well within an audio earbud and support optical coupling between the anti-tragus and concha of the ear, but a flat housing structure may be more suitable for the housing enabling optical coupling to a person's wrist.

Though FIG. 2 presents a convex (outward-curving) housing 30, a concave (inward-curving) housing 30 may be better suited for other regions of the body. For example, a concave housing 30 may be well-suited for a digit or limb of the body. Additionally, a concave housing 30 may be well-suited for coupling to the ear region behind the ear, adjacent to the earlobe.

The illustrated housing 30 includes a first light guide 40 in optical communication with the optical source 24 and a second light guide 42 in optical communication with the optical detector 26. In addition to supporting the first and second light guides 40, 42, the housing 30 may be configured to enclose and protect the various electronic components mounted to the base 22 from ambient interference (air, humidity, particulates, electromagnetic interference, etc). In some embodiments, the housing 30 may comprise opaque material that prevents light from escaping or entering the light guides 40, 42 laterally (i.e., confines light within the light guides 40, 42 such that light only enters and exits through the respective light guide ends). However, embodiments of the present invention do not require the housing to comprise opaque material.

The first light guide 40 comprises light transmissive material configured to deliver light from the optical source 24 into a region of a body of a user at one or more predetermined locations. The second light guide 40 comprises light transmissive material configured to collect light external to the sensor module 20 and deliver the collected light to the optical detector 26. The first and second light guides 40, 42 may be formed from various types of light transmissive material. In some embodiments, one or both of the first and second light guides 40, 42 may be formed from an elastomeric light transmissive material. In other embodiments, one or both of the first and second light guides 40, 42 may be formed from a substantially rigid light transmissive material. In some embodiments, one or both of the first and second light guides 40, 42 may be formed from a combination of elastomeric light transmissive material and substantially rigid light transmissive material. Exemplary light transmissive materials include, but are not limited to, polycarbonate, acrylic, silicone, glass, metal oxides, polyurethane, etc. In addition, one or both of the first and second light guides 40, 42 may comprise one or more optical fibers.

In some embodiments, a physical optical filter may be disposed along the optical paths $R_o$ and $R_i$ such that only certain wavelengths of light are allowed to leave or enter the sensor module 20. The physical optical filter can be disposed anywhere along the optical path(s), and may be any variety of filters that are well known in the art, as well as new, innovative filters. An optical filter may be composed of polycarbonate, acrylic, silicone, glass, metal oxides, polyurethane, etc. In some embodiments, an optical filter may be a small slab that is placed in the optical path of the optical source 24 and/or optical detector 26 and may be supported by the structure of the sensor module 20. In some embodiments, an optical filter may be integrated with the optical source 24 and/or the optical detector 26. For example, a bandpass filter, such as an interference filter or the like, may be disposed on the top of the optical source 24 and/or optical detector 26. Alternatively (or additionally), an optical filter effect may be integrated within the semiconductor material comprising the optical source 24 and/or optical detector 26, such as by selective ion implantation of certain regions within silicon or by band-gap engineering within compound semiconductors, such as the AlInGaAs or AlInGaN system of semiconductor engineering.

In some embodiments, an optical filter may be integrated within one or more of the light guides 40 and 42. For example, one or both of the first and second light guides 40, 42 may comprise a material having an optically filtering dye or a material which inherently filters one or more wavelengths of light. As one example, either or both of the light guides 40 and 42 may comprise, wholly or partially, a dye therewithin. As one specific example, at least one light guide may comprise a dye, such as an infrared dye designed to block visible wavelengths but pass IR wavelengths. For example, a polycarbonate or acrylic light guide 40 or 42, dyed with Gentex-E800, would facilitate both light-guiding and IR-pass filtering functionality. Alternatively, another example of such an integrated physical optical filter comprises Filtron® absorptive dyes dispersed in polycarbonate and/or acrylic to create an edge or long-pass optical filter. Such materials may be conventionally molded, extruded, and/or fabricated into an optical filter having a variety of shapes. In the case of FIG. 2, at least one light guide may be partially or wholly comprised of such a material, thereby facilitating the combinational purpose of light guiding and optical filtering.

A few additional non-limiting examples of an inherently filtering material includes sapphire, which absorbs some infrared (IR) wavelengths, and glass, which absorbs some ultraviolet (UV) wavelengths. However, various types of filtering material may be utilized, without limitation. In some embodiments, one or both of the light guides 40, 42 may be surrounded or partially surrounded by a cladding/barrier material (not shown) that is configured to at least partially block light from an external source from entering one or both of the light guides 40, 42 at select locations along the light guides 40, 42 and/or at least partially confine light within one or both light guides 40, 42. The cladding/barrier material may be a light blocking material and/or a light reflective material and/or a material that has a higher optical scattering coefficient than the light guiding material of the light guides 40, 42. For example, the cladding material may be a dark (e.g., black, etc.) or silver (or other reflective color) coating, a material with refractive index that differs from the core light guide material, or a texturized light-scattering material on one or more portions of a distal end surface 40c, 42c of one or both of the light guides 40, 42.

The first light guide 40 defines a first axial direction $A_1$, and the second light guide 42 defines a second axial direction $A_2$, as illustrated in FIG. 2. The first axial direction $A_1$ of the first light guide 40 has an angle a1 relative to a plane $P_1$ defined by a surface of the optical source 24 that is less than ninety degrees (90°), and the second axial direction $A_2$ of the second light guide 42 has an angle a2 relative to a plane $P_2$ defined by a surface of the optical detector 26 that is less than ninety degrees (90°). As such, the first and second light guides 40, 42 are positioned within the housing 30 such that they diverge outwardly from the housing 30.

In some embodiments of the present invention, one or both of the first and second light guides 40, 42 may have a generally cylindrical configuration. In other embodiments, one or both of the first and second light guides 40, 42 may have a generally non-cylindrical configuration, e.g., rectangular, triangular, oval, etc.

Each of the first and second light guides 40, 42 has a respective proximal end 40a, 42a and an opposite distal end 40b, 42b. The proximal end 40a of the first light guide 40 is positioned adjacent the optical source 24, and the proximal end 42a of the second light guide 42 is positioned adjacent the optical detector 26. In the illustrated embodiment, the distal end 40b, 42b of the light guides 40, 42 extends slightly outwardly from the housing 30. However, in other embodiments of the present invention, the distal end portion 40b, 42b of one or both light guides 40, 42 may be substantially flush with the housing 30 or may even be recessed within the housing 30.

Light guides that extend from the housing 30 (as opposed to light guides that are flush with the housing 30) may facilitate a higher signal-to-noise (S/N) ratio for biometrically modulated light vs. unwanted optical scatter, because extended light guides may capture more of the desired biometric signal and/or may reject more of the unwanted noise. Namely, in PPG, blood flowing through a blood vessel will cause optical scatter directly or indirectly related to blood flow changes. However, there will also be unwanted optical scatter associated with light bouncing off (i.e., reflecting off) the skin and other body tissues in a manner that is not biometrically modulated (i.e., light that is not interacting with blood flow changes). The desired signal "S" is comprised of light that is biometrically modulated and the noise "N" is comprised of all other scattered light (such as light scattered by skin, other body tissues, motion artifacts, environmental artifacts, etc.). As will be described later, the shape and angle of the light guides may help increase the S/N ratio.

Light guides that are flush with the housing 30 (as opposed to light guides that are extended from the housing 30) may be more aesthetically appealing to those wearing an earbud, armband, or other wearable device form-factor that integrates the sensor module 20. This is because there will be no substantial protrusions that would make the wearable device look much different than a wearable device that does not integrate such a sensor module. Moreover, there may be a higher degree of wearability and comfort associated with flush light guides if there are no protrusions that may potentially generate discomfort after a period of time wearing a device incorporating the sensor module 20.

Figure 3A:
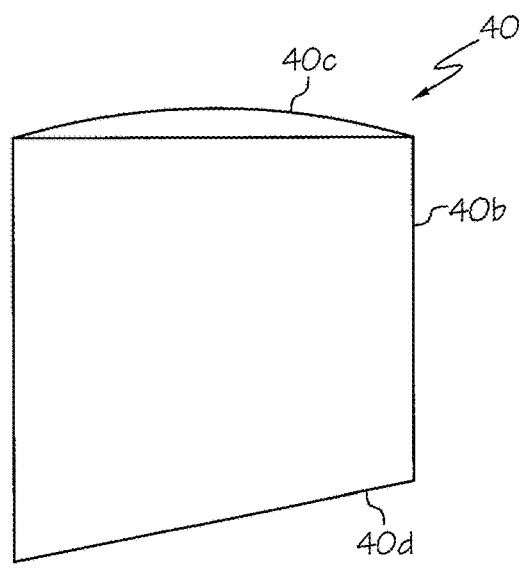
FIG. 3A is an enlarged, partial view of the distal end of a light guide from the optical sensor module of FIG. 2 and which illustrates a curved configuration of the surface of the light guide distal end.

The distal end 40b, 42b of each illustrated light guide 40, 42 has a respective exposed end surface 40c, 42c that is configured to engage (or be positioned adjacent or near) a portion of the body B of a user. In some embodiments, the end surface 40c, 42c of one or both of the light guides 40, 42 may have a curved configuration. For example, FIG. 3A illustrates a rounded end surface 40c of the first light guide 40 of the sensor module 20 of FIG. 2. In other embodiments, the end surface 40c, 42c of one or both of the light guides 40, 42 may have a flat configuration. However, the end surface 40c, 42c of one or both of the light guides 40, 42 may be shaped in a variety of ways to couple light to and from the body of a user. For example, a rounded surface may improve light collection from a wider angle and a flat surface may narrow the field of view of the light guide. In some cases, a wider field of view may be important to measure more light from a broader range along the body, but in other cases, a narrower view may be important to focus the field of view on a specific region of the body. Note that the bottom 40d of the light guide 40 of FIG. 3A is at an angle with respect to the top 40c of the light guide 40. Although only light guide 40 is illustrated in FIG. 3A, it is understood that the other light guide 42 may have a bottom portion that is at an angle with respect to a top portion thereof. This alteration of symmetry may provide better coupling of light from/to the optical source 24/optical detector 26 to/from the respective light guide 40, 42 while simultaneously directing the respective light paths at the angles a1 and a2 (FIG. 2).

In some embodiments, the end surface 40c, 42c of one or both of the light guides 40, 42 may be textured with a non-optically smooth finish such as an SPI (Society of Plastics Industry) B-1 finish, or the like. However, other finish texturing may be used in accordance with embodiments of the present invention including, but not limited to, SPI A-1, SPI A-2, SPI A-3, SPI B-2, and SPI B-3. However, embodiments of the present invention do not require surface texturing of the end surfaces 40c, 42c.

Figure 3B:
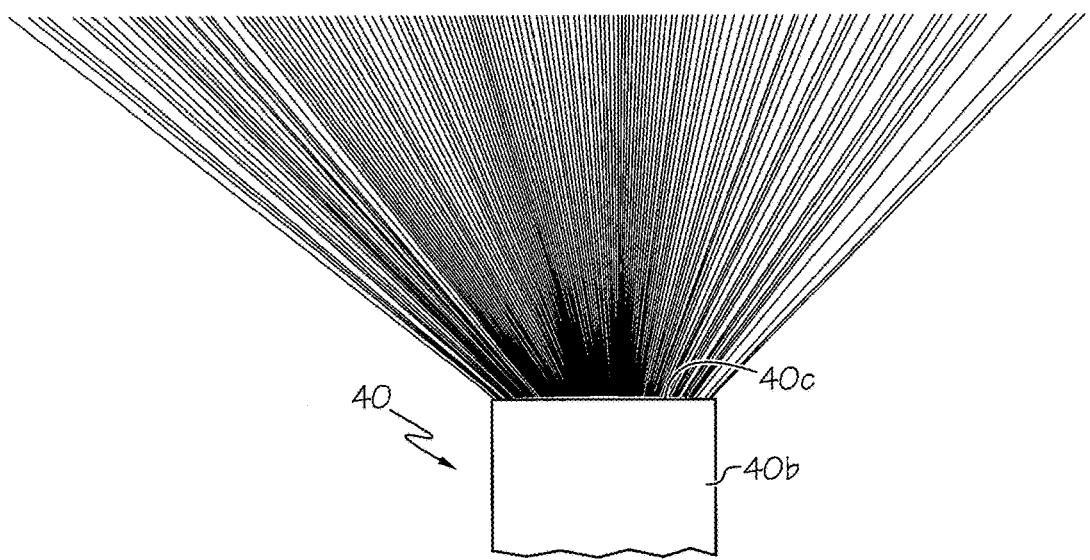
FIG. 3B is an enlarged, partial view of the distal end of a light guide from the optical sensor module of FIG. 2 and which illustrates a textured configuration of the surface of the light guide distal end and light rays emanating from the textured surface.

FIG. 3B illustrates the optical impact of a textured end surface 40c of the light guide 40 of the sensor module 20 of FIG. 2. A textured surface can cause a "feathering" or "diffusing" of light from the optical source 24, thereby limiting the light that reflects directly from the tissue and into the optical detector 26. A diffuse optical beam may also be more uniform than a beam of light generated by the optical source 24. Diffused light beams may have an intensity distribution that is less sensitive to body motion and may be useful in alleviating motion artifacts in scattered light coming from the body and detected by the optical detector 26. The texturing features in this particular example of FIG. 3B were generated with an average texturing feature size smaller than about 100 μm, and the diameter of the light guide was about 3 mm.

The angled configuration of the first and second light guides 40, 42 prevents most or all light from the optical source 24 from directly reaching the optical detector 26 (i.e., without passing through a portion of the body of a user first) when the outer surface 32 of the housing 30 is separated from the body of a user, for example, by a distance up to about three tenths of a centimeter (0.3 cm) or more. This is illustrated in FIG. 2 wherein the dotted line B is representative of the body (i.e., the skin) of a user. Distance $D_1$ represents the distance from the body B to the outer surface 32 of the housing 30. Rays of light emanating from the optical source are represented by $R_o$ and rays of light detected by the optical detector are represented by $R_i$. The light rays $R_o$ emanating from the optical source 24 do not overlap with the light rays $R_i$ returning to the optical detector 26 over the distance $D_1$, as represented by distance $D_2$. As such, the light emanating from the optical source 24 is directed along the most physiologically meaningful signal pathway (i.e., through the body B and without substantial, unwanted reflection from the body B into the optical detector 26).

Figure 4:
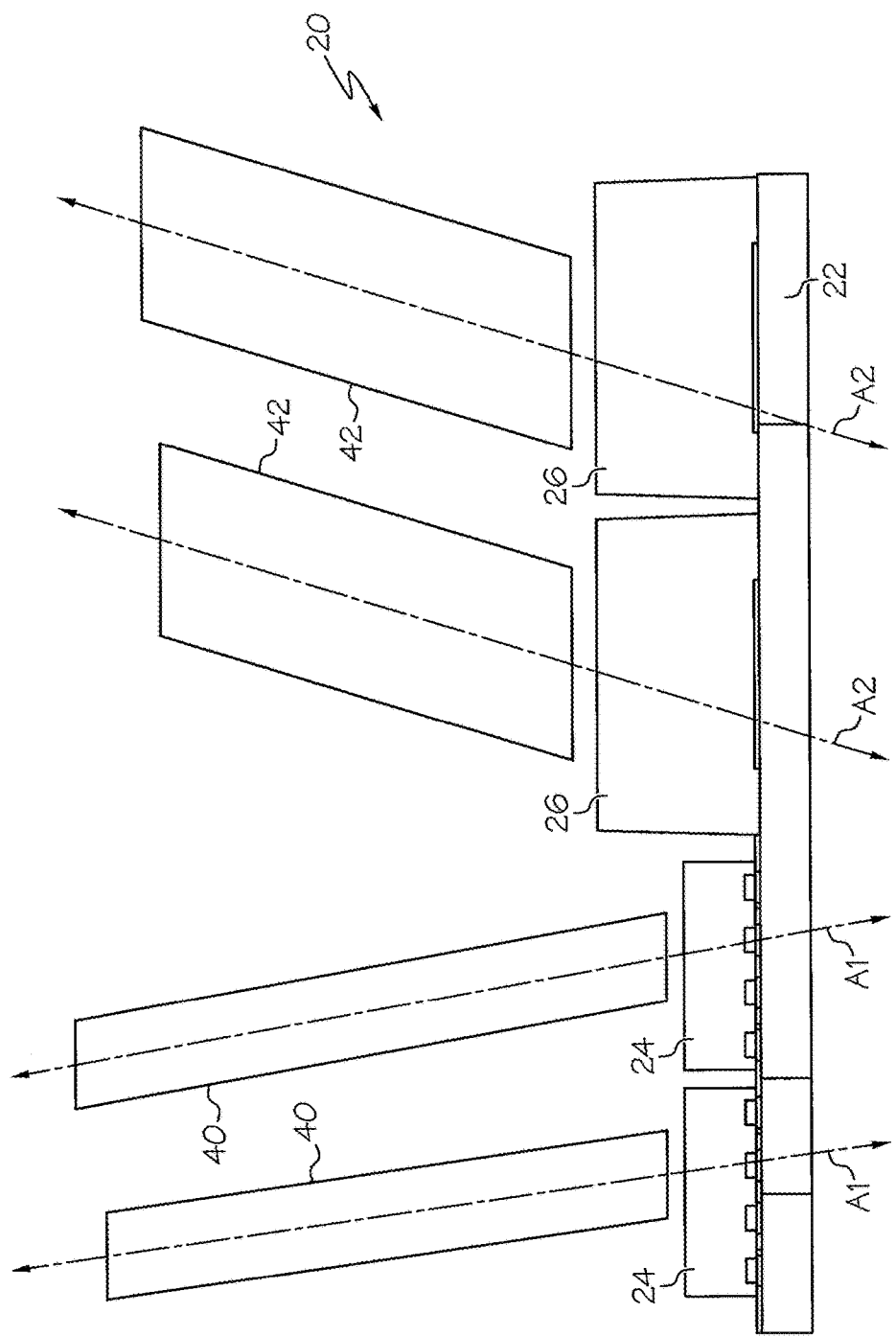
FIG. 4 is a side section view of an optical sensor module having multiple light guides, according to some embodiments of the present invention.

Referring to FIG. 4, a sensor module 20, according to some embodiments of the present invention, may include multiple optical sources 24 and/or multiple optical detectors 26 and, as such, multiple light guides 40, 42 may be utilized. In the illustrated embodiment of FIG. 4, a respective light guide 40 is in optical communication with each of the two optical sources 24, and a respective light guide 42 is in optical communication with each of the two optical detectors 26. The light guides 40, 42 each have respective axial directions $A_1, A_2$ that diverge outwardly, as discussed above with respect to FIG. 2. Although FIG. 4 shows light guide arrays are aligned in line with respect to each other, it should be understood that the arrays of light guides may be distributed across a common plane or even in multiple planes, and a linear array is not required for embodiments of the present invention.

Figure 5:
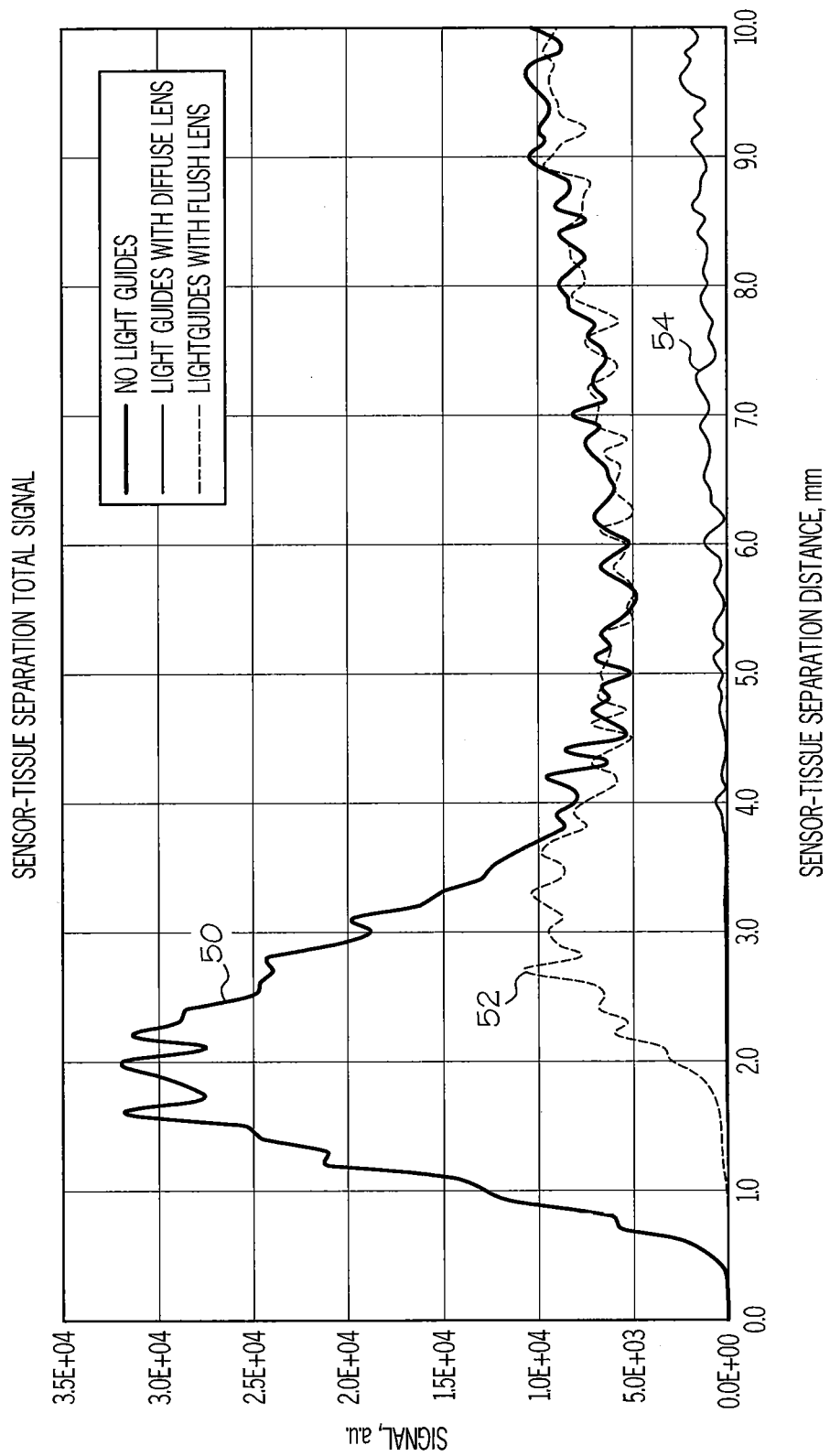
FIG. 5 is a graph illustrating the effect on an optical signal from a sensor module as a function of distance of the sensor module from the body of a subject wearing the sensor module.

FIG. 5 illustrates how effective a sensor module, such as the sensor module 20 of FIG. 2, may be in reducing the effect of noise as a result of movement of the sensor module 20 relative to the body B of a user. The separation distance between sensor module housing outer surface 32 and the body of a user B is represented by $D_1$ in FIG. 2, and is plotted along the "X" axis of FIG. 5. The signal detected by the optical detector 26 is plotted along the "Y" axis of FIG. 5 and varies with the distance $D_1$. The signal is shown in FIG. 5 based on this separation distance (Sensor-tissue separation distance, mm). When a conventional sensor module with no light guides is used, the signal onset with small separation distances is abrupt (namely, the slope is higher), leading to a substantial amount of motion artifact noise in the physiological signal (represented by curve 50). When the sensor module 20 of FIG. 2 is used with flush, non-textured light guides 40, 42, the signal onset with separation is much less abrupt (namely, the slope is lower), as illustrated by curve 52. When the sensor module 20 of FIG. 2 is used with light guides 40, 42 having respective end surfaces 40c, 42c that are textured, the signal onset with sensor-tissue separation is very slow (namely, the slope is lowest), leading to much less physiological movement-associated noise, as illustrated by curve 54. FIG. 5 illustrates the robustness of the sensor module 20 of FIG. 2 against noise in a physiological signal detected by the optical detector 26. Thus, although it is true that curve 50 shows a higher overall signal than that of curve 52 and 54, the slope of curve 50 is much higher as the sensor module separates from the skin of the user, showing that the use of light guides can reduce motion artifacts. Furthermore, generally speaking, a higher S/N as well as lower motion artifact sensitivity will result in the best performing PPG sensor modules.

Figure 6:
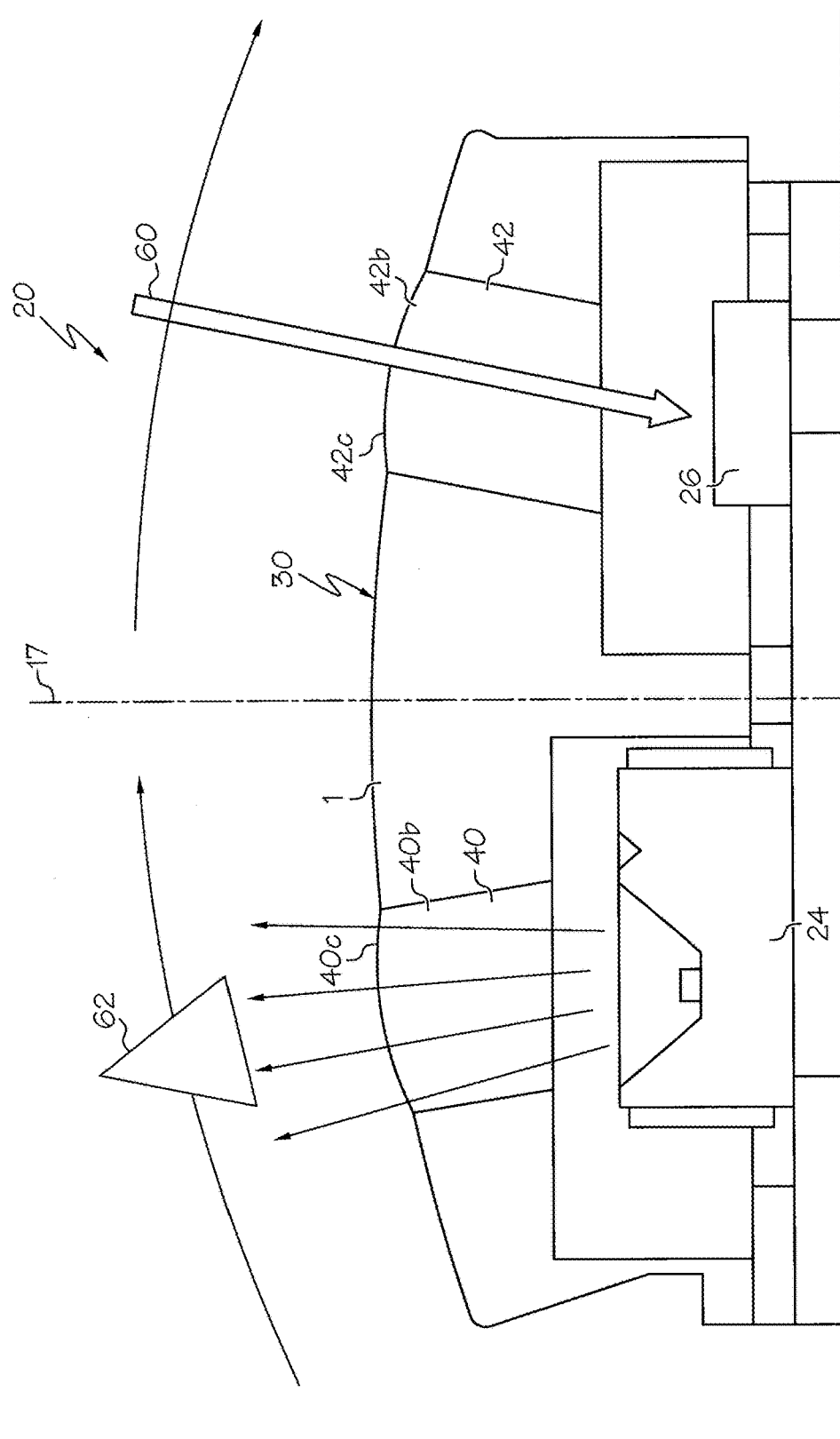
FIG. 6 is a side section view of an optical sensor module having light guides, according to some embodiments of the present invention, and illustrating a light detector being moved in an arc above the optical source and a light source being moved in an arc above the optical detector.

Referring to FIG. 6, another way to model the robustness of the sensor module 20 of FIG. 2 against physiological signal noise is to perform a "sweep test". The sweep test involves sweeping either a light source 60 over the optical detector 26 or sweeping an optical detector 62 over the optical source 24. The response signal(s) of the optical detector 24 as a function of the angle of the light source 60 is recorded and the response of the optical detector 62 as a function of the angle of the optical detector 62 is recorded.

Figure 7:
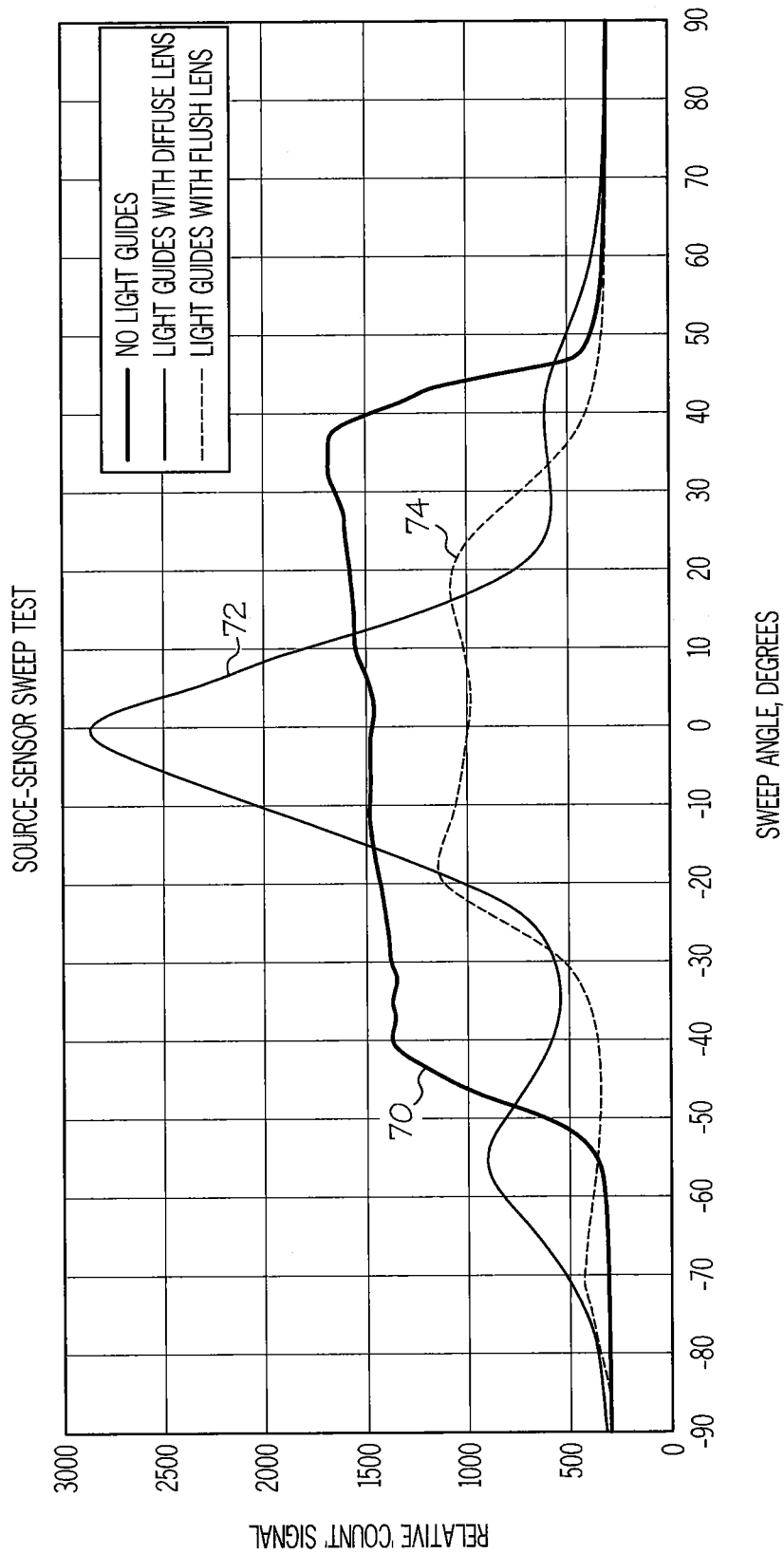
FIG. 7 is a graph illustrating the results of a sweep test as illustrated in FIG. 6 for a sensor module without light guides, for a sensor module with light guides with flush, un-textured end surfaces, and for a sensor module with textured end surfaces.

The result of such a sweep test is illustrated in FIG. 7 for a sensor module without light guides, for a sensor module, such as sensor module 20 (FIG. 2) with light guides with flush, un-textured end surfaces 40c, 42c, and for a sensor module, such as sensor module 20 (FIG. 2) with textured end surfaces 40c, 42c. In FIG. 7, sweep angle in degrees is plotted along the "X" axis, and signal response is plotted along the "Y" axis. In FIG. 7, zero degrees (0°) represents a direction normal ("normal direction") to the planes $P_1, P_2$ of the surfaces of the optical source 24 and the optical detector 26. Similarly, thirty degrees (30°) in FIG. 7 represents an angle that is 30° between the "normal direction" and the emission angle of the light source used for the sweep test. As can be seen with the recorded signal vs. sweep angle, the signal has a much gentler onset with sweep towards the normal (i.e., 0°) with light guides (in this case the light guides may be referred to as "light pipes") 40, 42 having textured end surfaces 40c, 42c, as represented by curve 70, and with light guides 40, 42 with flush, un-textured end surfaces 40c, 42c, as represented by curve 74. Within the angle of interest, which are the angles of about ±30°, the signal onset is much steeper without the use of light guides, as represented by curve 72. This steep onset in signal is a source of motion-artifact noise that can be remedied by the use of light guides, according to embodiments of the present invention. Note that in FIG. 7 the total overall signal is highest without light guides, but because the change in signal with angle is so high, the ultimate S/N ratio favors using light guides. This is because the noise ($N_m$) resulting from motion artifacts can be many times that of the PPG signal associated with biometrically modulated light.

Figure 8:
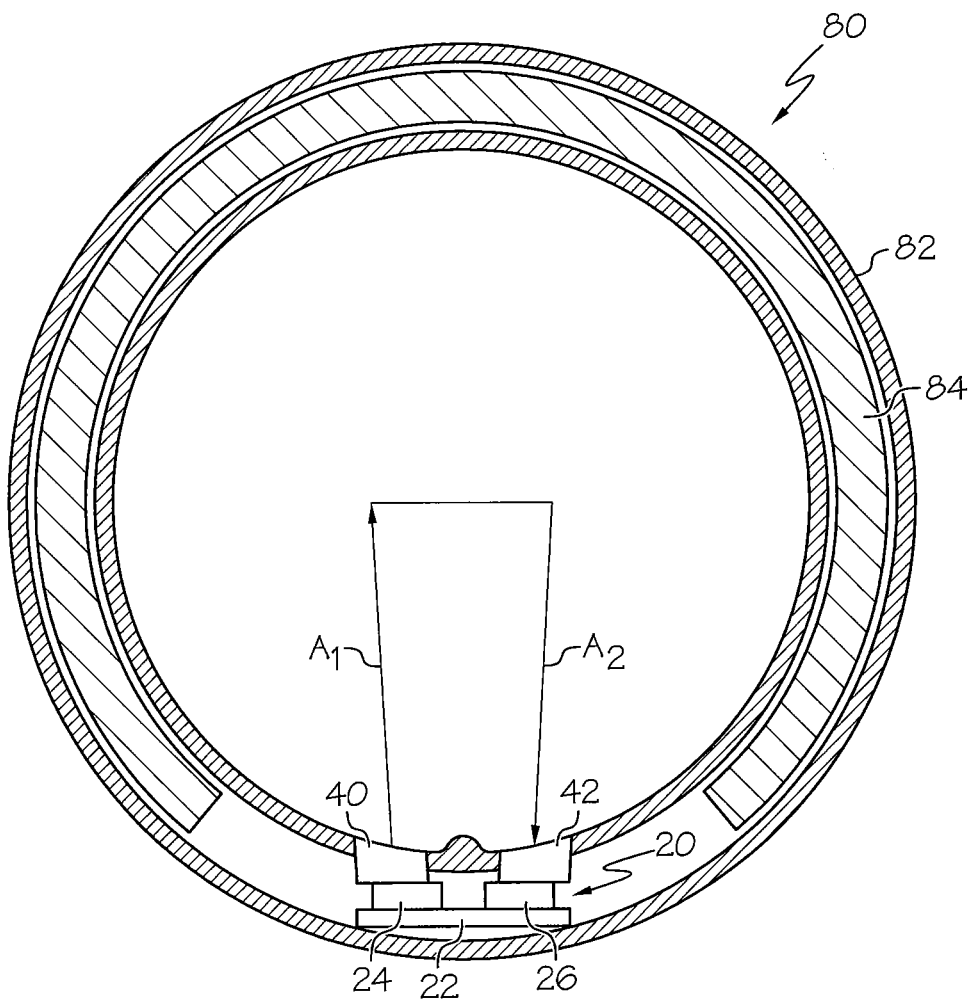
FIG. 8 is a cross sectional view of a ring incorporating an optical sensor module according to some embodiments of the present invention.

FIG. 8 illustrates an embodiment of the sensor module 20 of FIG. 2 incorporated into a ring device 80 that is configured to be worn around a digit of a user, according to some embodiments of the present invention. The light guides 40, 42 of the sensor module 20 are angled away from each other to prevent the overlap of light rays leaving the optical source 24 from directly entering the optical detector 26. A battery (e.g., a flexible battery) 84 is located within the band 82 of the ring device 80 to provide electrical power to the sensor module 20.

It should be noted that the sensor module 20 may be integrated into the ring device 80 in additional ways in accordance with embodiments of the present invention. For example, the sensor module 20 may be partially within the ring device 80 rather than wholly within the ring device 80 as shown in FIG. 8. Additionally, the light guides 40, 42 may extend or partially extend the length of the outer-inner diameter length (the length that is the difference between the outer and inner diameter of the ring device 80) or the light guides 40, 42 may protrude from the ring device 80 itself. Additional configurations may be used where the light guides 40, 42 direct light at angles relative to each other (e.g., angles a1 and a2 illustrated in FIG. 2). Also, it should be noted that the ring device 80 may be used for not only a finger ring but for any appendage or rounded form-factor, such as a digit or limb, such as a toe, arm, wrist, leg, a neck, a waist, and the like. The strap or band 82 may have different sizes and/or shapes depending on the location of donning (i.e., the location on the body of a subject where the device 80 is worn).

Figure 9A:
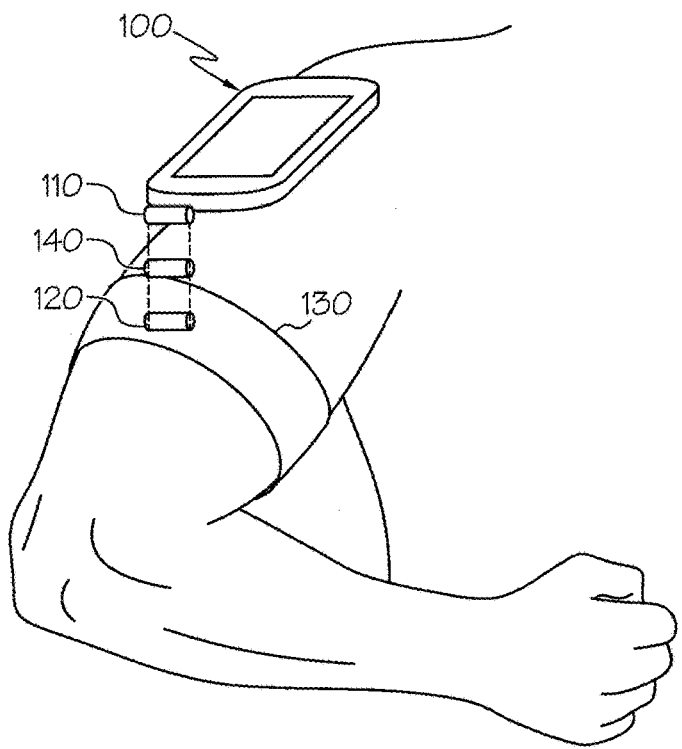
FIG. 9A illustrates an optical sensor module integrated within a mobile device and that is configured to engage an optical module worn by a user, according to some embodiments of the present invention.
Figure 9B:
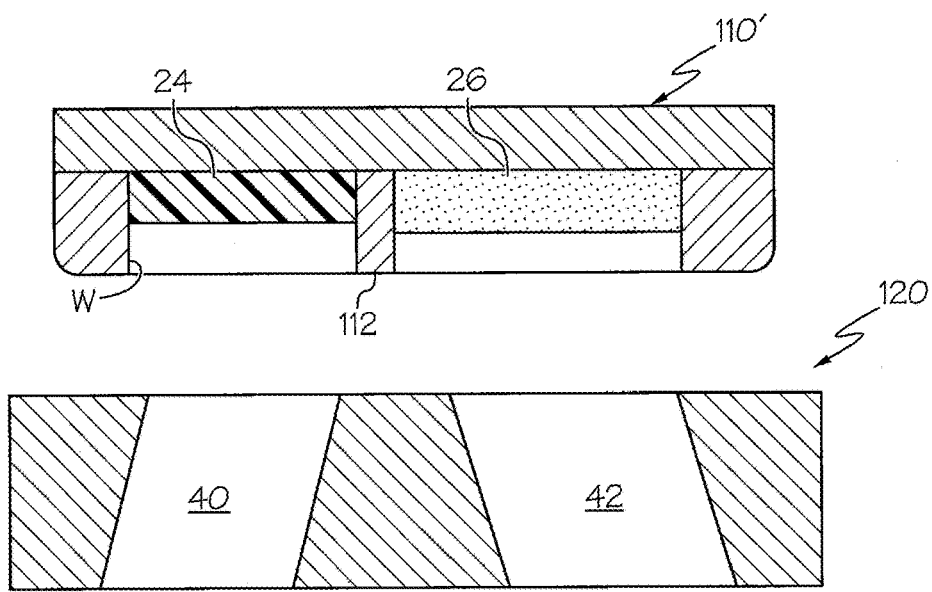
FIG. 9B is a side section view of the optical sensor and optical module of FIG. 9A prior to the optical sensor engaging the optical module.

Referring to FIGS. 9A-9B, 10A-10B, and 11A-11B, embodiments of the present invention utilizing a smartphone 100 or other mobile or electrical device are illustrated. The illustrated smartphone 100 includes an optical sensor module 110 that is in proximity to, or integrated within, the camera optics of the smartphone 100 or another optical emitter/detector already on the smartphone 100. The optical sensor module 110 is coupled to an optical module 120 in a wearable structure 130 (such as an armband, wristband, leg band, ring, etc.). This embodiment can be useful for the case when electronics are not desired to be within the wearable structure itself—for example, optical module 120 may be optics within a phone armband strap, where the smartphone 100 may contain all the electronics but may not have the optomechanics for biometric monitoring itself. The optical sensor module 110 may have light guides within it or it may not. For example, as illustrated in FIG. 9B, the optical module 110' includes only a single window W with perhaps a barrier 112 between the optical source 24 and the optical detector 26. The barrier 112 may protrude all the way to the surface of the window W or it may be shorter. The benefit of having the barrier 112 protrude to the surface of the window W is that doing so may reduce or eliminate crosstalk between the optical source 24 and optical detector 26.

The illustrated optical modules 110, 120, 140 include light guides 40, 42 as described above with respect to the sensor module 20 of FIG. 2. When the optical modules 110 and 120 (and 140, when utilized) are in alignment (as expressed by the dotted lines in FIG. 9A), light (e.g., from the flash associated with the camera of the smartphone 100) can be coupled from the smartphone 100 to the body of the person and back from the body to the smartphone 100, such that stable optical monitoring of the body can be achieved. The light guides 40, 42 in the optical module 120 may be configured to be adjacent or proximate to the skin of a user and may be angled away from each other to prevent the overlap of light rays leaving the optical sources 24 and directly entering the optical detectors 26, as described above.

Figure 10A:
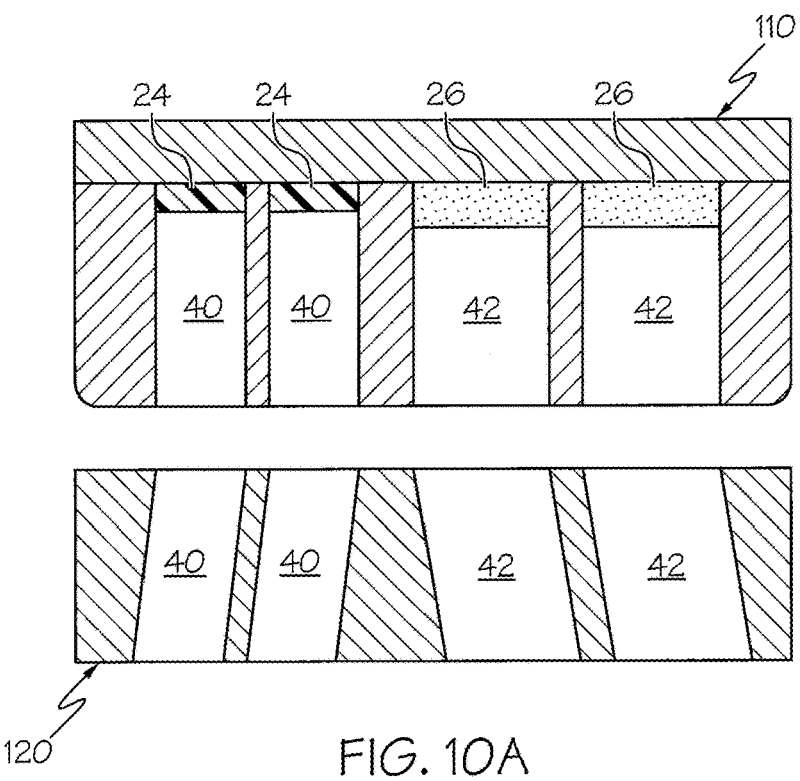
FIGS. 10A-10B are side section views of an optical sensor module and an optical module, according to other embodiments of the present invention.
Figure 10B:
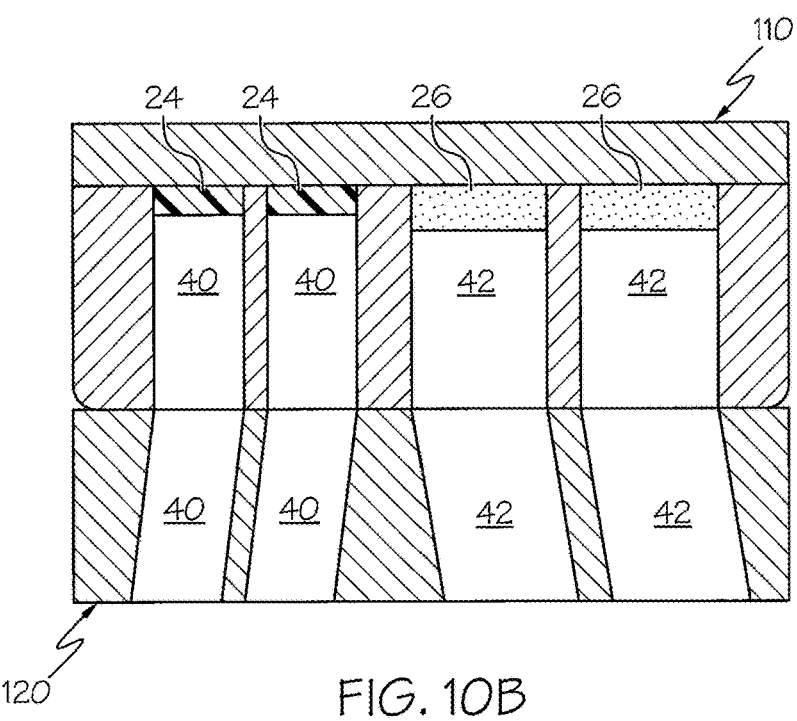

In the embodiment illustrated in FIGS. 10A-10B, the optical module 120 has multiple light guides 40, 42 that align with a respective multiple light guides 40, 42 of the sensor module 110. The light guides 40, 42 of the sensor module 110 are substantially orthogonal to the respective optical emitters 24 and optical detectors 26, as illustrated. However, the light guides 40, 42 of the optical module 120 are angled such that they diverge from each other, as illustrated. This angled configuration of the light guides 40, 42 in the optical module 120 prevents most or all light from the optical sources 24 from directly reaching the optical detectors 26 without first passing through a portion of the body of a user.

Other coupling configurations and light-guiding configurations for the optical module 120 may be used in embodiments of the present invention, and the light guides of the module 120 do not need to be angled as shown in FIGS. 10A-10B. However, the benefits of angling have been disclosed herein. Additionally, the light guides 40, 42 may be cylindrical, oval, or elliptical (i.e., have circular, oval, or elliptical cross-sections) to prevent unwanted scattering at the edges. However, having light-guiding cross-sections with "sides" or "angles", such as the case for polygonal light guide cross-sections, may be useful for matching the coupling between the modules 110 and 120.

A benefit of the configuration presented in FIG. 9A is that the optical module 120 may reside in a wearable band (or apparel item) 130 without any need for supporting electronics or battery power in the wearable band 130, as the optical emission and detection may take place via the electronics/optics of the electrical device 100 (such as a smartphone, smartwatch, smartearbud, smartsensor, or other electrical apparatus that is light-weight enough to be attached to and worn on the body of a person). The wearable band 130 may be a ring, an armband (as shown), wristband, legband, neckband, or any band or apparel item such as an item of clothing (shirts, socks, under-garments, etc.) that can be worn along the body but which can also support the optical module 120. Many different kinds of band materials and fabrics may be used, such as plastic, polymers, metals, rubbers, silicones, cotton, nylon, wood, or any other sturdy materials that can be worn for a period of time by subjects. However, the wearable band 130 should be stabilized along the body for accurate physiological readings to be assessed on a continuous basis. This may be achieved by using a stretchable material that can fit firmly along the body and/or by integrating a securing mechanism such as a buckle, clamp, clasp, button, etc., and/or by employing a springing or clamping method to hold both modules in place along the body, using one or more body regions for mechanical support. The optical module 120 does not need to touch the skin in order to generate physiological information, but the optical module 120 typically will perform best when stabilized with respect to the body of the subject.

An additional benefit of the configuration shown in FIG. 9A is that the configuration allows for novel biometric sensing use cases via selective biometric analysis. Namely, if the electrical device 100 is configured to have optics 110 that comprises both a camera module (such as smartphone CCD camera optics, for example) as well as PPG module (such as an optical emitter and an accompanied optical detector), and a processor communicating with both the camera module and the PPG module, then advanced biometric sensing may be achieved, such as selective biometric analysis. In this methodology, images of the body of the subject may be collected and analyzed by the processor with respect to blood flow as sensed by the PPG module. For example, the processor may identify the frequency of blood flow (i.e., the frequency relating to the heart rate or breathing rate) via sensor data from the PPG module and may analyze images sensed by the camera module with respect to this frequency. In this method, pixels that are changing at the same rate (or approximate same rate) as the blood flow frequency may be selectively amplified with respect to pixels that are not changing at this rate (raising the effective contrast). In this way, blood vessels (arteries, veins, arterioles, capillaries, and the like) may be selectively analyzed to generate biometric assessments, even in noisy environments.

According to some embodiments of the present invention, the process can be executed in reverse such that regions of the body that do not substantially modulate with blood flow may be selectively amplified with respect to regions that do modulate with blood flow. These more static regions (such as certain tissue regions comprising bone, skin, tendons, etc.) may then be selectively analyzed.

The above-described selective amplification may be further enhanced by incorporating active motion-artifact removal by using a motion sensor (such as an accelerometer or other motion sensor) in physical communication with the body, smart device 100, and/or wearable band as a noise reference such that the processor, in communication with the motion sensor, is able to selectively remove or attenuate frequencies associated with body motion or other unwanted motion noise. Because many smartphones and other smart devices may comprise both digital cameras and accelerometers (often having multiple axes), the processor (which may also reside in a smartphone) may have access to all of these electronics.

There are several examples of biometric assessments that may be generated by the selective amplification method described above. For example, by ratioing intensities of two (2) or more wavelengths from the selectively amplified pixels, an assessment of blood analyte along each blood vessel may be generated. An example of such blood analyte may include any optically interacting blood analyte, such as blood hemoglobin (oxyhemoglobin, deoxyhemoglobin, carboxyhemoglobin, and methemoglobin, for example), bilirubin, lactate, glucose, and the like. Numerous blood chromophores may be analyzed via this method. In the case of glucose and other blood analyte which are not chromophores, adding one or more polarizers to the optics (110, 120) may be required, as glucose and other blood constituents have been observed to preferentially scatter light at certain polarizations. As yet another example of a biometric assessment using selective amplification, a processor may analyze blood vessels along their pathways to see how they change shape with each pulse. This assessment may be used to assess vascular compliance and/or blood pressure along the vessels or to assess cardiac output by assessing these localized blood vessel changes in relation to a physical model. As yet another example of a biometric assessment using selective amplification, a processor may characterize static (not time-varying) and/or dynamic (time-varying) changes in blood vessels to generate a biometric identification of a subject. In this assessment, a processor may compare the blood vessel characterization with a known characterization stored in memory, for example, by running an algorithm to assess their similarity. A similarity above a certain threshold may then trigger an identification for a subject. It is important to note that a key aspect of embodiments of the present invention is that combining a PPG sensor with a camera affords the ability to generate a contrast between physiological properties/characteristics that modulate with blood flow and other properties/characteristics that do not substantially modulate with blood flow.

This selective amplification method may be executed with or without modulating the PPG sensor light source (the optical emitter) or with or without polling the PPG detector and/or the camera. For example, a PPG sensor may be operating in a continuous mode, and PPG readings as well as camera readings may be collected continuously. Alternatively, a PPG sensor may be pulsed to generate pulses of light, or the PPG detector or the camera readings may be polled at time intervals. If multiple wavelengths are employed with the PPG sensor, then alternately modulating (i.e., pulsing) the optical emitters such that only one emitter is on at a time may help differentiate the PPG signals for each wavelength. However, this effect may also be achieved by continuously emitting all optical emitting wavelengths and differentiating signals from each wavelength via optical filters on the camera and/or the optical detector(s) of a PPG sensor. For example, the optical detectors of a PPG sensor may each comprise one or more optical filters to pass only certain wavelengths of light and the camera may comprise optical filters and/or may comprise beam-splitting optics to direct certain optical wavelength ranges to certain light-detecting regions of the camera.

In some embodiments, an optomechanical coupler 140 (FIGS. 9A and 11A-11B) can be used to interface between optical sensor module 110 and optical module 120 such that the two optical modules 110, 120 can be matched or to provide additional stability between the smartphone optical module 110 and the band optical module 120. This may be advantageous where a smartphone 100 has native optomechanics 110 (such as the optics used for a photographic camera and/or optics used to measure heart rate) that may not directly match with the optomechanics of the band 120. In this case, the coupling optomechanics 140 can be used to translate between the optics 110 and 120.

Figure 11A:
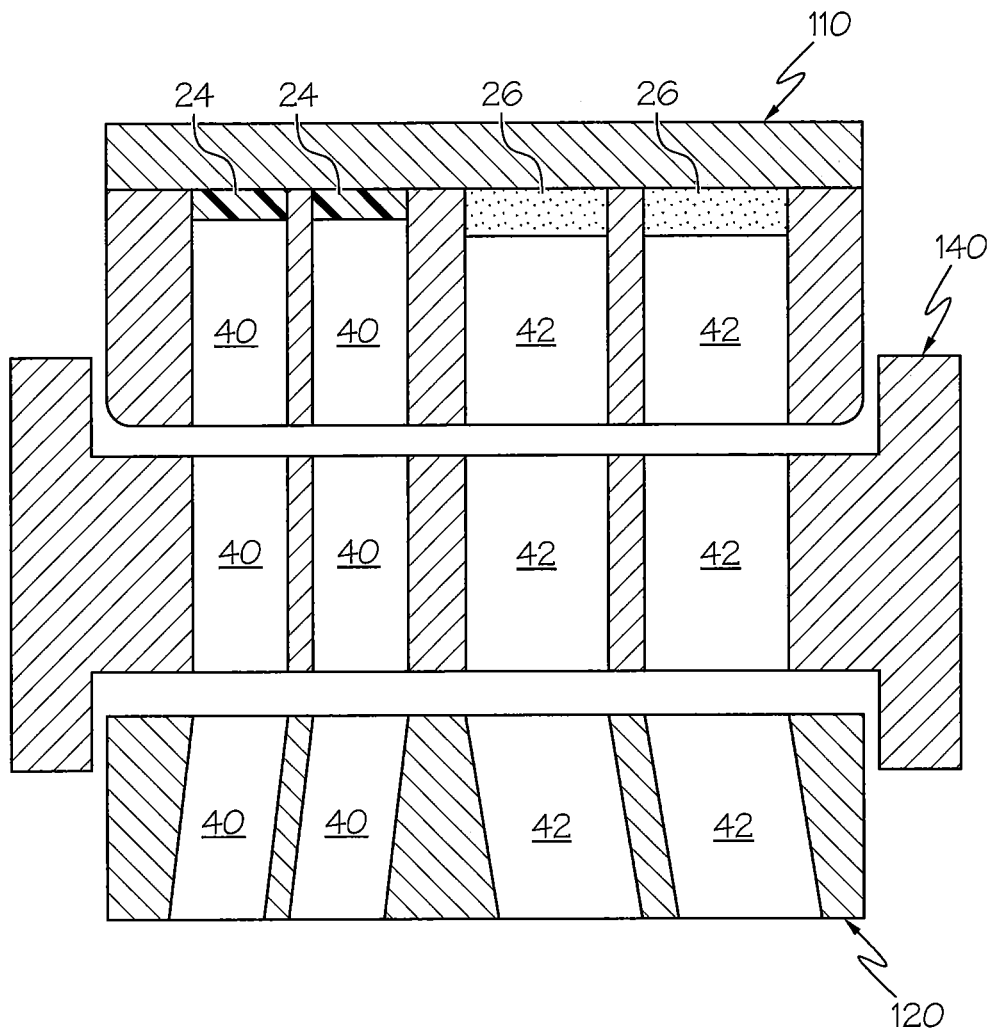
FIG. 11A is a side section view of an optical sensor module, an optical module, and an optical coupler therebetween, according to some embodiments of the present invention.
Figure 11B:
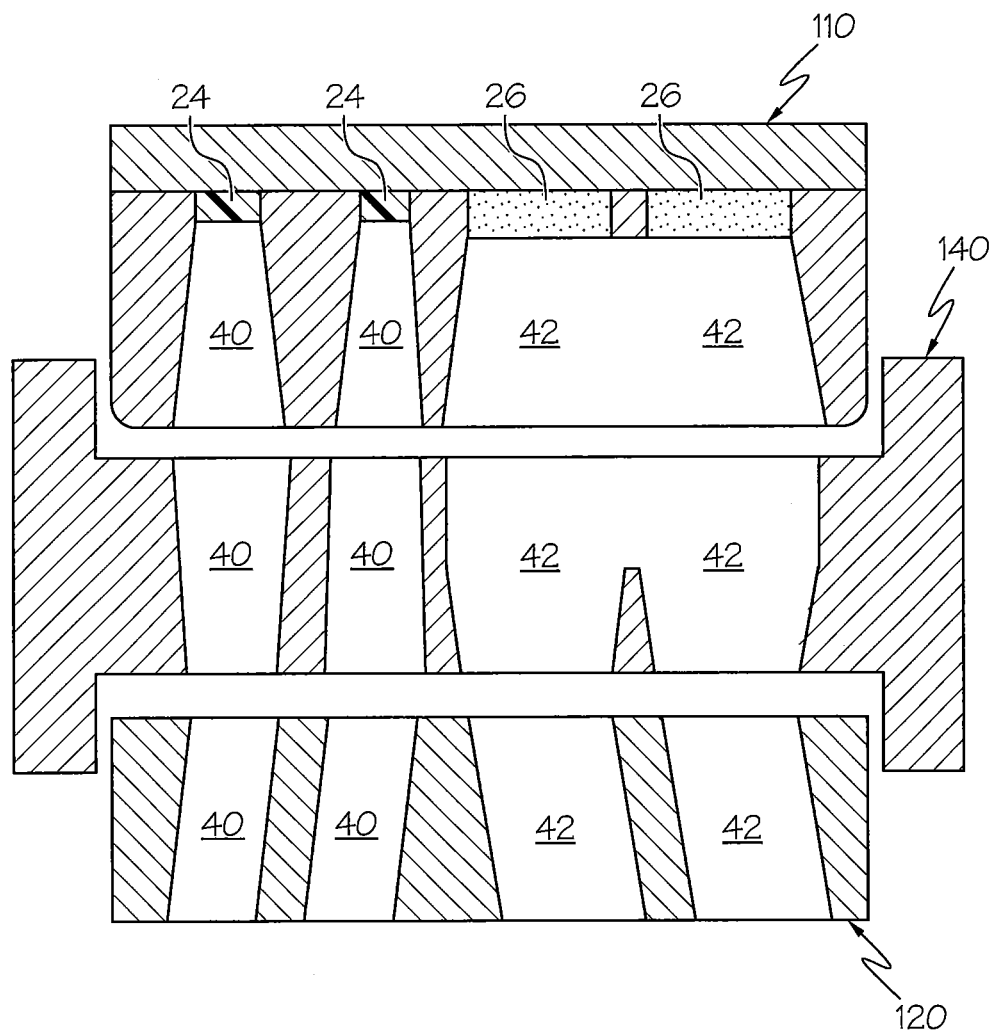
FIG. 11B is a side section view of an optical sensor module, an optical module, and an optical coupler therebetween, according to some embodiments of the present invention.
Figure 12B:
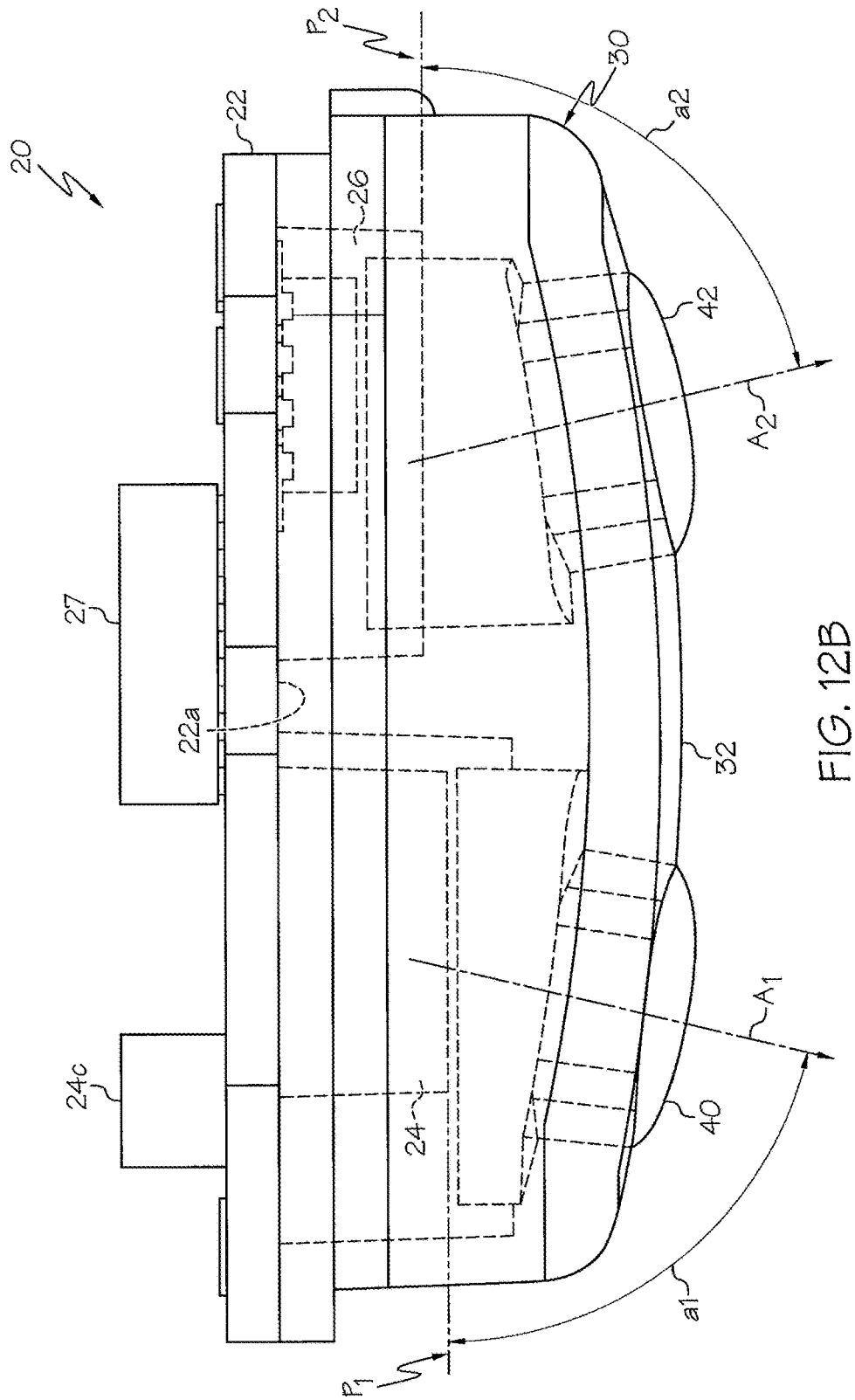
FIG. 12B is a side view of the optical sensor module of FIG. 12A illustrating the light guides therein angled away from each other.
Figure 12F:
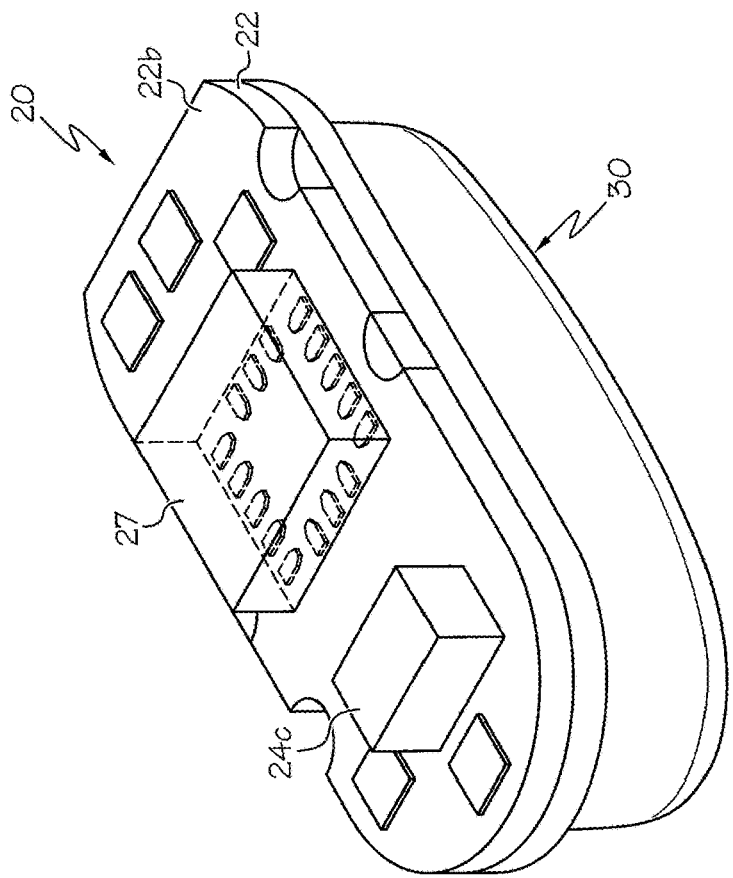
FIG. 12F is a rear perspective view of the optical sensor module of FIG. 12A.
Figure 12E:
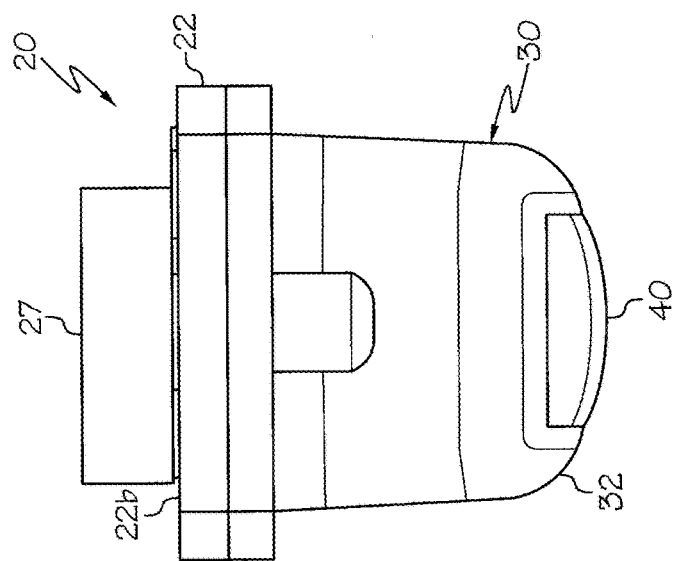
FIG. 12E is an end view of the optical sensor module of FIG. 12A.
Figure 13A:
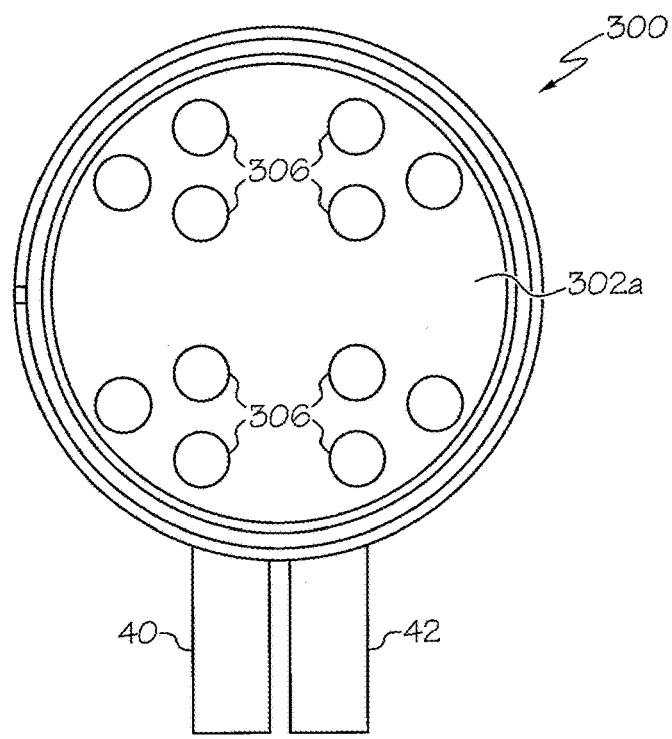
FIG. 13A is a front view of an earbud speaker driver with integrated optomechanics, according to some embodiments of the present invention.
Figure 13B:
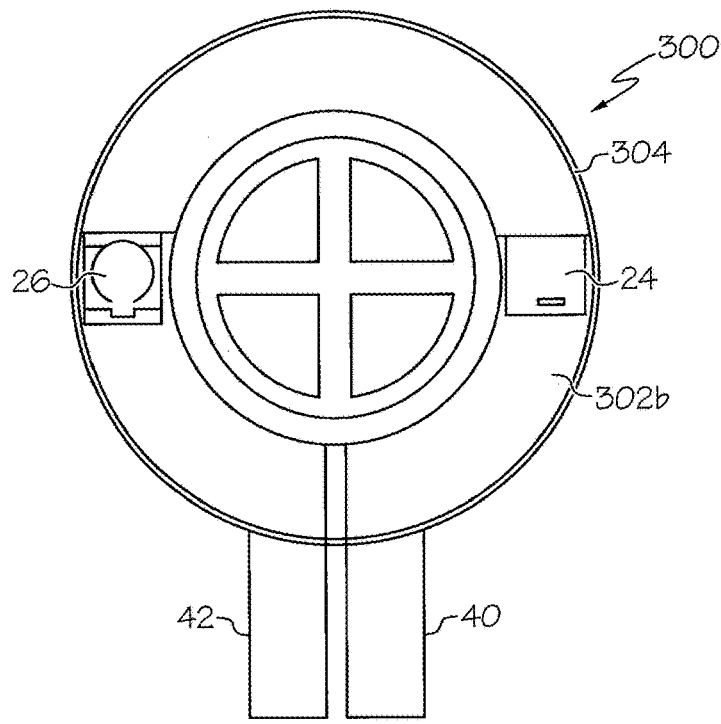
FIG. 13B is a rear view of the earbud speaker driver of FIG. 13A.
Figure 13C:
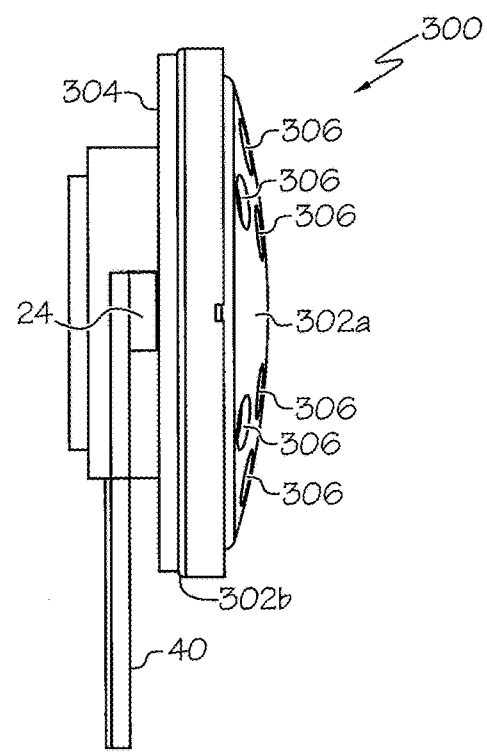
FIG. 13C is a side view of the earbud speaker driver of FIG. 13A.
Figure 13D:
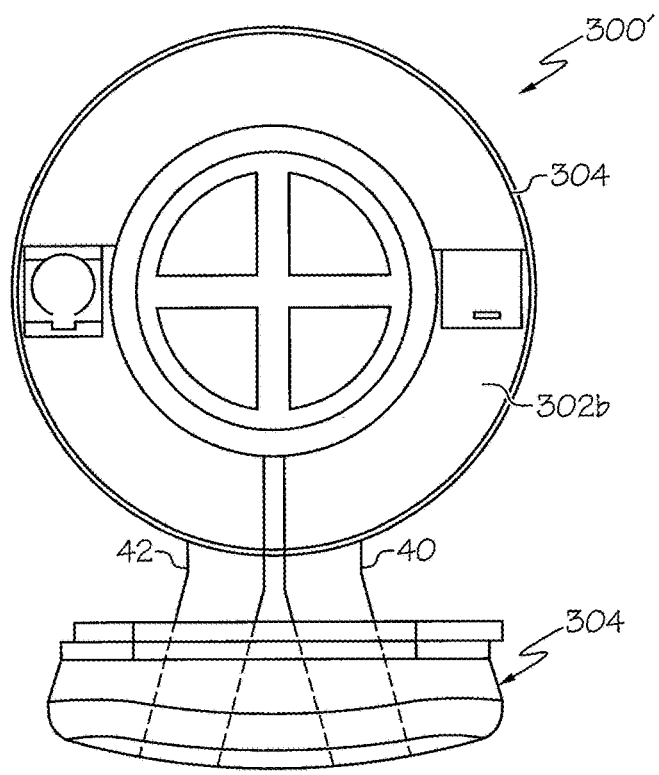
FIG. 13D is a rear view of the earbud speaker driver of FIG. 13A with the light guides coupled to a sensor module, according to some embodiments of the present invention.

In the embodiment illustrated in FIG. 11A, the optomechanical coupler 140 has light guides 40, 42 with a similar shape and configuration as the sensor module 110. In the embodiment illustrated in FIG. 11B, the coupler 140 has light guides 40, 42 with shapes at one end that conform with shapes of the light guides 40, 42 of the sensor module 110, and with different shapes at the opposite end that conform with shapes of the light guides 40, 42 of the optical module 120. The coupler 140 is designed to couple with the optics on a smart device (illustrated as a smartphone 100 in FIG. 9A) and the optics in the wearable sensor (130, FIG. 9A). As such, a user can utilize a separate coupler 140 for each smartphone or other device that they use, since each smartphone/device may be manufactured using different optics.

FIGS. 12A-12F illustrate another style of the optical sensor module 20 of FIG. 2 that can be used with various wearable monitoring devices, such as earbud monitoring devices. The illustrated sensor module 20 includes a substrate or base 22 (e.g., a circuit board, etc.) having an optical source 24 and an optical detector 26 on one side 22a thereof. The base 22 may support and/or be connected to various electronic components including, but not limited to, a signal processor, a wireless module for communicating with a remote device, a memory storage device, etc. Moreover, a battery, such as a lithium polymer battery or other portable battery, may be mounted to or connected to the base 22 and may be charged via a charge port, such as a USB charge port for example. Additionally, the base 22 may be flexible, rigid, or a combination of flexible and rigid material, or various other base constructs suitable for supporting electronics. The base 22 may comprise one piece or a plurality of pieces. In the illustrated embodiment, a capacitor 24c for driving the optical source 24 and an accelerometer 27 are mounted to an opposite side 22b of the base 22.

The optical source 24 may be one or more light-emitting diodes (LED), laser diodes (LD), compact incandescent bulbs, micro-plasma emitters, IR blackbody sources, or the like. The optical detector 26 may be one or more photodiodes, photodetectors, phototransistors, thyristors, solid state devices, optical chipsets, or the like.

A housing 30 is secured to the base 22 and overlies the optical source 24 and optical detector 26. The illustrated housing 30 has a curved outer surface 32 that is configured to engage a particular portion of the body of a user wearing a device incorporating the sensor module 20. For example, although the sensor module 20 may be integrated into numerous wearable form-factors that afford proximate location of the sensor module to the skin of the user, in some embodiments, the sensor module 20 may be incorporated into an earbud and the housing outer surface 32 is contoured to matingly engage a particular region of the ear (e.g., the region between the anti-tragus and the concha, the region along the helix or anti-helix of the ear etc.). However, the housing outer surface 32 may have various shapes and configurations and need not be curved. For example, a wristband module applying the invention may have a flat housing outer surface 32.

The housing 30 includes a first light guide 40 in optical communication with the optical source 24 and a second light guide 42 in optical communication with the optical detector 26. In addition to supporting the first and second light guides 40, 42, the housing 30 may be configured to enclose and protect the various electronic components mounted to the base 22 from ambient interference (air, humidity, particulates, electromagnetic interference, etc).

The first light guide 40 defines a first axial direction $A_1$, and the second light guide 42 defines a second axial direction $A_2$. The first axial direction $A_1$ of the first light guide 40 has an angle a1 relative to a plane $P_1$ defined by a surface of the optical source 24 that is less than ninety degrees (90°), and the second axial direction $A_2$ of the second light guide 42 has an angle a2 relative to a plane $P_2$ defined by a surface of the optical detector 26 that is less than ninety degrees (90°). As such, the first and second light guides 40, 42 are positioned within the housing 30 such that they diverge outwardly from the housing 30.

Referring now to FIGS. 13A-13D, an earbud speaker driver 300 with integrated optomechanics, according to some embodiments of the present invention, is illustrated. The speaker driver 300 has opposite front and rear portions 302a, 302b. As understood by those skilled in the art, sound is emitted through apertures 306 formed in the front portion 302a of the speaker driver 300. An optical source 24 and optical detector 26 are supported by a printed circuit board (PCB) 304 on the rear portion 302b of the speaker driver 300. Light guides 40, 42 couple from the optical source 24 and optical detector 26 to a select region of the ear. In one particular embodiment, the light guides lead to a sensor module that may be placed between the anti-tragus an concha of the ear, such as the sensor module 304 in FIG. 13D. The light guides 40, 42 may lead to any region of the ear, such as the ear canal, tympanic membrane, earlobe, helix, anti-helix, tragus, behind the ear, temple, etc.

A key benefit of the illustrated speaker driver 300 of FIGS. 13A-13D is that all the sensor electronics may be integrated into a compact speaker driver or speaker driver assembly, rather than dispersed throughout an earbud, and the light guiding may be used to couple from the speaker driver 300 to numerous locations of the ear. Additional sensor electronics and light guiding may also be located on the speaker driver 300. For example, the PCB 304 may support an accelerometer, humidity sensor, altimeter, proximity sensor, temperature sensor, etc. Moreover, the PCB 304 may house a temperature sensor coupled to a light guide that directs black body radiation from the tympanic membrane to the temperature sensor. In this case, the temperature sensor may preferably comprise at least one thermopile and one thermistor.

FIG. 14 is an illustration of a human ear E with various portions thereof labeled. FIGS. 15-17, 18A-18B, 19, 20, 21A-21B and 22A-22B show various embodiments of speaker drivers 300 integrated with biometric sensors or both biometric sensors and light guides. It should be noted that the speaker drivers 300 may be integrated within earbuds or other earpieces, or other headwear, but the earbuds are not shown to promote clarity of the invention and to highlight the fact that the speaker drivers 300 may be integrated into a variety of different earbuds, earpieces, headwear, and the like. Additionally, the sizes of various elements may not be to scale. For example, light guides (e.g., 40, 42, FIGS. 17, 19) may be shown smaller, larger, differently shaped than may be in an actual device in order to help present certain aspects of the invention more clearly in the figures.

Figure 15:
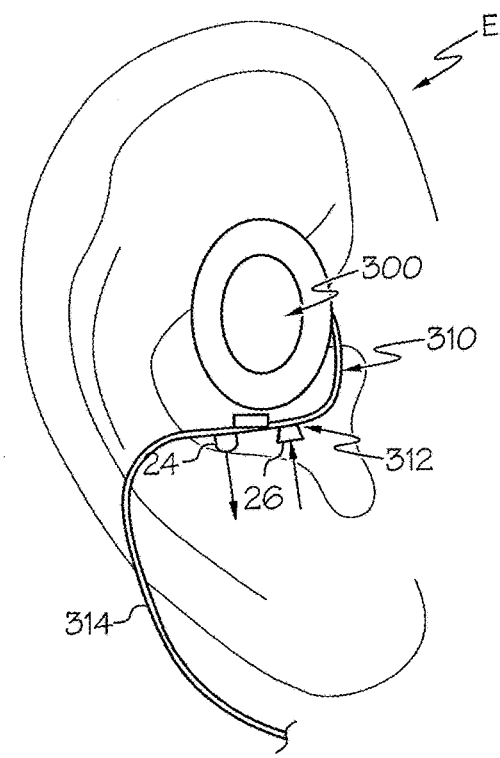
FIGS. 15-20 illustrate an earbud speaker driver positioned relative to an ear of a subject, according to various embodiments of the present invention.

In FIGS. 15-20, a speaker driver 300 is shown without an earbud housing, as the speaker driver 300 may be incorporated in a variety of earbud designs. The speaker driver 300 is shown positioned within an ear E of a subject and has a sensor circuit 312. In the embodiment illustrated in FIG. 15, the speaker driver 300 is positioned near the concha of the ear E, for example between the antihelix and the tragus of the ear E. A flex circuit (or other electrical connection medium) 310 is electrically connected to the speaker driver 300 and extends from the speaker driver 300. The flex circuit 310 supports a sensor circuit 312 that includes an optical emitter 24 and optical detector 26. The flex circuit 310 provides a signal path from/to the sensor circuit 312 and speaker driver 300. In FIG. 15, the speaker driver 300 is illustrated slightly higher in the concha than would be normal in order to be able to illustrate the sensor circuit 312.

The flex circuit 310 is configured such that sensor circuit 312 touches the skin of the ear at a region containing blood vessels, such as the concha, anti-tragus, ear canal, anti-helix, helix, earlobe, behind the ear, and the like. Performance may be best when the sensor circuit is located at the anti-tragus and/or concha, including (but not limited to) the intersection of the anti-tragus and concha of the ear E. In the illustrated embodiment, the earbud wire 314 (i.e., the electrical wire providing sound to the earbud speaker driver 300, as well as providing electrical connectivity to the sensor circuit 312) is connected to the flex circuit 310. The flex circuit 310 is configured to dampen sound vibrations from the speaker driver 300 and to provide tight coupling of the sensor circuit 312 to the skin.

Figure 16:
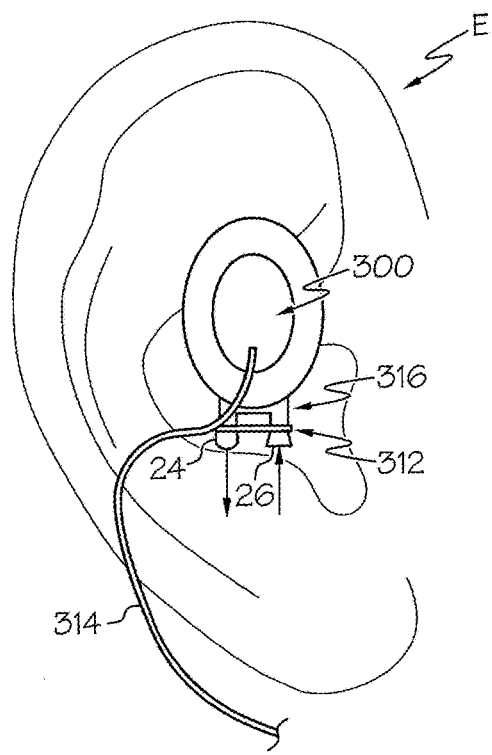

In the embodiment illustrated in FIG. 16, the speaker driver 300 is positioned near the concha of the ear E, for example between the antihelix and the tragus of the ear E. A rigid sensor circuit 312 that includes an optical emitter 24 and optical detector 26 is secured to the speaker driver 300 and is electrically connected to the speaker driver 300. In the illustrated embodiment, the sensor circuit 312 is oriented to touch the skin behind the antitragus of the ear E (the skin between the anti-tragus and concha of the ear E), but other locations of, the ear are also appropriate. Damping material 316 is positioned between the sensor circuit 312 and the speaker driver 300, as illustrated. The damping material 316 dampens sound vibrations from the speaker driver 300 and provides cushioned coupling with the skin of the ear E. In the illustrated embodiment, the earbud wire 314 is connected to the sensor circuit 310 and to the speaker driver 300. In FIG. 16, the speaker driver 300 is illustrated slightly higher in the concha than would be normal in order to be able to illustrate the light guides 40, 42 and sensor circuit 312.

Figure 17:
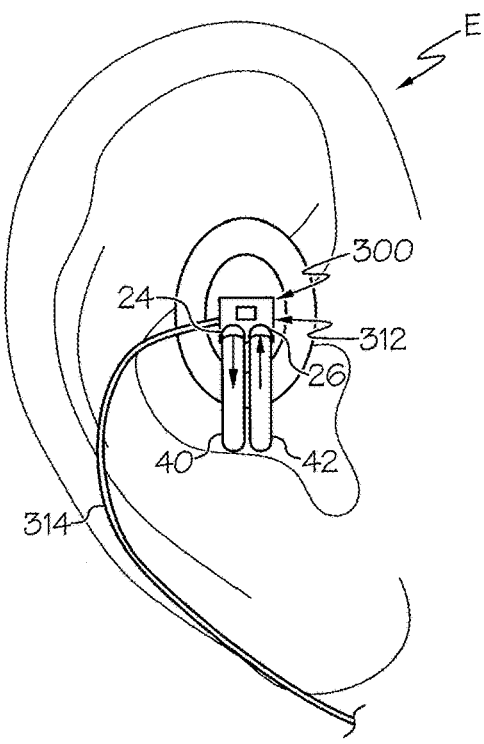

In the embodiment illustrated in FIG. 17, the speaker driver 300 is positioned near the concha of the ear E, for example between the antihelix and the tragus of the ear E. A sensor circuit 312 that includes an optical emitter 24 and optical detector 26 is secured to the speaker driver 300 and is electrically connected to the speaker driver 300. A pair of light guides 40, 42 are in optical communication with the optical emitter 24 and optical detector 26, and a distal end of each is configured to engage the skin behind the antitragus of the ear E. Light guide 40 guides light from the optical emitter into the skin and light guide 42 collects light scattered within the ear and delivers this to the optical detector 26. In some embodiments, damping material (not shown) may be positioned between the sensor circuit 312 and the speaker driver 300 to dampen sound vibrations from the speaker driver 300. In the illustrated embodiment, the earbud wire 314 is connected to the sensor circuit 310. Although only two light guides 40, 42 are illustrated in FIG. 17, it is understood that more than two light guides may be utilized.

Figure 18B:
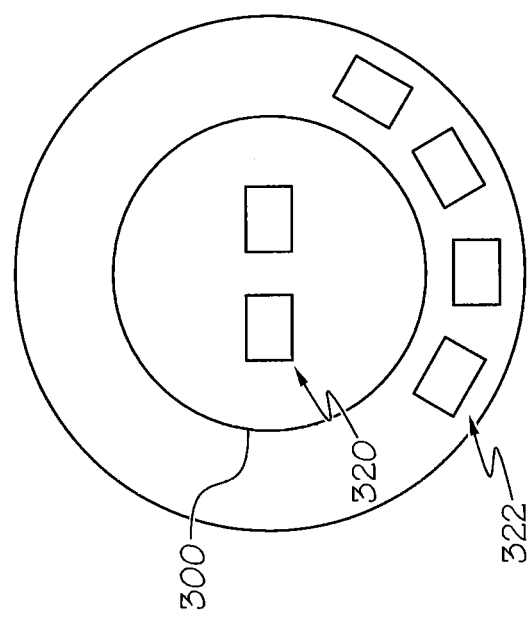
Figure 18A:
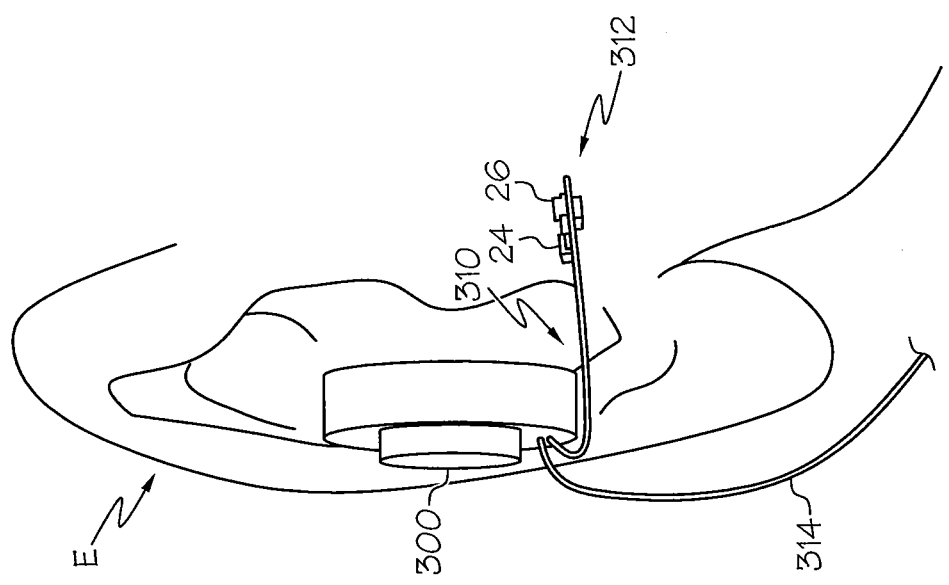

In the embodiment illustrated in FIG. 18A, the speaker driver 300 is positioned within the ear E, for example between the antihelix and the tragus of the ear E. A flex circuit 310 containing an optical emitter 24 and detector 26 is electrically connected to the speaker driver 300 and extends from the speaker driver 300 into the ear canal. The emitter 24 and detector 26 are configured to emit and detect light along the skin of the ear canal and/or the tympanic membrane. As illustrated in FIG. 18B, the speaker driver 300 includes pads 320 for electrically connecting to the speaker wire and pads for electrically connecting to the flex circuit 310.

The flex circuit supports a sensor circuit 312 that includes an optical emitter 24 and optical detector 26. The flex circuit 310 provides a signal path from/to the sensor circuit 312 and speaker driver 300. The flex circuit 310 is configured to dampen sound vibrations from the speaker driver 300 and to provide tight coupling of the sensor circuit 312 to the skin within the ear canal. In the illustrated embodiment, the earbud wire 314 is connected to the speaker driver 300.

Figure 19:
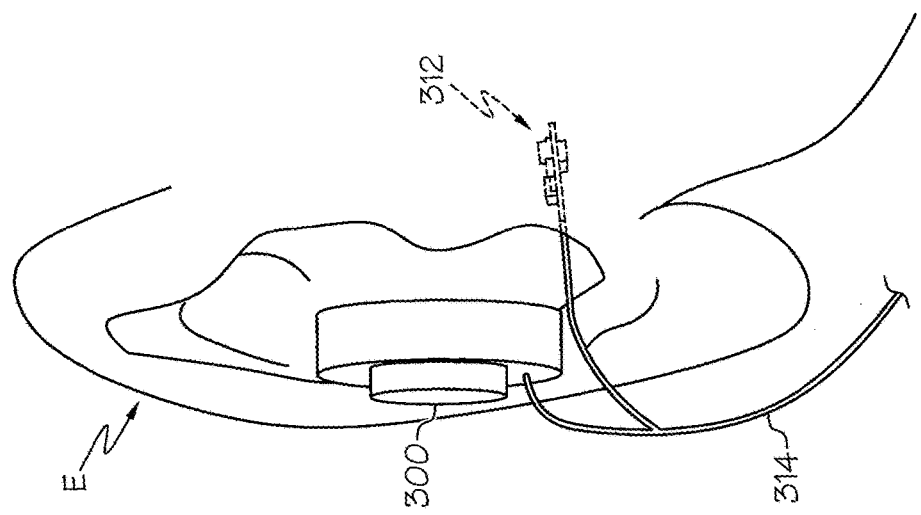

In the embodiment illustrated in FIG. 19, the speaker driver 300 is positioned within the ear E, for example between the antihelix and the tragus of the ear E. A sensor circuit 312 that includes an optical emitter 24 and optical detector 26 is secured to the speaker driver 300 and is electrically connected to the speaker driver 300. Damping material 316 is positioned between the sensor circuit 312 and the speaker driver 300 to dampen sound vibrations from the speaker driver 300. A pair of light guides 40, 42 are in optical communication with the optical emitter 24 and optical detector 26, and the light guides 40, 42 are configured to extend into the ear canal and engage the skin in the ear canal and/or the tympanic membrane. Light guide 40 guides light from the optical emitter into the ear and light guide 42 collects light scattered within the ear and delivers this to the optical detector 26. In the illustrated embodiment, the earbud wire 314 is connected to the speaker driver 300. In FIG. 19, the light guides 40, 42 are configured to direct light linearly between the emitter 24 and detector 26 and the ear E. Also, the emitter light is directed towards the concha of the ear and the detector collects light scattered by the concha of the ear.

Figure 20:
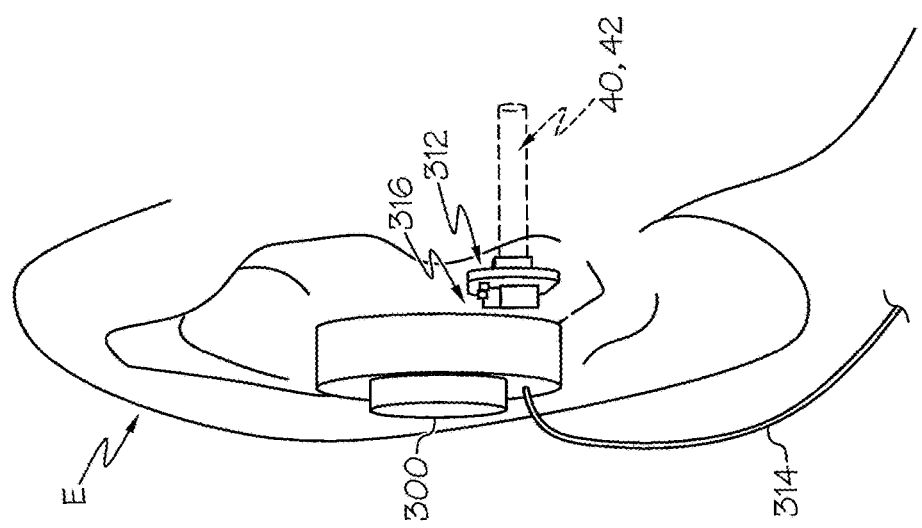
Figure 21A:
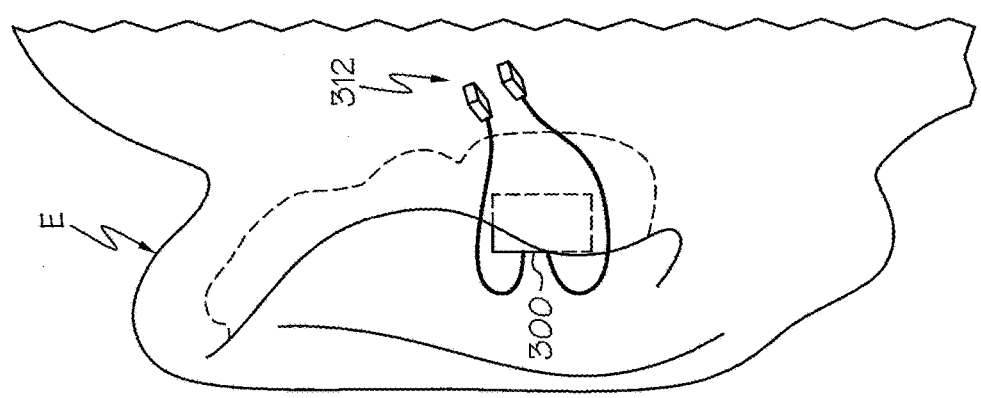
FIGS. 21A-21B and 22A-22B illustrate a speaker driver sensor, according to some embodiments of the present invention.
Figure 21B:
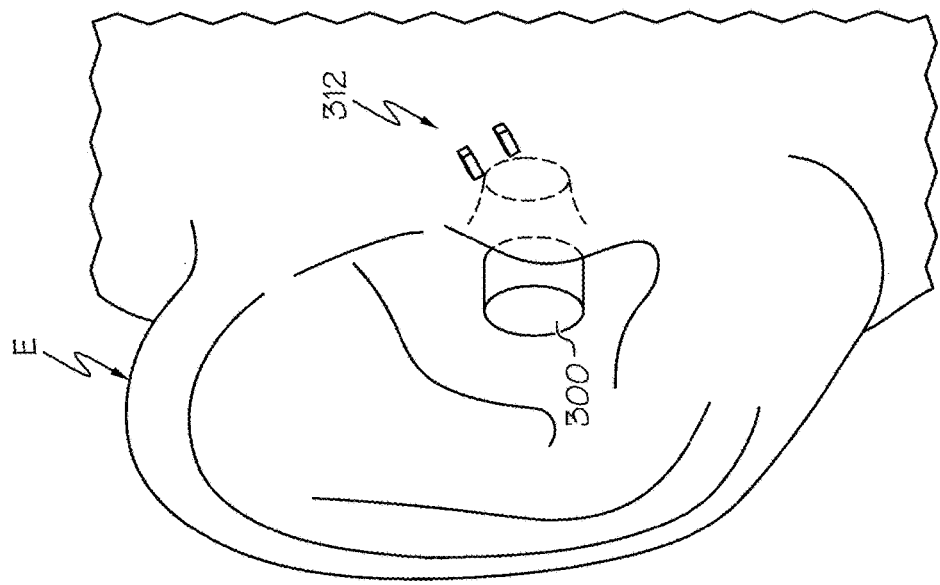

In the embodiment illustrated in FIG. 20, the speaker driver 300 is positioned within the ear E, for example between the antihelix and the tragus of the ear E. An earbud wire 314 is connected to the speaker driver 300 and to a sensor circuit 312. The sensor circuit 312 is configured to be positioned within the ear canal and includes an optical emitter 24 and optical detector 26.

Figure 22B:
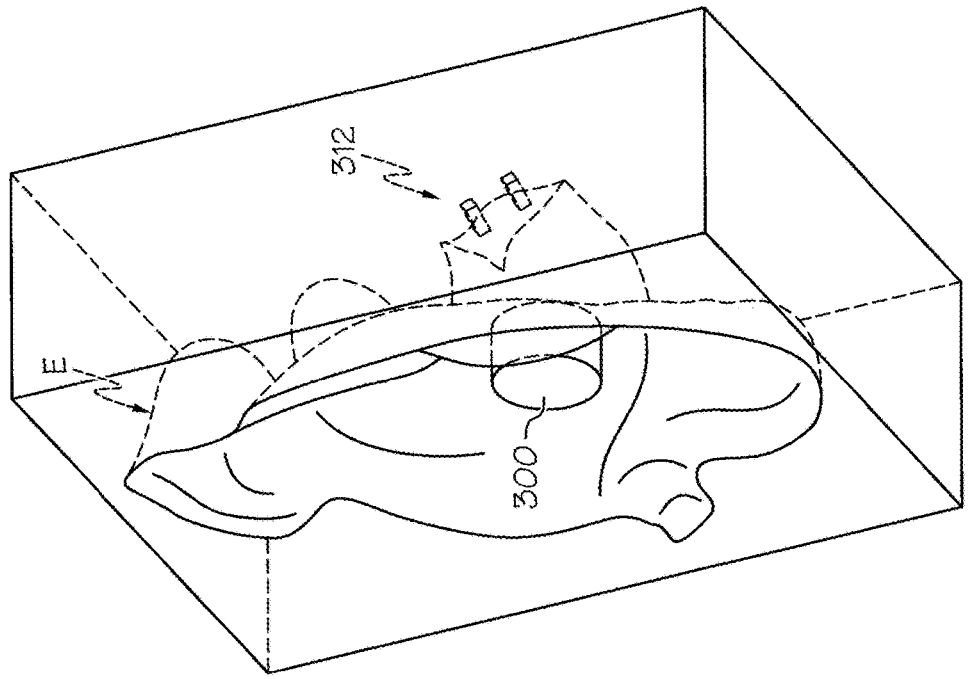
Figure 22A:
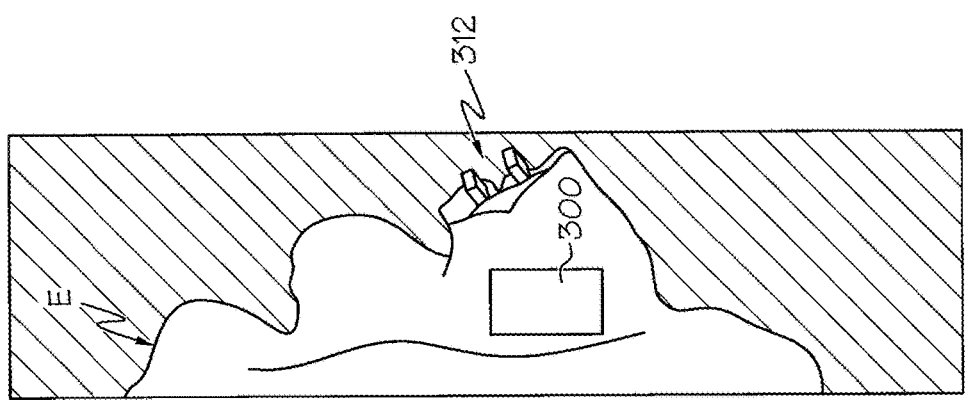

FIGS. 21A-21B and 22A-22B further illustrate the speaker driver embodiment of FIG. 20 situated near or inside the ear canal. In FIGS. 21A-21B and 22A-22B, the sensor circuit 312 is shown to be configured to be flexibly placed within the ear canal to couple with the ear canal and/or tympanic membrane. An additional flex connection or wire from the audio driver may also be available for additional sensors or actuators, such as at least one mechanical or acoustical actuator and/or microphones. In FIGS. 22A-22B, a structure or brace is shown to support the sensor circuit to keep it integrated together in the ear canal.

Figure 23:
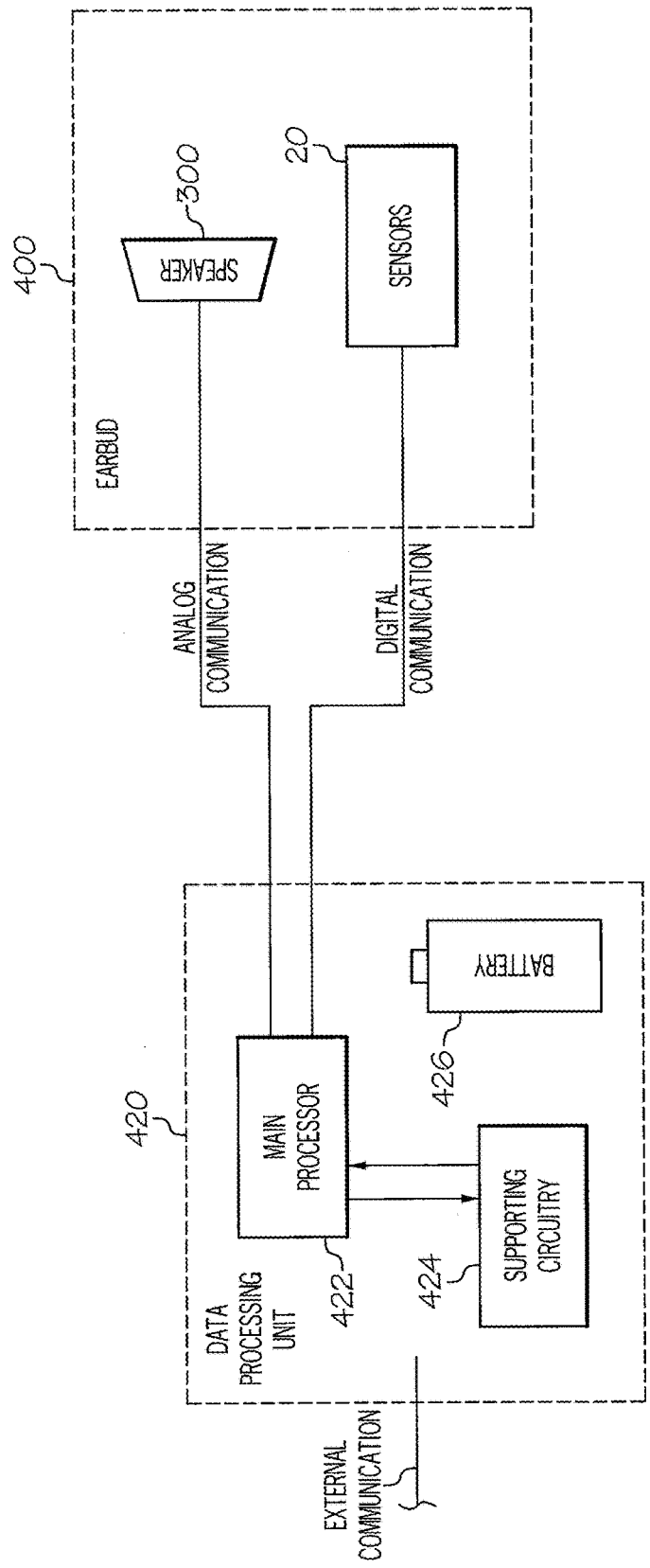
FIGS. 23-25 are block diagrams illustrating various configurations of a data processing unit in communication with an earbud having a sensor module, according to embodiments of the present invention.
Figure 24:
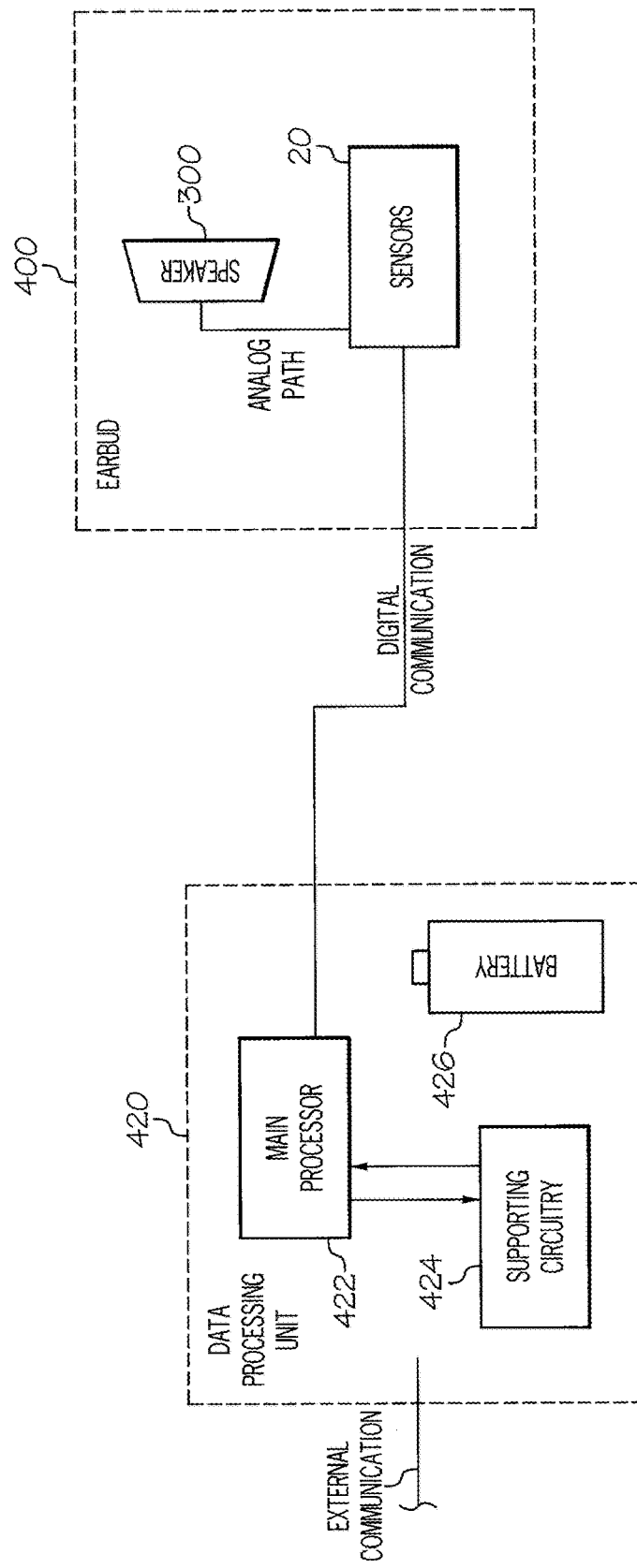
Figure 25:
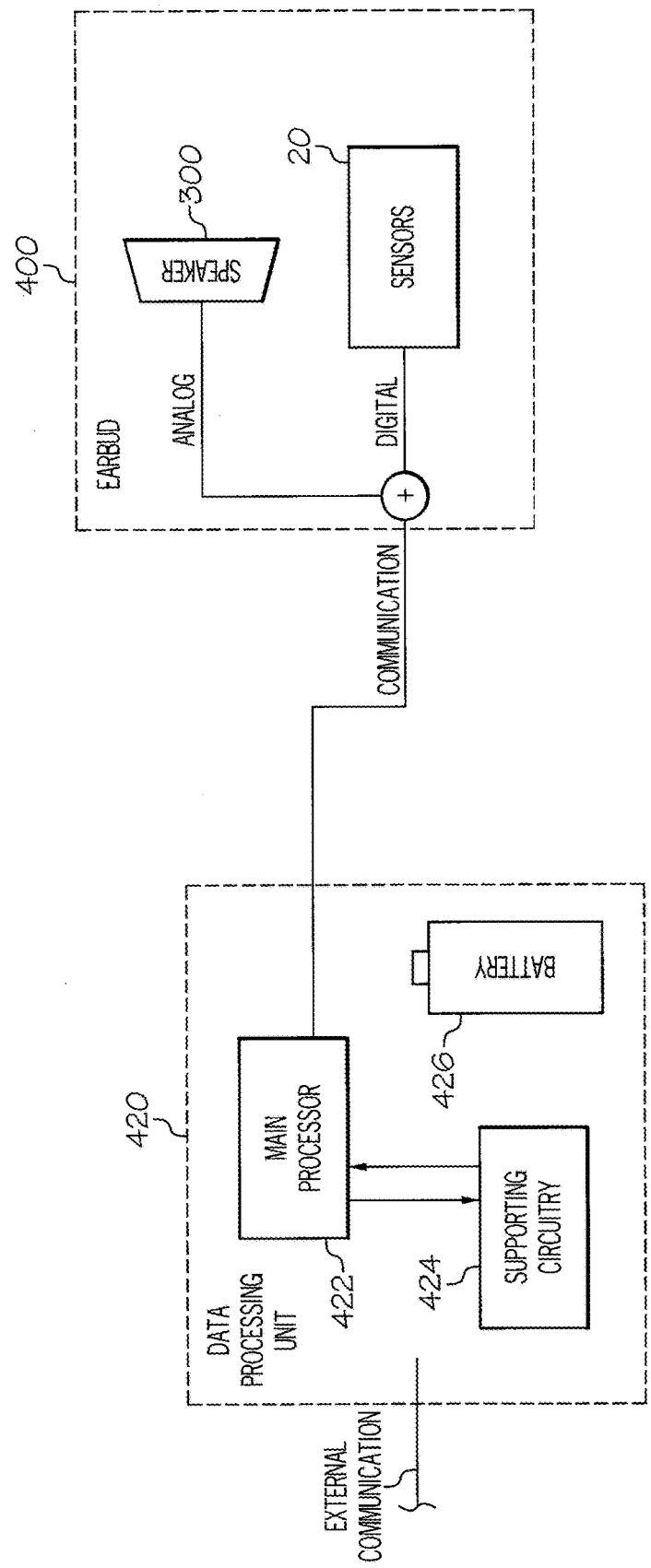

FIGS. 23-25 are block diagrams illustrating various configurations of a remote data processing unit 420 in communication with an earbud 400 having a sensor module 20, according to embodiments of the present invention. In each of the embodiments, the earbud 400 includes a speaker driver 300 and a sensor module 20, as described above. In each of the embodiments, the data processing unit 420 includes a processor 422, supporting circuitry 424, and a power source 424, such as a battery, capacitor, power regulating circuitry, energy harvesting power source, and/or a connection to an external power source, as would be understood by one skilled in the art. Data from the sensor module 20 is processed by the data processing unit 420. The data processing unit 420 is configured to communicate with another device via wired or wireless communication.

In the embodiment illustrated in FIG. 23, the processor 422 of the remote data processing unit 420 is in analog communication with the speaker driver 300 and is in digital communication with the sensor module 20.

In the embodiment illustrated in FIG. 24, the processor 422 of the remote data processing unit 420 is in digital communication with the sensor module 20. The sensor module 20 may include a digital to analog converter to provide an audio signal to the speaker driver 300.

In the embodiment illustrated in FIG. 25, the processor 422 of the remote data processing unit 420 communicates with the speaker driver 300 of the earbud 400 via analog communication with an embedded digital signal. In some embodiments, this analog communication may be wired and in others it may be wireless. The embedded digital signal may be "quasi-digital", as a modulated signal within the analog signal, such that both audio information and biometric sensor information are integrated within the analog signal. Such modulation may be achieved on the earbud 400 itself (as represented by the "+" sign in FIG. 25) using modulation techniques that are well-known by those skilled in the art (see, for example, U.S. Patent Application Publication No. 2014/0140567, which is incorporated herein by reference in its entirety). The data processing unit 420 may be located with the earbud 400 or may be located away from the earbud 400, with analog communication between the data processing unit 420 and the earbud 400. At least part of the functionality of the data processing unit 420 may comprise demodulation of the audio+biometric sensor signals, such that each can be addressed separately for audio communication and biofeedback. The data processing unit 420 may be in wireless or wired communication with an external device or external circuitry. A key benefit of the illustrated embodiment is that it enables the data processing unit 420 to be integrated within a smartphone or other smart device via the analog audio jack of the device, with analog communication to the earbud 400. Thus, a separate digital connection to the smart device would not be required in such a configuration, as both the audio and biometric signals are modulated and demodulated in an analog fashion.

Figure 26:
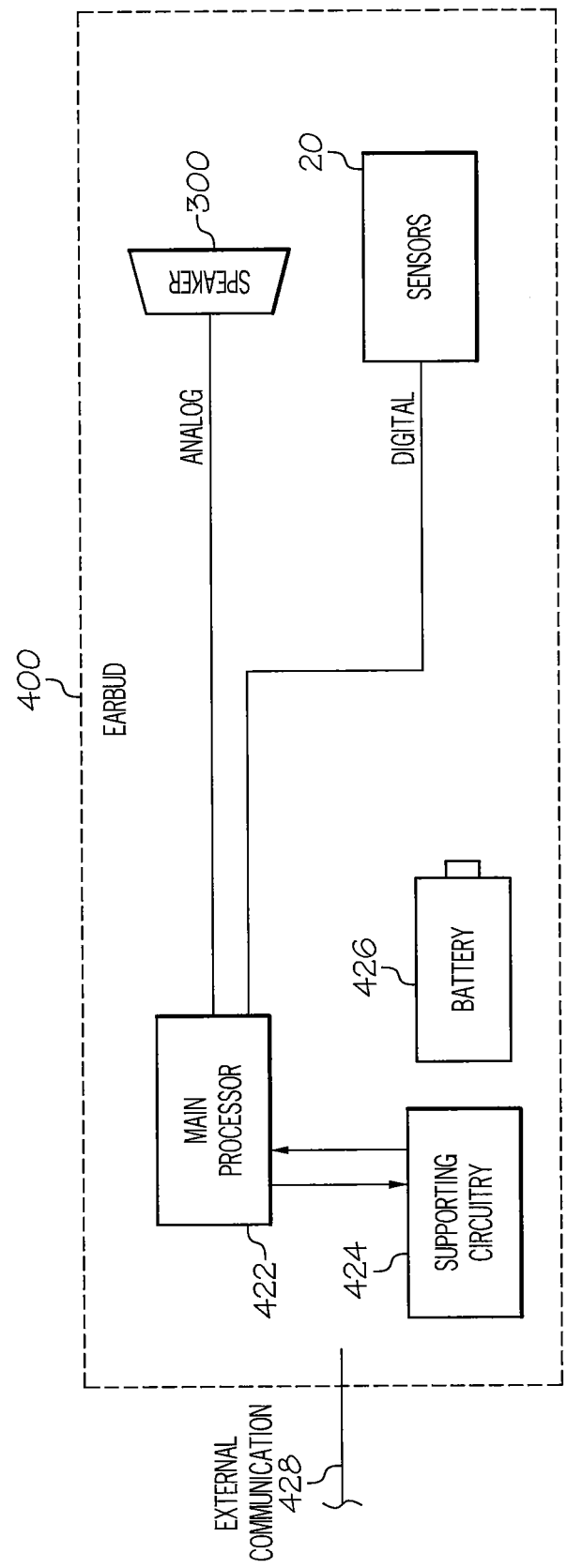
FIG. 26 is a block diagram an earbud having a sensor module and data processing capability, according to some embodiments of the present invention.

FIG. 26 is a block diagram of an earbud 400 having both a sensor module 20 and data processing capability, according to some embodiments of the present invention. The earbud 400 may include a speaker driver 300 and a sensor module 20, as described above, and may include a processor 422, supporting circuitry 424, and a power source 424, such as a battery or a connection area to access an external power source via a port or through soldering. Data from the sensor module 20 is processed by the processor 422. The processor 422 is configured to communicate with other devices, including another earbud, via wired or wireless communication 428. The processor 422 is in analog communication with the speaker driver 300 and is in digital communication with the sensor module 20.

A key benefit of the embodiment of FIG. 26 is that it enables an integrated earbud unit. Such a design may fit within a "true wireless" wireless stereo headset, where there are two separate earpieces available for each ear, with each earpiece in wireless communication with the other. In such an embodiment, each earpiece may comprise the structure of FIG. 26, such that each earpiece comprises sensors and supports audio communication. Moreover, having the driver circuitry, light-guiding, and sensor circuitry integrated as a unit can help reduce the spacing requirements for such a dual-wireless design, where space is fundamentally limited by the size of a subject's ears.

Figure 27:
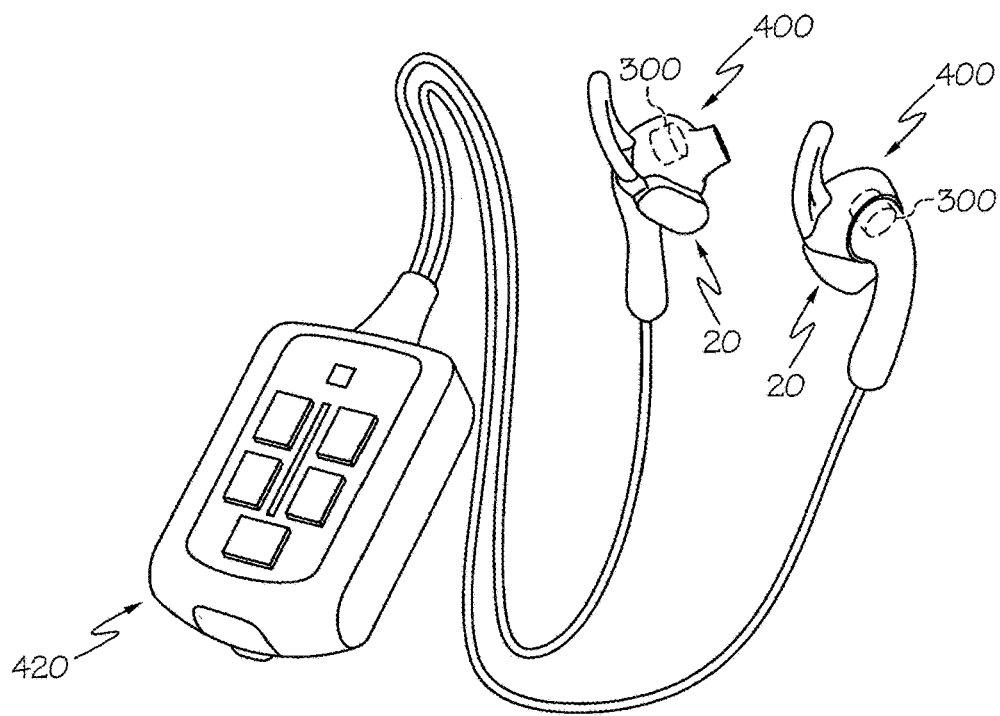
FIG. 27 illustrates a pair of earbuds which each contain a sensor module according to embodiments of the present invention, and which are in communication with a data processing unit.

FIG. 27 illustrates a pair of earbuds 400 according to some embodiments of the present invention. Each earbud 400 includes a speaker driver 300 and sensor module 20, as described above. Each earbud 400 is connected to a remote data processing unit 420, which may include a processor, supporting circuitry, and a power source, as described above. Data from each sensor module 20 is processed by the data processing unit and can be communicated to other devices via wired or wireless communication.

Figure 28:
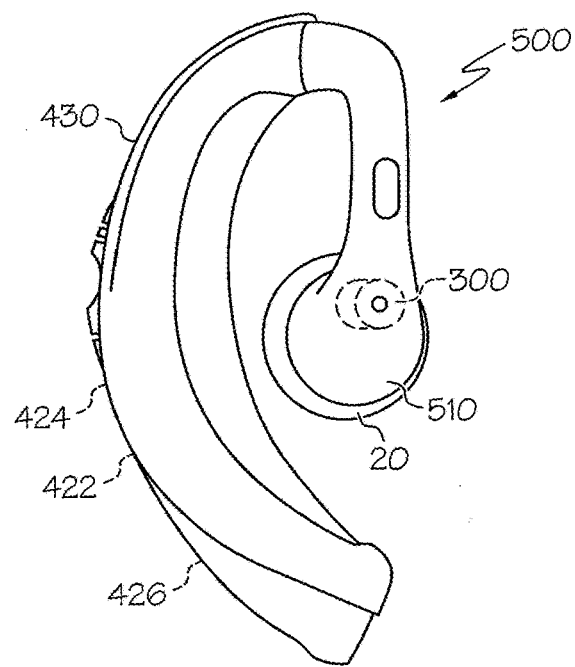
FIG. 28 illustrates an earbud unit containing a sensor module and a data processing unit, according to some embodiments of the present invention.

FIG. 28 illustrates an earbud 400 having both a sensor module 20 and data processing capability, according to some embodiments of the present invention. The earbud 400 includes a speaker driver 300 and a sensor module 20, as described above. The earbud 400 also includes a processor 422, supporting circuitry 424, and a power source 426, such as a battery, enclosed within a housing 430. The housing 430 is configured to be supported by the ear of a subject. Data from the sensor module 20 is processed by the processor 422. The processor 422 is configured to communicate with other devices via wired or wireless communication. As described above with respect to FIG. 26, this embodiment may comprise two separate earbuds 400 in wireless communication with each other. Moreover, the electronics may be integrated completely with the earbuds 400 alone, such that earhooks may not be required.

Figure 29:
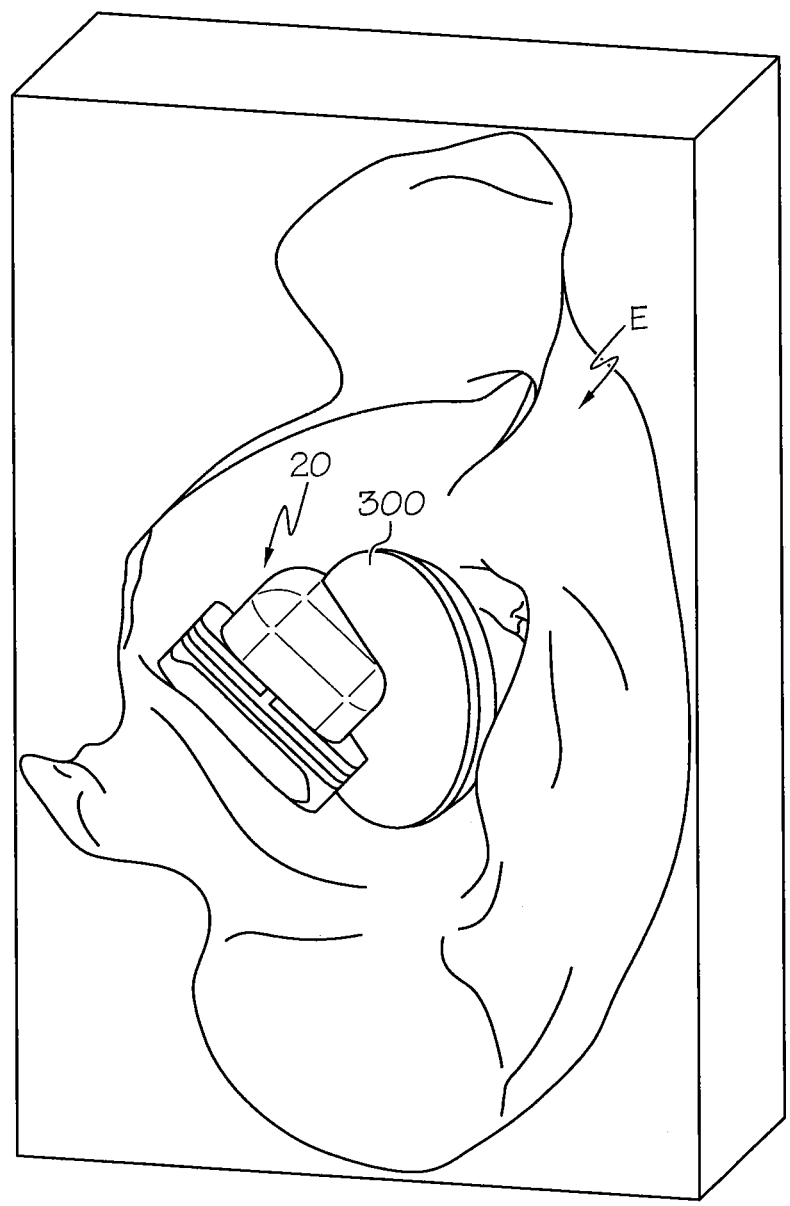
FIGS. 29-31 illustrate a speaker driver sensor positioned within an ear of a subject, according to some embodiments of the present invention.
Figure 30:
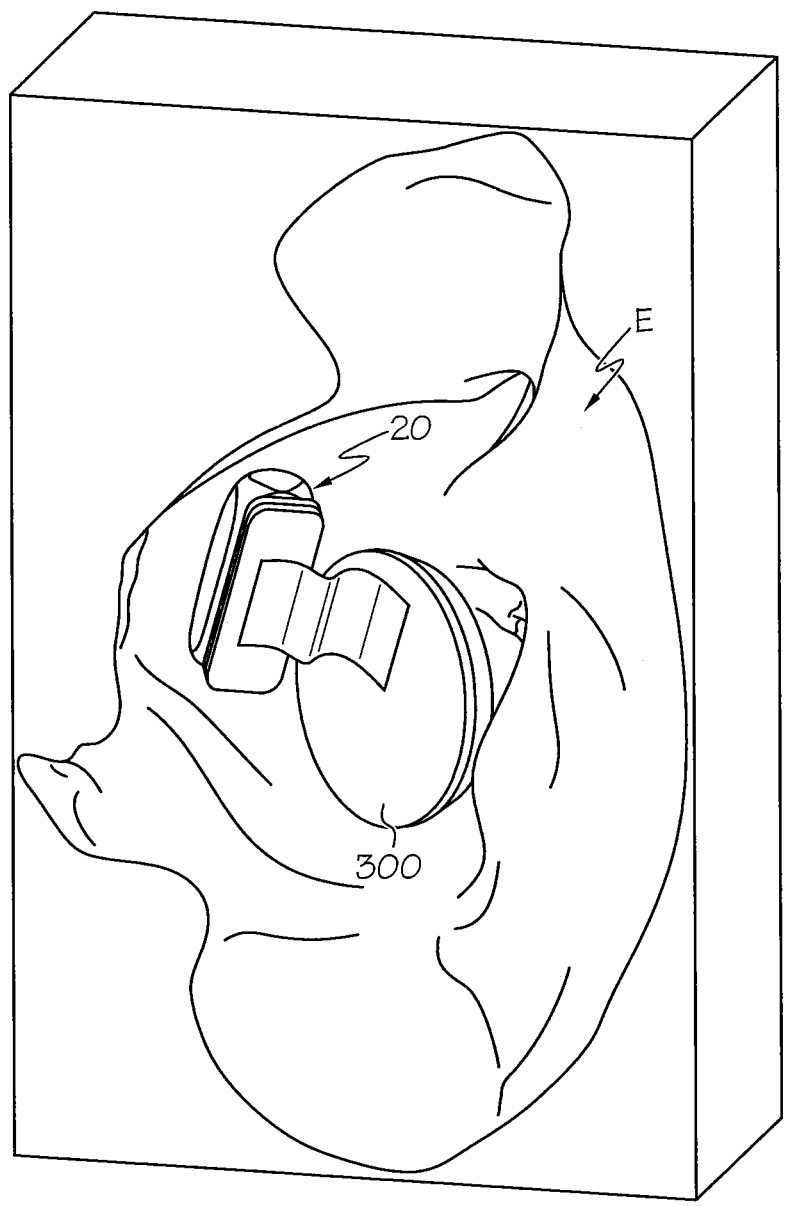
Figure 31:
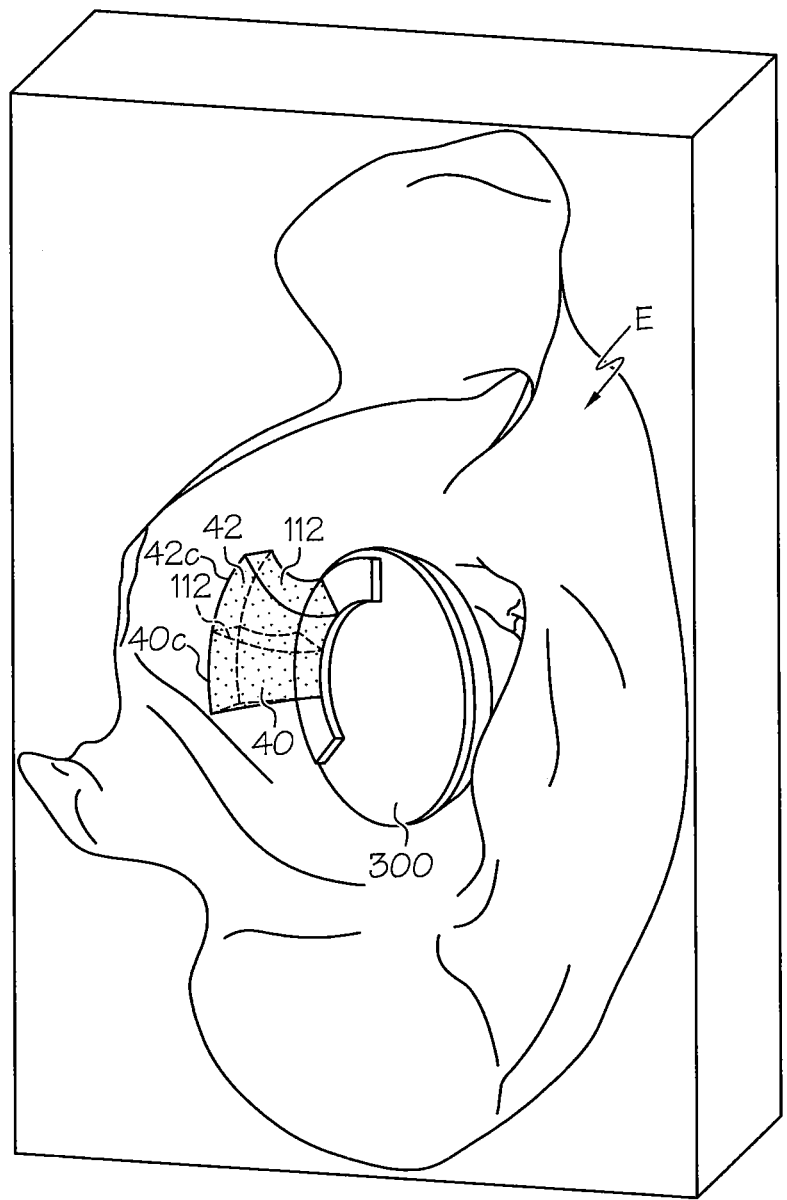

FIGS. 29-31 illustrate a speaker driver 300 having integrated light guiding, with sensor locations positioned in various spots within an ear E of a subject, according to some embodiments of the present invention. These figures show designs where the light guiding couples between the speaker driver 300 and sensor module 20, and wherein the sensor module 20 is located at various regions of the ear E. The light guiding may be supported by the earbud housing (not shown), by adhesive (such as glue or welding byproducts), overmolding, integrated alignment tabs, or the like. To simplify the image to emphasize sensor placement, the separations and barrier regions between the emitter and detector light-guiding is not shown (however, examples are provided in FIG. 12 and FIG. 13). FIG. 29 shows a configuration where the light is guided towards a region of the ear E between the anti-tragus and concha of the ear. FIG. 30 shows a configuration where the light is guided between the anti-helix and concha of the ear E. FIG. 31 shows how the light guiding may be configured, with the sensor module removed for clarity. The light guiding may also be contoured to couple from the sensor elements on the speaker driver 300 to the concha of the ear or other ear location.

In some embodiments, one or both of the light guides 40, 42 may be surrounded or partially surrounded by a cladding/barrier material 112 that is configured to at least partially block light from an external source from entering one or both of the light guides 40, 42 at select locations along the light guides 40, 42 and/or at least partially confine light within one or both light guides 40, 42. The cladding/barrier material 112 may be a light blocking material and/or a light reflective material and/or a material that has a higher optical scattering coefficient than the light guiding material of the light guides 40, 42. For example, the cladding material 112 may be a dark (e.g., black, etc.) or silver (or other reflective color) coating, a material with refractive index that differs from (i.e., is less than) the core light guide material, or a texturized light-scattering material on one or more portions of a distal end surface 40c, 42c of one or both of the light guides 40, 42.

FIGS. 32A-32F illustrate a biometric monitoring device 200 configured to be secured within an ear of a user and that may incorporate the sensor module 20 and light guides 40, 42 described above. The illustrated device 200 includes an earpiece body 202, a sensor module 204, a stabilizer 206, a sound port 208, and a connection point 210. The sensor module 204 includes angled light guides 40, 42 as described above with respect to FIG. 2. The illustrated device 200 is configured to be positioned within an ear of a user so as to reduce movement of the device 200. The various components are designed to matingly engage with specific contact points within an ear. For example, the sensor module 204 is configured to engage the region between the anti-tragus and concha of the ear and the stabilizer is configured to engage the anti-helix.

The illustrated device 200 is designed such that its center of gravity CG (FIGS. 32A-32C) is positioned at a location that provides enhanced stability to the device 200 when positioned within an ear of a user. The illustrated location of the CG helps prevent the device 200 from becoming dislodged from an ear of a user during user movement, including extreme activities, such as running and exercising. Moreover, the location of the CG is such that the device 200 is resistant to rotation when positioned within the ear of a user.

Figure 32C:
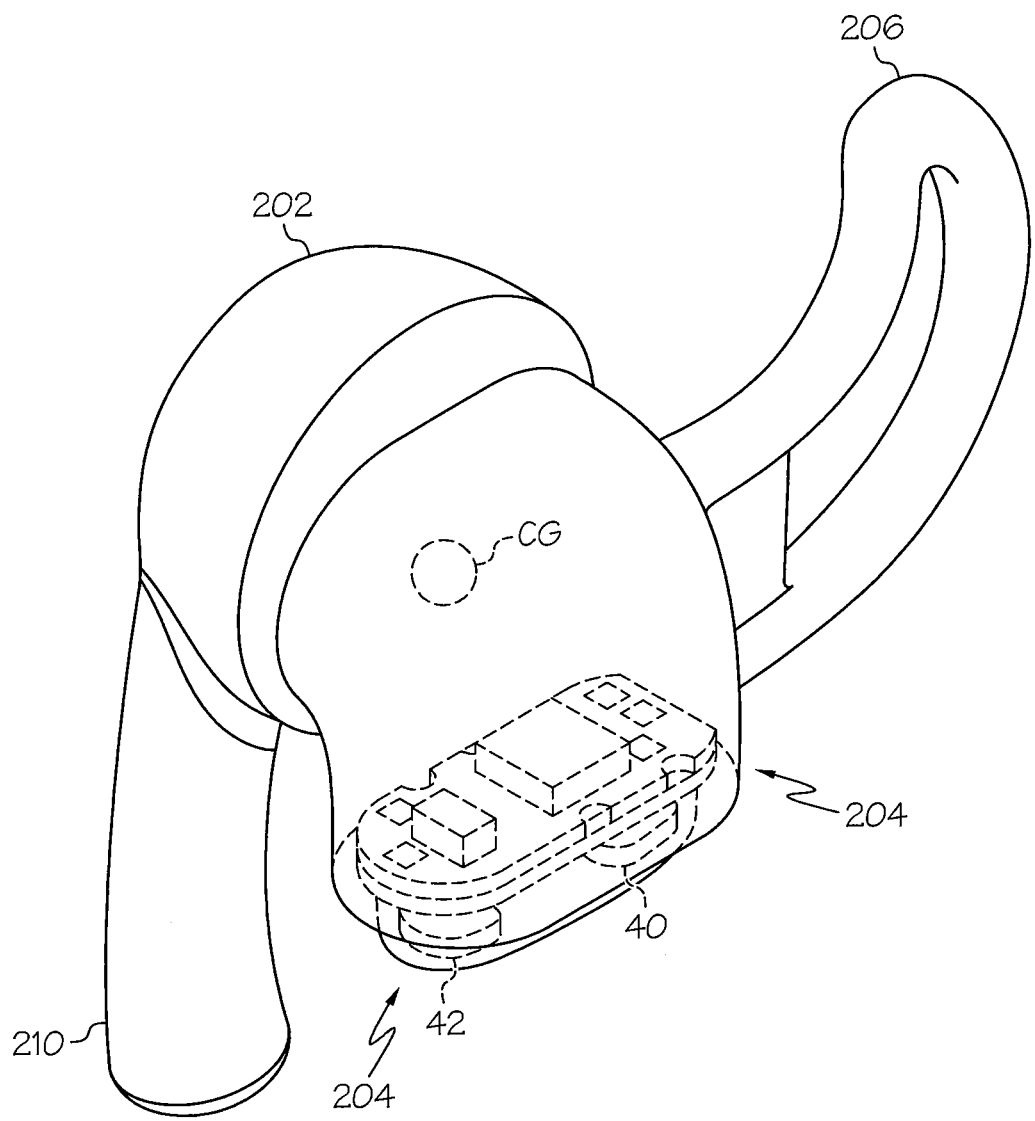
FIG. 32C is a front perspective view of the biometric monitoring device of FIG. 32A.
Figure 32E:
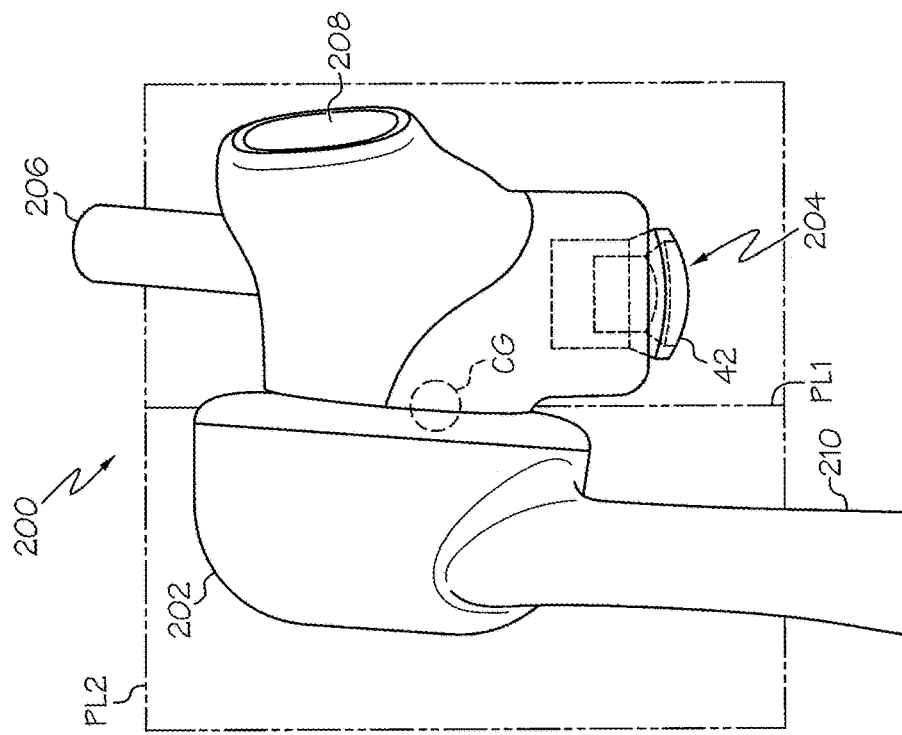
FIG. 32E is a side view of the biometric monitoring device of FIG. 32D.
Figure 32D:
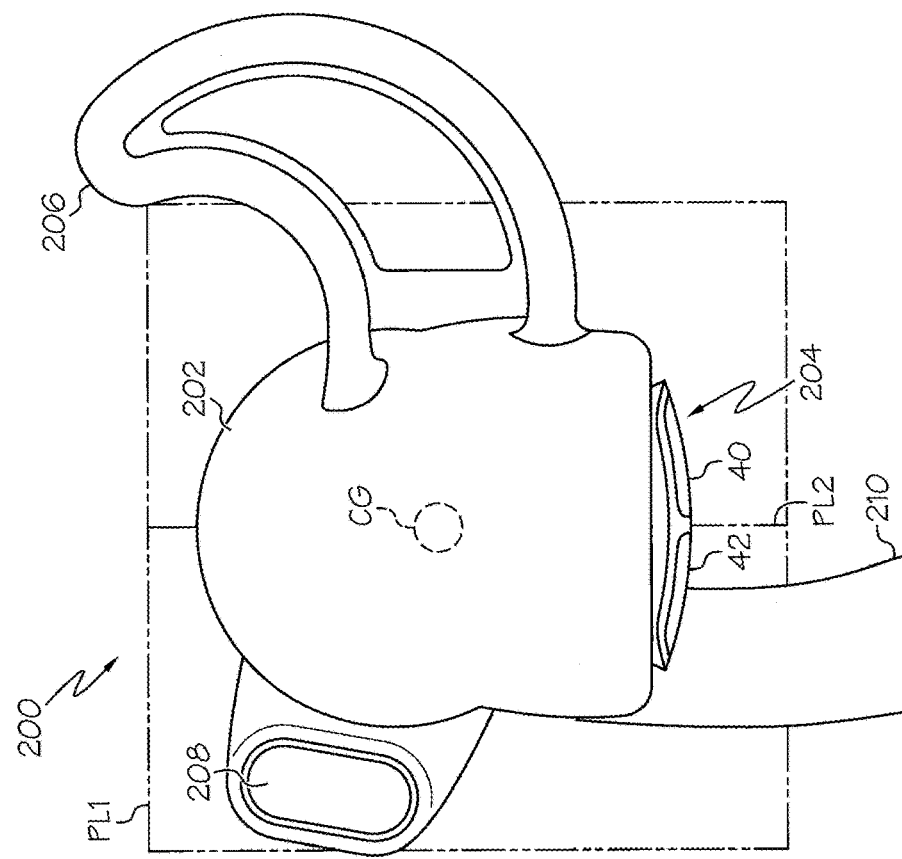
FIG. 32D is a front view of the biometric monitoring device of FIG. 32A illustrating the intersection of orthogonal planes along which the center of gravity of the monitoring device is located.
Figure 32F:
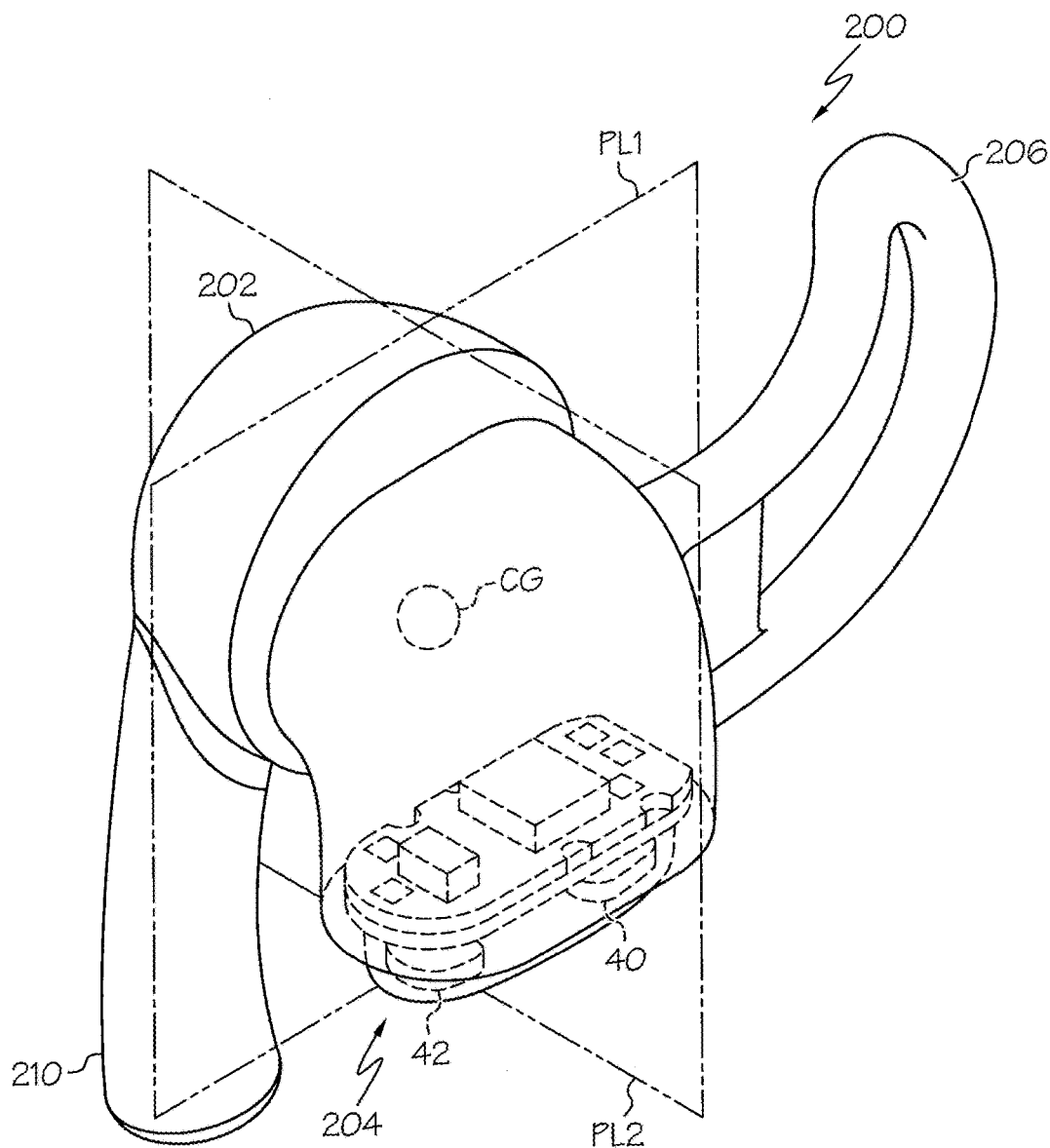
FIG. 32F is a front perspective view of the biometric monitoring device of FIG. 32D.

The center of gravity CG of the illustrated device 200 is located along the intersection of orthogonal planes PL1 and PL2 (FIGS. 32D-32F). As illustrated, plane PL2 bisects the center of the sensor module 204 and, in this particular embodiment, the center of gravity CG of the device 200 goes through the middle of the anti-tragus/concha divide in the ear, where the sensor module 204 of the monitoring device 200 is aligned.

Figure 33:
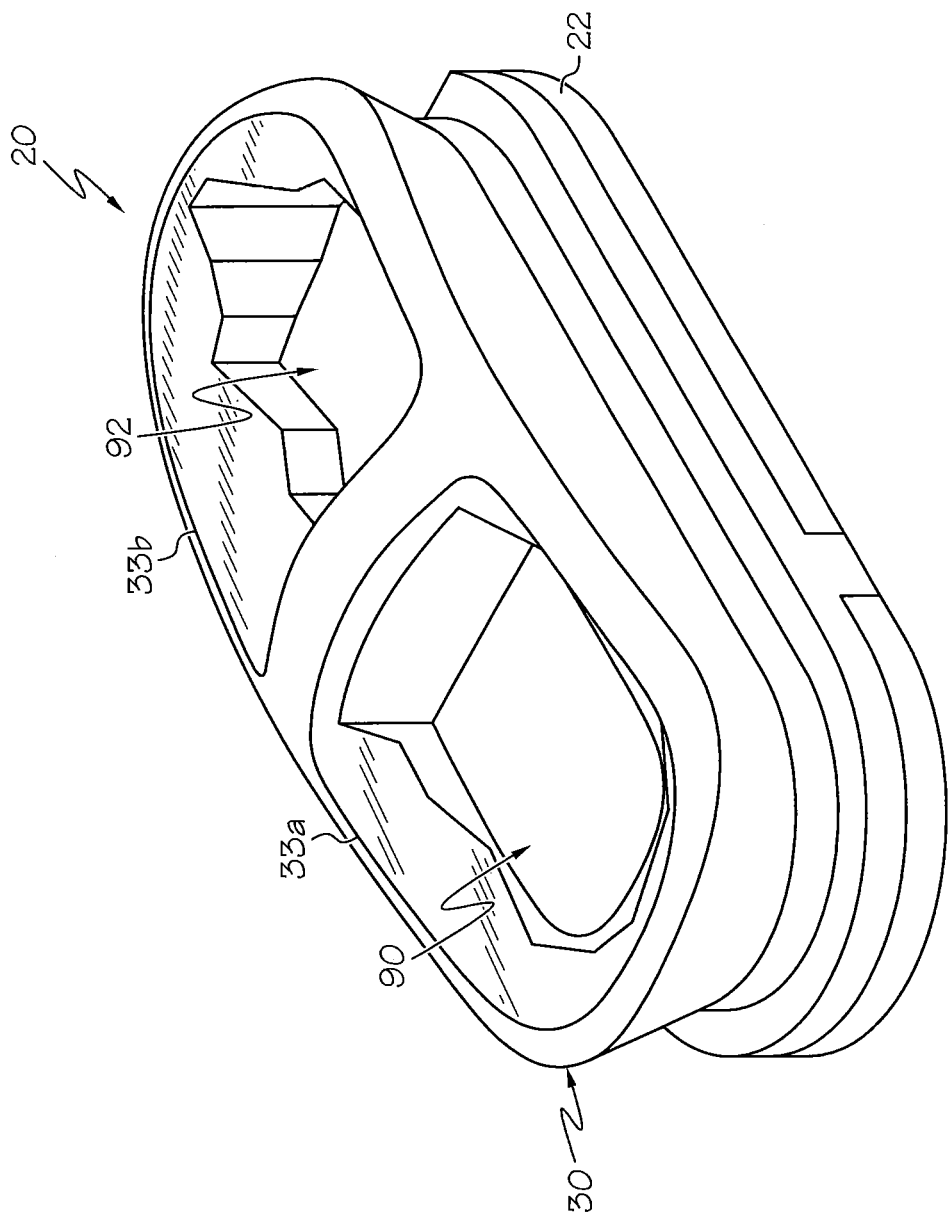
FIG. 33 is a top perspective view side section view of an optical sensor module that includes at least one light polarizing element, according to some embodiments of the present invention.
Figure 34:
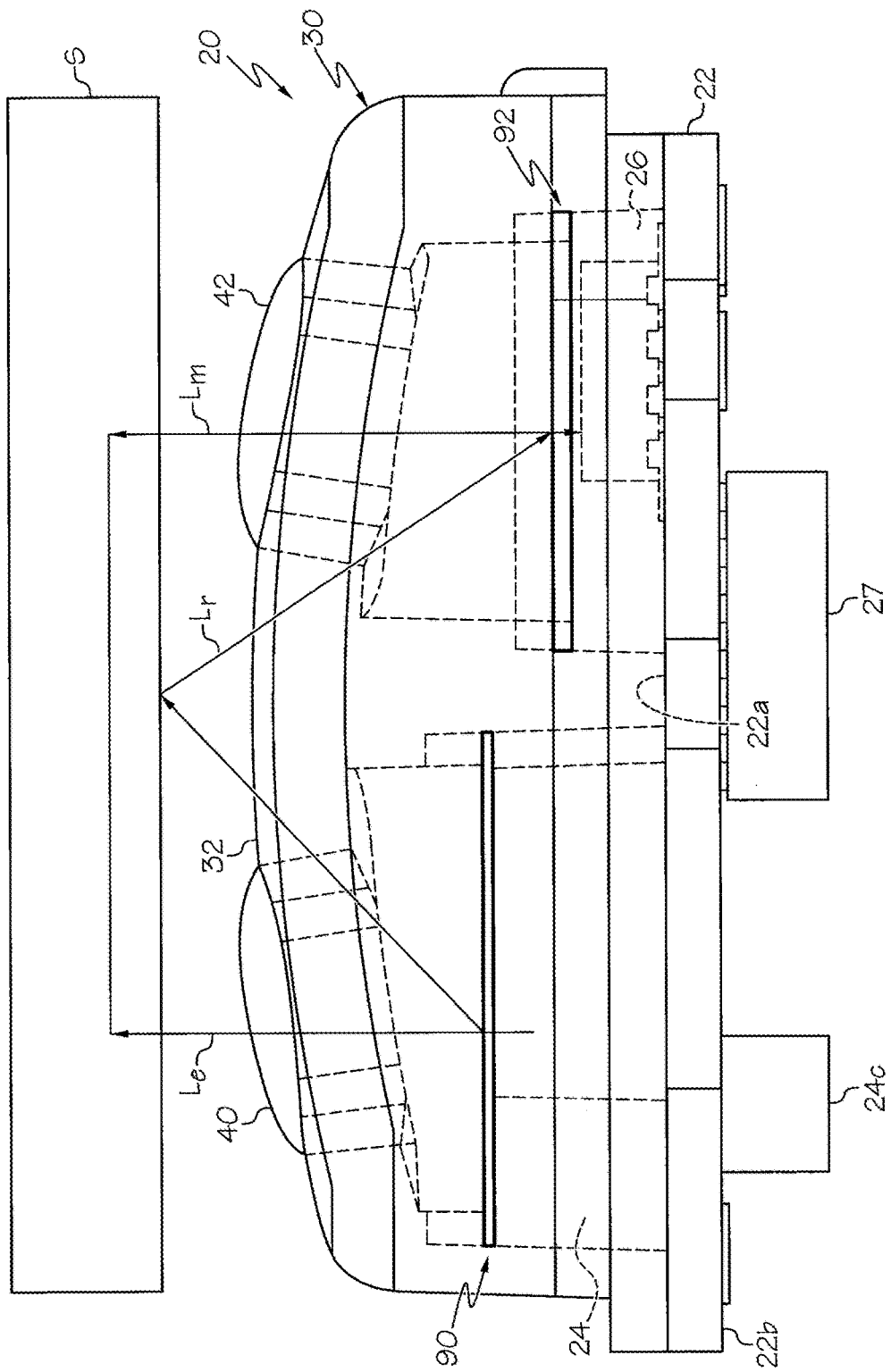
FIG. 34 is a side section view of the optical sensor module of FIG. 33.

FIGS. 33 and 34 illustrate an optical sensor module 20 that can be used with various monitoring devices in proximity to the skin, such as monitoring devices that are integrated into earbuds, armbands, wristbands, rings, patches, eyewear, headbands, and the like, according to some embodiments of the present invention. The illustrated sensor module 20 includes a substrate or base 22 (e.g., a circuit board, etc.) having an optical source 24 and an optical detector 26 on one side 22a thereof. The base 22 may support and/or be connected to various electronic components including, but not limited to, a signal processor, a wireless module for communicating with a remote device, a memory storage device, etc. Moreover, a battery, such as a lithium polymer battery or other portable battery, may be mounted to or connected to the base 22 and may be charged via a charge port, such as a USB charge port for example. Additionally, the base 22 may be flexible, or rigid, or may be formed from a combination of flexible and rigid material, or various other base constructs suitable for supporting electronics. In the illustrated embodiment, a capacitor 24c for driving the optical source 24 and an accelerometer 27 are mounted to an opposite side 22b of the base 22.

The optical source 24 may be one or more light-emitting diodes (LED), laser diodes (LD), organic light-emitting diodes (OLEDs), compact incandescent bulbs, microplasma emitters, IR blackbody sources, or the like. The optical detector 26 may be one or more photodiodes, photodetectors, phototransistors, thyristors, solid state devices, optical chipsets, or the like.

A housing 30 is secured to the base 22 and overlies the optical source 24 and optical detector 26. The illustrated housing 30 has a curved outer surface 32 that is configured to engage a particular portion of the body of a user of the sensor module 20. For example, in some embodiments, the sensor module 20 may be incorporated into an earbud and the housing outer surface 32 is contoured to matingly engage a particular region of the ear (e.g., the region between the anti-tragus and the concha, the region along the helix or anti-helix of the ear, the skin of the ear canal, etc.). However, the housing outer surface 32 may have various shapes and configurations and need not be curved. For example, a wristband module applying the invention may have a flat housing outer surface 32.

The housing 30 includes a first light guide 40 in optical communication with the optical source 24 and a second light guide 42 in optical communication with the optical detector 26. In addition to supporting the first and second light guides 40, 42, the housing 30 may be configured to enclose and protect the various electronic components mounted to the base 22 from ambient interference (air, humidity, particulates, electromagnetic interference, etc).

The housing 30 also includes a first light polarizing element 90 in optical communication with the optical source 24, and a second light polarizing element 92 in optical communication with the optical detector 26. The first polarizing light element 90 is configured to polarize light emitted by the optical source 24, and the second light polarizing element 92 is configured to polarize light detected by the optical detector 26. Although illustrated as first and second light polarizing elements 90, 92, in some embodiments, the sensor module 20 may utilize a single polarizing element that is in optical communication with one or both of the optical source 24 and optical detector 26.

In some embodiments, the first and second light polarizing elements 90, 92 have the same light polarization orientation (i.e., parallel planes of polarization). In other embodiments, the first and second light polarizing elements 90, 92 have respective different light polarization orientations. For example, the first and second light polarizing elements 90, 92 may have planes of polarization that are orthogonal (i.e., 90°) to each other.

In some embodiments, one or both of the first and second light polarizing elements 90, 92 may be a light polarizing film. In other embodiments, one or both of the first and second light polarizing elements 90, 92 may be a light polarizing lens. In other embodiments, one or both of the first and second light guides 40, 42 may include light polarizing material that serves the function of light polarizing elements 90, 92.

The illustrated sensor module housing 30 includes first and second windows 33a, 33b of optically transparent material through which light from the optical source passes and through which light detected by the optical detector passes, respectively. In some embodiments, the material of one or both of the first and second windows 33a, 33b may include polarizing material (e.g., a polarizing film, etc.) that serves as a polarizing element. One or both of the first and second windows 33a, 33b may also be configured to act as a lens.

In the illustrated embodiment of FIG. 34, the first and second light polarizing elements 90, 92 are polarizing films. Light $L_e$ emitted by the optical source 24 is polarized via the first light polarizing element 90, enters the skin S of a subject being monitored via the sensor module 20 and exits the skin S as modulated light $L_m$. The modulated light $L_m$ is polarized via the second light polarizing element 92 prior to entering the light detector 26. Some of the polarized light emitted by the light source 24 is reflected off (indicated by $L_r$) of the skin S of the subject. The second light polarizing element 92 suppresses this reflected light $L_r$. The modulated light $L_m$ that exits the skin S of the subject tends to be depolarized, and up to 50% of this light will traverse the second light polarizing element 92. In principle, light that is specularly reflected off the skin, which will have little if any desired blood flow (or other physiological) information about the subject wearing the module 20, will be sharply attenuated by a cross-polarization orientation of the first and second light polarizing elements 90, 92, with at least one of the first and second polarizing elements 90, 92 being off-axis with the other by approximately 90-degrees. Thus, during times of high skin motion, such as during running or during other aggressive exercise by the subject wearing the sensor module 20, specularly reflected motion artifacts may be attenuated such that mostly optical scatter signals from below the skin S will reach the optical detector 26.

Any suitable light polarizing material which will produce a light polarization effect may be utilized as the first and second light polarizing elements 90, 92 in the context of the present invention. Exemplary polarizing material that can be used in accordance with embodiments of the present invention is available from American Polarizers, Inc., Reading, Pa., as well as Edmund Optics, Barrington, N.J.

Figure 35:
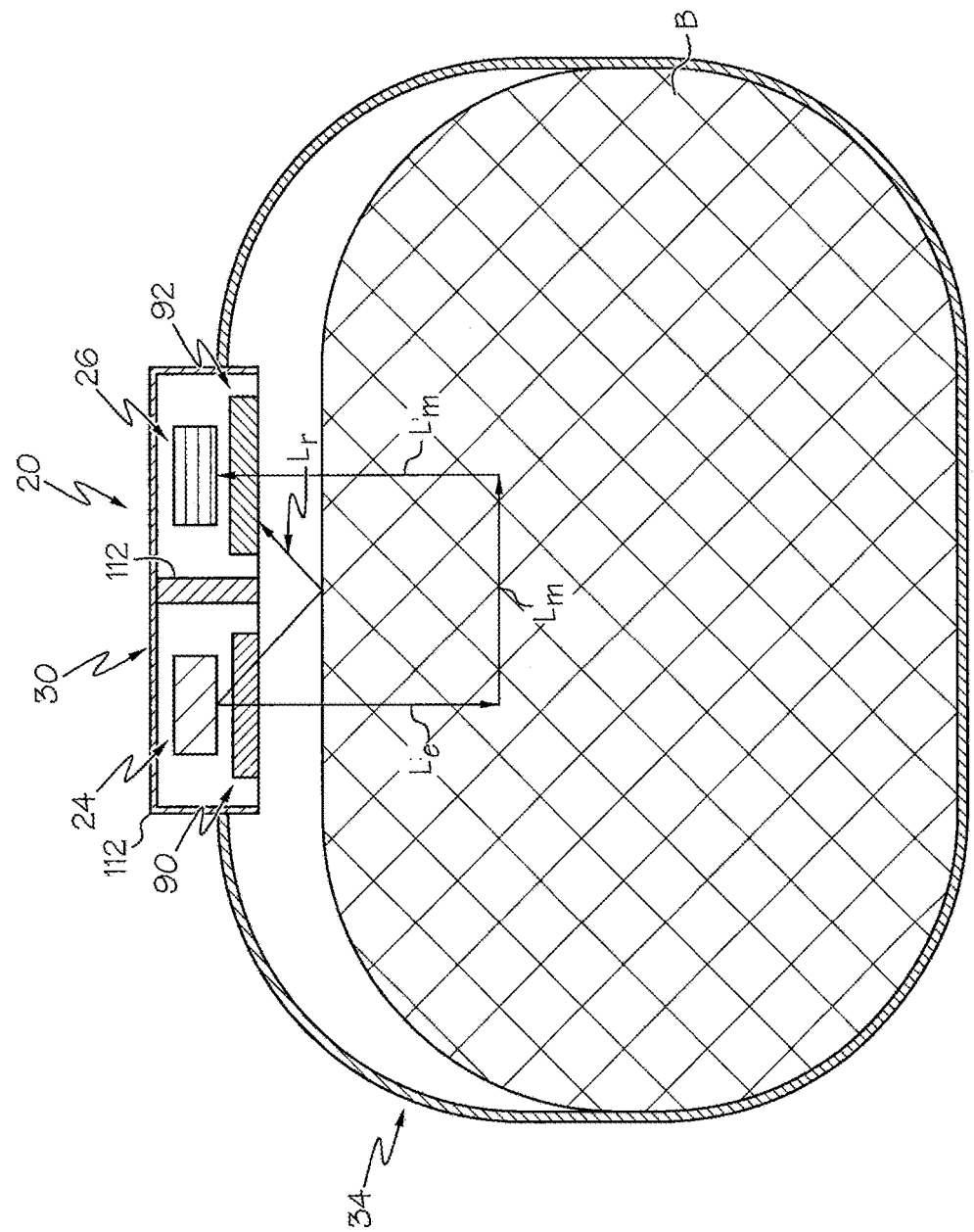
FIG. 35 is a side section view of an optical sensor module that includes at least one light polarizing element, according to some embodiments of the present invention.

The light-guiding material itself, or the lens material, may comprise polarizing material. Additionally, it should be noted that in some embodiments the polarizing material 90, 92 should be located on the outside of the light guides 40, 42 (as shown in FIG. 35), as the light-guiding itself may be depolarizing, depending on the material used and the structure of the light guide, and hence defeat the purpose of having polarizers at all. In such case, a polarization coating or filter on top of each light guide 40, 42 may be most effective. Such a film can be deposited, textured (etched, machined, imprinted, etc.), laminated, glued, or the like.

Referring now to FIG. 35, a sensor module 20 configured to be worn by a subject according to other embodiments of the present invention is illustrated. The sensor module 20 includes a housing 30 that supports an optical source 24 and an optical detector 26. A barrier 112 may be located between the optical source 24 and the optical detector 26 to reduce or eliminate cross-talk between the optical source 24 and optical detector 26. The housing also supports a first light polarizing element 90 in optical communication with the optical source 24 that is configured to polarize light emitted by the optical source 24, and a second light polarizing element 92 in optical communication with the optical detector 26 that is configured to polarize light detected by the optical source 24. The sensor module 20 may have a similar construction as the sensor module 20 of FIG. 34.

In some embodiments, the first and second light polarizing elements 90, 92 have the same light polarization orientation (i.e., parallel planes of polarization). In other embodiments, the first and second light polarizing elements 90, 92 have respective different light polarization orientations. For example, the first and second light polarizing elements 90, 92 may have planes of polarization that are orthogonal (i.e., 90°) to each other.

In some embodiments, one or both of the first and second light polarizing elements 90, 92 may be a light polarizing film. In other embodiments, one or both of the first and second light polarizing elements 90, 92 may be a light polarizing lens which may couple to light guides (not shown). In other embodiments, the housing 30 may include first and second windows as described above with respect to FIG. 34. In some embodiments, the first and second windows may include polarizing material that serve as the polarizing elements 90, 92.

The illustrated sensor module 20 is secured to a portion of the body B of a subject via a band or strap 34. For example, the body portion B may be a digit, an arm, a leg, a torso, etc., of a subject. Light $L_e$ emitted by the light source 24 traverses the light polarizing element 90 and either enters the body B or is reflected off of the surface of the body B. Light that enters the body B scatters multiple times, and is becomes depolarized $L_m$, such that when it exits the wrist, much of the light $L_m$ can traverse the second light polarizing element 92 and be detected by the light detector 26. Reflected light $L_r$ can be filtered out by the second light polarizing element 92 and can therefore be kept from the light detector 26. As such, the light detector 26 can detect primarily light from the light source 24 that has traveled through the tissue of the body B.

Any suitable light polarizing material which will produce a light polarization effect may be utilized as the first and second light polarizing elements 90, 92 in the context of the present invention.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. An earbud, comprising:
a speaker driver;
a printed circuit board (PCB) directly mounted on a surface of the speaker driver; and
a sensor module supported by the PCB and electrically connected to the speaker driver, wherein the sensor module comprises an optical source and an optical detector, and wherein the sensor module is configured to detect and/or measure physiological information from a subject wearing the earbud,
wherein the PCB is an elongated, flexible PCB having a distal end portion, and wherein the optical source and optical detector are secured to the PCB at the distal end portion.

2. The earbud of claim 1, further comprising a first light guide coupled to the optical source and/or a second light guide coupled to the optical detector, wherein the first light guide is configured to deliver light from the optical source into an ear region of the subject via a distal end thereof, and wherein the second light guide is configured to collect light from the ear region via a distal end thereof and deliver collected light to the optical detector.

3. The earbud of claim 1, further comprising at least one of the following secured to the PCB: an accelerometer, a humidity sensor, an altimeter, a temperature sensor.

4. The earbud of claim 1, further comprising at least one signal processor secured to the PCB that is configured to process signals produced by the optical detector.

5. The earbud of claim 1, wherein the earbud is in communication with a data processing unit configured to process signals produced by the optical detector.

6. An earbud, comprising:
a speaker driver;
a printed circuit board (PCB) directly mounted on a surface of the speaker driver;
an optical emitter and optical detector secured to the PCB; and
a light guide configured to guide light between the optical emitter and a body of a subject wearing the earbud, wherein the light guide comprises a distal end that is configured to engage a portion of the ear of the subject, and wherein the light guide is configured to guide light from the optical emitter to the portion of the ear via the distal end thereof.

7. The earbud of claim 6, further comprising a second light guide configured to guide light between the optical detector and the body of the subject.

8. The earbud of claim 7, wherein the second light guide comprises a distal end that is configured to engage a second portion of the ear of the subject, and wherein the second light guide is configured to collect light from the second ear region via the distal end thereof and deliver collected light to the optical detector.

9. The earbud of claim 6, wherein the PCB is a flexible circuit.

10. A speaker driver for an earbud, the speaker driver comprising:
an optical source secured directly to the speaker driver;
an optical detector secured directly to the speaker driver;
a first light guide extending outwardly from the optical source, wherein the first light guide is in optical communication with the optical source; and
a second light guide extending outwardly from the optical detector, wherein the second light guide is in optical communication with the optical detector.

11. The speaker driver of claim 10, further comprising at least one signal processor secured directly to the speaker driver and configured to process signals produced by the optical detector.

12. The speaker driver of claim 10, further comprising at least one of the following secured directly to the speaker driver: an accelerometer, a humidity sensor, an altimeter, a temperature sensor.

13. The speaker driver of claim 10, wherein the speaker driver comprises opposite front and rear portions, wherein sound is emitted through at least one aperture formed in the front portion, and wherein the optical source and the optical detector are directly secured to the rear portion of the speaker driver.

* * * * *